(12) United States Patent
Arend et al.

(10) Patent No.: US 7,928,120 B2
(45) Date of Patent: Apr. 19, 2011

(54) CYANOISOQUINOLINE COMPOUNDS AND METHODS OF USE THEREOF

(75) Inventors: Michael Arend, Foster City, CA (US); Lee A. Flippin, Woodside, CA (US); Min Wu, Sunnyvale, CA (US); Eric D. Turtle, Belmont, CA (US); Wen-Bin Ho, Los Altos, CA (US); Shaojiang Deng, San Mateo, CA (US)

(73) Assignee: FibroGen, Inc., San Francisco, CA (US)

( * ) Notice: Subject to any disclaimer, the term of this patent is extended or adjusted under 35 U.S.C. 154(b) by 508 days.

(21) Appl. No.: 11/627,906

(22) Filed: Jan. 26, 2007

(65) Prior Publication Data

US 2007/0298104 A1    Dec. 27, 2007

Related U.S. Application Data

(60) Provisional application No. 60/762,780, filed on Jan. 27, 2006.

(51) Int. Cl.
    A01N 43/42    (2006.01)
    A01N 43/40    (2006.01)
    A61K 31/47    (2006.01)
    A61K 31/435   (2006.01)
    A61K 31/44    (2006.01)
(52) U.S. Cl. ......... 514/307; 514/277; 514/279; 514/299
(58) Field of Classification Search ................. 564/141; 514/307, 299, 279, 277
See application file for complete search history.

(56) References Cited

U.S. PATENT DOCUMENTS

| | | |
|---|---|---|
| 3,989,704 A | 11/1976 | Houlihan et al. |
| 4,036,964 A | 7/1977 | Buckle et al. |
| 4,260,611 A | 4/1981 | Bartmann et al. |
| 4,559,403 A | 12/1985 | Bruderer et al. |
| 4,584,379 A | 4/1986 | Wagner |
| 4,673,682 A | 6/1987 | Konz et al. |
| 4,822,800 A | 4/1989 | Faltico et al. |
| 4,952,588 A | 8/1990 | Glamkowski et al. |
| 4,966,906 A | 10/1990 | Glamkowski et al. |
| 5,620,995 A | 4/1997 | Weidmann et al. |
| 5,658,933 A | 8/1997 | Weidmann et al. |
| 5,719,164 A | 2/1998 | Weidmann et al. |
| 6,093,730 A | 7/2000 | Weidmann et al. |
| 6,319,931 B1 | 11/2001 | Kroemer et al. |
| 6,358,973 B1 | 3/2002 | Napoletano et al. |
| 6,358,976 B1 | 3/2002 | Wityak et al. |
| 6,369,053 B1 | 4/2002 | Yuan et al. |
| 6,762,318 B2 | 7/2004 | Kodra et al. |
| 6,777,425 B2 | 8/2004 | Burli et al. |
| 6,903,114 B2 | 6/2005 | Backstrom et al. |
| 7,208,601 B2 | 4/2007 | Majalli et al. |
| 7,248,053 B2 | 7/2007 | Houldsworth |
| 7,294,457 B2 | 11/2007 | Kukolj et al. |
| 7,323,475 B2 | 1/2008 | Arend et al. |
| 2003/0153503 A1 | 8/2003 | Klaus et al. |
| 2003/0176317 A1 | 9/2003 | Guenzler-Pukall et al. |
| 2004/0204356 A1 | 10/2004 | Guenzler-Pukall et al. |
| 2004/0235082 A1 | 11/2004 | Fourney et al. |
| 2005/0020487 A1 | 1/2005 | Klaus et al. |
| 2006/0035965 A1 | 2/2006 | Dalton et al. |
| 2006/0178316 A1 | 8/2006 | Klaus et al. |
| 2006/0183695 A1 | 8/2006 | Klaus et al. |
| 2006/0199836 A1 | 9/2006 | Turtle et al. |
| 2006/0217416 A1 | 9/2006 | Arend et al. |
| 2006/0251638 A1 | 11/2006 | Guenzler-Pukall |
| 2006/0258660 A1 | 11/2006 | Guenzler-Pukall et al. |
| 2006/0270699 A1 | 11/2006 | Guenzler-Pukall et al. |
| 2006/0276477 A1 | 12/2006 | Klaus et al. |
| 2007/0004627 A1 | 1/2007 | Seeley et al. |
| 2007/0155784 A1 | 7/2007 | Arend et al. |
| 2007/0185159 A1 | 8/2007 | Arend et al. |
| 2007/0292433 A1 | 12/2007 | Seeley et al. |
| 2007/0293575 A1 | 12/2007 | Seeley et al. |
| 2008/0004309 A1 | 1/2008 | Deng et al. |

FOREIGN PATENT DOCUMENTS

| | | |
|---|---|---|
| CA | 2134866 | 5/1995 |
| EP | 532466 | 3/1993 |
| EP | 0650960 | 9/1994 |
| EP | 0650961 | 10/1994 |
| EP | 626178 | 11/1994 |
| EP | 706795 | 4/1996 |
| EP | 0911340 | 4/1999 |
| EP | 1 676 834 A1 | 7/2006 |
| JP | A-H07-224039 | 8/1995 |
| JP | A-H07-228571 | 8/1995 |

(Continued)

OTHER PUBLICATIONS

U.S. Appl. No. 11/495,118, filed Jul. 28, 2006, Guenzler-Pukall et al.

(Continued)

*Primary Examiner* — Yong S Chong
(74) *Attorney, Agent, or Firm* — Foley & Lardner LLP

(57) ABSTRACT

The present invention relates to cyanoisoquinoline compounds suitable for use in treating hypoxia inducible factor-mediated and/or erythropoietin-associated conditions. The cyanoisoquinoline compounds of the invention have the following structure:

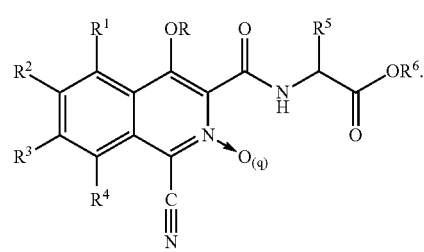

36 Claims, No Drawings

FOREIGN PATENT DOCUMENTS

| | | |
|---|---|---|
| JP | A-H11-302257 | 11/1999 |
| WO | WO 96/18616 | 6/1996 |
| WO | WO 98/50343 | 11/1998 |
| WO | WO 98/50346 | 11/1998 |
| WO | WO 01/58892 | 8/2001 |
| WO | WO 02/070510 | 9/2002 |
| WO | WO 02/074981 | 9/2002 |
| WO | WO 02/100832 A1 | 12/2002 |
| WO | WO 02/101073 | 12/2002 |
| WO | WO 03/007945 | 1/2003 |
| WO | WO 03/010141 | 2/2003 |
| WO | WO 03/014377 | 2/2003 |
| WO | WO 03/049686 | 6/2003 |
| WO | WO 03/080566 | 10/2003 |
| WO | WO 2004/108681 A1 | 12/2004 |
| WO | WO 2005/009962 | 2/2005 |
| WO | WO 2005/014533 A2 | 2/2005 |

OTHER PUBLICATIONS

U.S. Appl. No. 11/406,484, filed Apr. 17, 2006, Klaus et al.
U.S. Appl. No. 12/015,275, filed Jan. 16, 2008, Arend et al.
Bickel et al. *Hepatology*, 28:404-411 (1998).
Cockman et al., *J. Biol. Chem.*, 275:25733-25741 (2000).
Franklin et al., *Biochem J.*, 353:333-338 (2000).
Franklin, et al. "Approaches to the design of anti-fibrotic drugs" *Biochem. Soc. Trans.* 19(4): 812-815 (1991).
Friedman et al. *Proc. Natl. Acad. Sci. USA*, 97:4736-4741 (2000).
Iliopoulus et al., *Proc. Natl. Acad. Sci. USA*, 93:10595-10599 (1996).
Ivan, et al. "HIFα Targeted for VHL-Mediated Destruction by Proline Hydroxylation: Implications for O2 Sensing", *Science*, 292:464-468.
Jaakkola et al. (2001), "Targeting of HIF-alpha to the von Hippel-Lindau ubiquitylation complex by $O_2$-regulated prolyl hydroxylation," *Science* 292 (5516):468-472.
Jiang et al., *J. Biol. Chem.*, 271:17771-17778 (1996).
Kivirikko et al. *Matrix Biol.*, 16:357-368 (1998).
Lando, et al. "Oxygen-dependent regulation of hypoxia-inducible factors by prolyl and asparaginyl hydroxylation", *Eur. J. Biochem*, 270:781-790 (2003).
Majamaa et al. *Biochem J.*, 229:127-133 (1985).
Majamaa et al. *Eur. J. Biochem.*, 138:239-245 (1984).
Maxwell et al., *Nature*, 399:271-275 (1999).
Richard, et al, "Nonhypoxic Pathway Mediates the Induction of Hypoxia-inducible Factor 1α in Vascular Smooth Muscle Cells", *J. Biol. Chm*, 275:26765-26771 (2000).
Safran, et al. "HIF hydroxylation and the mammalian oxygen-sensing pathway" *J. Clin. Invest.* 111(6):779-783 (2003).
Sandau, et al. "Induction of Hypoxia-Inducible-Factor 1 by Nitric Oxide Is Mediated via the P1 3K Pathway" *Biochem. Biophys. Res. Commun.*, 278:263-267(2000).
Sato et al. "Stability and Physicochemical Properties of Viracept Tablets" *Antibiotics and Chemotherapy* 14(9):1589-1592 (1998)—English Translation Not Available.
Sodhi, et al. "MAPK and Akt Act Cooperatively but Independently on Hypoxia Inducible Factor-1α in rasV12 Unpregulation of VEGF" *Biochem.Biophys. Res.Commun.*, 287:292-300 (2001).
Sutter et al., *Proc. Natl. Acad. Sci. USA*, 97:4748-4753 (2000).
Tacchini, et al. "Hepatocyte growth factor signaling stimulates hypoxia inducible factor-1 (HIF-1) activity in HepG2 hepatoma cells" *Carcinogenesis*, 22:1363-1371 (2001).
Tanimoto et al., *EMBO J*, 19:4298-4309 (2000).

CYANOISOQUINOLINE COMPOUNDS AND METHODS OF USE THEREOF

CROSS-REFERENCE TO RELATED APPLICATION

This application claims priority benefit under 35 U.S.C. §119 (e) of U.S. Provisional Application Ser. No. 60/762,780, filed Jan. 27, 2006, which is hereby incorporated by reference in its entirety.

BACKGROUND OF THE INVENTION

1. Field of the Invention

The present invention relates to methods and compounds capable of decreasing hypoxia inducible factor (HIF) hydroxylase enzyme activity, thereby increasing the stability and/or activity of HIF. In particular, the compounds increase endogenous erythropoietin, ex vivo and in vivo.

2. State of the Art

Hypoxia inducible factor (HIF) is a basic helix-loop-helix (bHLH) PAS (Per/Arnt/Sim) transcriptional activator that mediates changes in gene expression in response to changes in cellular oxygen concentration. HIF is a heterodimer containing an oxygen-regulated α-subunit (HIFα), and a constitutively expressed β-subunit (HIFβ), also known as aryl hydrocarbon receptor nuclear transporter (ARNT). In oxygenated (normoxic) cells, HIFα subunits are rapidly degraded by a mechanism that involves ubiquitination by the von Hippel-Lindau tumor suppressor (pVHL) E3 ligase complex. Under hypoxic conditions, HIFα is not degraded, and an active HIFα/β complex accumulates in the nucleus, and activates the expression of several genes including glycolytic enzymes, glucose transporters, erythropoietin (EPO), and vascular endothelial growth factor (VEGF). (Jiang, et al., (1996) J. Biol. Chem., 271:17771-17778; Iliopoulus, et al, (1996) Proc. Natl. Acad. Sci. USA, 93:10595-10599; Maxwell, et al., (1999), Nature, 399:271-275; Sutter, et al., (2000) Proc. Natl. Acad. Sci. USA, 97:4748-4753; Cockman, et al., (2000) J. Biol. Chem., 275:25733-25741; and Tanimoto, et al., (2000) EMBO. J. 19:4298-4309.)

Levels of HIFα are elevated in most cells in response to hypoxia, and HIFα is induced in vivo when animals are subjected to anemia or hypoxia. HIFα levels rise within a few hours after the onset of hypoxia, and induce numerous beneficial cellular processes including cytoprotective effects, enhanced erythropoiesis, and physiological adaptation to ischemic or hypoxic states. Induction of HIFα is potentially beneficial in conditions such as myocardial acute ischemia and early infarction, pulmonary hypertension, inflammation, and anemia.

HIFα levels are also increased by a number of factors that mimic hypoxia, including iron chelators such as desferrioxamine (DFO), and divalent metal salts such as $CoCl_2$. Additionally, compounds originally identified as inhibitors of procollagen prolyl hydroxylase enzymes have been found to stabilize HIFα. Examples of such compounds can be found, e.g., in Majamaa et al. (1984) Eur J Biochem 138:239-245; Majamaa et al. (1985) Biochem J 229:127-133; Kivirikko and Myllyharju (1998) Matrix Biol 16:357-368; Bickel et al. (1998) Hepatology 28:404-411; Friedman et al. (2000) Proc Natl Acad Sci USA 97:4736-4741; Franklin (1991) Biochem Soc Trans 19:812-815; and Franklin et al. (2001) Biochem J 353:333-338. Additionally, compounds that stabilize HIFα have been described in, e.g., International Publication Nos. WO 03/049686, WO 02/074981, WO 03/080566, WO 2004/108681, and WO 2006/094292.

There remains a need for compounds that are effective in the prevention of disorders associated with HIF, including anemia, and tissue damage caused by ischemia that occurs due to, e.g., atherosclerosis, diabetes, and pulmonary disorders such as pulmonary embolism, and the like. Thus, compounds that modulate HIF, which can be used to treat, and prevent HIF-associated disorders including conditions involving anemia, ischemia, and hypoxia, are provided herein.

SUMMARY OF THE INVENTION

The present invention is directed to novel compounds and methods of using the compounds to modulate hydroxylation of HIFα and/or increase endogenous erythropoietin (EPO). In particular, this invention is directed to isoquinoline compounds with a cyano group at the C-1 position, which compounds enhance the production of endogenous EPO (see, e.g., Table 1).

In one aspect, the invention provides compounds of formula I:

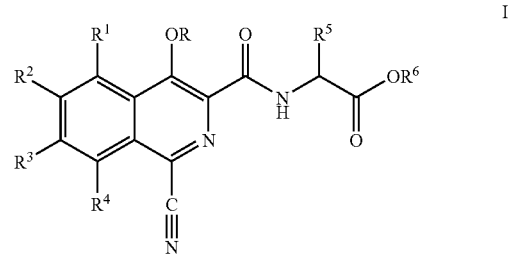

wherein:

R is selected from the group consisting of hydrogen, alkyl, and substituted alkyl;

$R^1$, $R^2$, $R^3$ and $R^4$ are independently selected from the group consisting of hydrogen, halo, cyano, hydroxyl, alkyl, substituted alkyl, aryl, substituted aryl, heteroaryl, substituted heteroaryl, amino, substituted amino, $-OR^7$, $-SR^7$, $-SOR^7$, and $-SO_2R^7$ wherein $R^7$ is selected from the group consisting of alkyl, substituted alkyl, cycloalkyl, substituted cycloalkyl, aryl, substituted aryl, heteroaryl, and substituted heteroaryl; and $R^5$ and $R^6$ are independently selected from the group consisting of hydrogen or $C_{1-3}$ alkyl;

or pharmaceutically acceptable salts, tautomers, stereoisomers, solvates, and/or prodrugs thereof.

In one embodiment, the invention is directed to compounds of formula Ia:

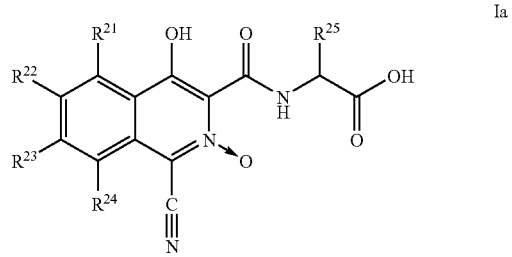

wherein:

q is 0 or 1;

$R^{21}$, $R^{22}$, $R^{23}$ and $R^{24}$ are independently selected from the group consisting of hydrogen, halo, hydroxy, alkyl, substituted alkyl, haloalkyl, alkoxy, substituted alkoxy, aryl, substituted aryl, aryloxy, substituted aryloxy, heteroaryl, substituted heteroaryl, heteroaryloxy, substituted heteroaryloxy, heterocyclyl, substituted heterocyclyl, heterocyclyloxy, amino, and substituted amino wherein at least two of $R^{21}$, $R^{22}$, $R^{23}$ and $R^{24}$ are hydrogen; and $R^{25}$ is selected from hydrogen or methyl;

or pharmaceutically acceptable salts, tautomers, stereoisomers, solvates, and/or prodrugs thereof.

In another aspect, the invention provides compounds of formula II:

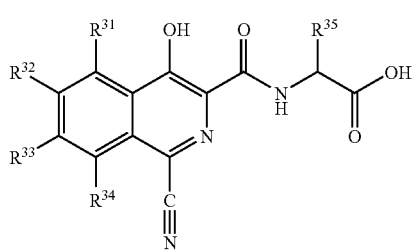

wherein:

$R^{31}$, $R^{32}$, $R^{33}$ and $R^{34}$ are independently selected from the group consisting of hydrogen, halo, hydroxyl, alkyl, substituted alkyl, aryl, substituted aryl, heteroaryl, substituted heteroaryl, amino, substituted amino, —$OR^{37}$, —$SR^{37}$, —$SOR^{37}$, and —$SO_2R^{37}$ wherein $R^{37}$ is selected from the group consisting of alkyl, substituted alkyl, cycloalkyl, substituted cycloalkyl, aryl, substituted aryl, heteroaryl, and substituted heteroaryl; and $R^{35}$ is hydrogen or methyl;

or pharmaceutically acceptable salts, tautomers, stereoisomers, solvates, and/or prodrugs thereof.

In one embodiment, the invention is directed to compounds of formula II, wherein $R^{31}$, $R^{32}$, $R^{33}$ and $R^{34}$ are independently selected from the group consisting of hydrogen, halo, hydroxy, alkyl, substituted alkyl, haloalkyl, alkoxy, substituted alkoxy, aryl, substituted aryl, aryloxy, substituted aryloxy, heteroaryl, substituted heteroaryloxy, cycloaryloxy, substituted cycloaryloxy, amino, and substituted amino; and $R^{35}$ is hydrogen or methyl;

or pharmaceutically acceptable salts, tautomers, stereoisomers, solvates, and/or prodrugs thereof.

In some embodiments, the invention provides compounds of formula II wherein at least three of $R^{31}$, $R^{32}$, $R^{33}$, and $R^{34}$ are hydrogen.

The invention also provides pharmaceutical compositions comprising one or more compounds of formula I, and/or II, and a pharmaceutically acceptable excipient. In some embodiments, the composition further comprises at least one additional therapeutic agent. In some embodiments, the agent is selected from the group consisting of vitamin B12, ferrous sulfate, folic acid, and/or erythropoietin or an erythropoiesis stimulating protein (ESP).

The invention is also directed to methods of inhibiting the activity of at least one HIF hydroxylase enzyme, the method comprising bringing into contact the HIF hydroxylase enzyme and an inhibitory-effective amount of a compound of the invention. In one embodiment, the HIF hydroxylase enzyme is an asparaginyl hydroxylase such as Factor Inhibiting HIF (FIH). In another embodiment, the HIF hydroxylase enzyme is a prolyl hydroxylase including, but not limited to, a HIF prolyl hydroxylase selected from the group consisting of human EGLN1, EGLN2, or EGLN3, or an orthologous enzyme from another species.

The invention is also directed to methods of treating, pre-treating, or delaying onset of a condition associated with or mediated at least in part by hypoxia inducible factor (HIF), the method comprising administering to a patient a therapeutically effective amount of a compound of formula I and/or II or a pharmaceutical composition produced therefrom. In one embodiment, the condition associated with or mediated by HIF is tissue damage associated with ischemia or hypoxia. In one aspect, the ischemia is an acute ischemic event including, but not limited to, an acute ischemic event selected from the group consisting of myocardial infarction, pulmonary embolism, intestinal infarction, ischemic stroke, and renal ischemic-reperfusion injury. In another aspect, the ischemia is a chronic ischemic event including, but not limited to, a chronic ischemic event selected from the group consisting of cardiac cirrhosis, macular degeneration, chronic kidney failure, and congestive heart failure.

The invention is also directed to methods of treating, pre-treating, or delaying onset of a condition associated with or mediated at least in part by erythropoietin (EPO), the method comprising administering to a patient a therapeutically effective amount of a compound of formula I and/or II or a pharmaceutical composition produced therefrom.

The invention is also directed to methods of treating, pre-treating, or delaying onset of anemia, the method comprising administering to a patient a therapeutically effective amount of a compound of formula I and/or II or a pharmaceutical composition produced therefrom.

DETAILED DESCRIPTION OF THE INVENTION

Before the present compositions and methods are described, it is to be understood that the invention is not limited to the particular methodologies, protocols, cell lines, assays, and reagents described, as these may vary. It is also to be understood that the terminology used herein is intended to describe particular embodiments of the present invention, and is in no way intended to limit the scope of the present invention as set forth in the appended claims.

A. Compounds of the Invention

The present invention provides compounds represented by formula I:

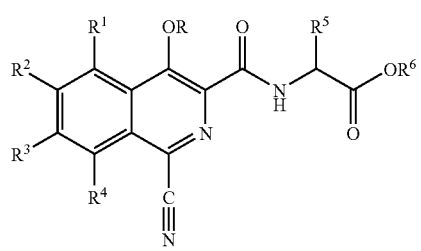

wherein:

R is selected from the group consisting of hydrogen, alkyl, and substituted alkyl;

$R^1$, $R^2$, $R^3$ and $R^4$ are independently selected from the group consisting of hydrogen, halo, cyano, hydroxyl, alkyl, substituted alkyl, aryl, substituted aryl, heteroaryl, substituted heteroaryl, amino, substituted amino, —$OR^7$, —$SR^7$, —$SOR^7$, and —$SO_2R^7$ wherein $R^7$ is selected from the group consisting of alkyl, substituted alkyl, cycloalkyl, substituted cycloalkyl, aryl, substituted aryl, heteroaryl, and substituted heteroaryl; and $R^5$ and $R^6$ are independently selected from the group consisting of hydrogen or $C_{1-3}$ alkyl;

or pharmaceutically acceptable salts, tautomers, stereoisomers, solvates, and/or prodrugs thereof.

In some embodiments, the invention provides compounds of formula I wherein at least two of $R^1$, $R^2$, $R^3$ and $R^4$ are hydrogen.

In some embodiments, the invention provides compounds of formula I wherein the nitrogen in the isoquinoline ring is N-oxide.

In some embodiments, $R^1$, $R^2$, $R^3$, and $R^4$ are independently selected from the group consisting of hydrogen, hydroxyl, halo, substituted alkyl including haloalkyl and trifluoromethyl, aryl, —$OR^7$—$SR^7$, and —$S_2R^7$ wherein $R^7$ is selected from the group consisting of alkyl, substituted alkyl, cycloalkyl, aryl, substituted aryl, heteroaryl, and substituted heteroaryl. In particular embodiments, $R^1$, $R^2$, $R^3$, and $R^4$ are selected from the group consisting of hydrogen, hydroxyl, phenyl, chloro, trifluoromethyl, benzyl, benzyloxy, methoxy, butoxy, isopropoxy, phenoxy, 4-fluorophenoxy, 2-methoxyphenoxy, 3-methoxyphenoxy, 4-methoxyphenoxy, 2,6-dimethylphenoxy, 2-ethyl-6-methylphenoxy, 2,4,6-trimethylphenoxy, 4-chloro-2,6-dimethylphenoxy, 4-propoxyphenoxy, 2,3-dihydro-benzofuran-5-yloxy, 2-methyl-benzothiazol-6-yloxy, 2-dimethylamino-benzooxazol-5-yloxy, 2-morpholin-4-yl-benzothiazol-6-yloxy, 2-methyl-benzooxazol-6-yloxy, benzo[1,3]dioxo-5-yloxy, phenylsulfanyl, phenylsulfonyl, and cyclohexyloxy.

In some embodiments, $R^1$, $R^2$, $R^3$, and $R^4$ are selected from hydrogen, halo, haloalkyl, alkyl, alkoxy, aryloxy and substituted aryloxy. In particular embodiments, $R^1$, $R^2$, $R^3$, and $R^4$ are selected from hydrogen, chloro, methoxy, trifluoromethyl, phenoxy, and 4-fluorophenoxy.

In some embodiments, $R^1$ and $R^2$ are hydrogen. In other embodiments $R^3$ and $R^4$ are hydrogen. In other embodiments $R^2$ and $R^3$ are hydrogen. In other embodiments, $R^1$ and $R^4$ are hydrogen. In other embodiments, $R^1$, $R^2$, $R^3$, and $R^4$ are hydrogen.

In still other embodiments, $R^2$, $R^3$, and $R^4$ are hydrogen. In particular embodiments wherein $R^2$, $R^3$, and $R^4$ are hydrogen, $R^1$ is phenyl, phenoxy or 4-fluorophenoxy.

In still other embodiments, $R^1$, $R^2$, and $R^4$ are hydrogen. In some embodiments $R^3$ is selected from the group consisting of hydroxyl, halo, haloalkyl, substituted alkyl, —$OR^7$, —$SR^7$, —$SOR^7$, and —$SO_2R^7$ wherein $R^7$ is selected from the group consisting of alkyl, substituted alkyl, aryl, substituted aryl, heteroaryl, and substituted heteroaryl. In particular embodiments, $R^3$ is selected from the group consisting of trifluoromethyl, chloro, hydroxyl, benzyl, methoxy, isopropoxy, butoxy, benzyloxy, phenoxy, 4-fluorophenoxy, 2,6-dimethylphenoxy, 4-methoxyphenoxy, 2-dimethylamino-benzooxazol-5-yloxy, benzo[1,3]dioxo-5-yloxy, and phenylsulfanyl. In certain embodiments wherein $R^1$, $R^2$, and $R^4$ are hydrogen, $R^3$ is phenoxy, 4-fluorophenoxy, trifluoromethyl, or chloro.

In still other embodiments, $R^1$, $R^2$, and $R^3$ are hydrogen. In some embodiments $R^4$ is selected from the group consisting of phenyl, phenoxy, 2-methoxyphenoxy, 3-methoxyphenoxy, 4-methoxyphenoxy, and 4-fluorophenoxy. In certain embodiments wherein $R^1$, $R^2$, and $R^3$ are hydrogen, $R^4$ is phenoxy or 4-fluorophenoxy.

In some embodiments $R^1$, $R^3$ and $R^4$ are hydrogen. In some embodiments, $R^2$ is selected from the group consisting of halo, cyano, hydroxyl, alkyl, substituted alkyl, aryl, substituted aryl, heteroaryl, substituted heteroaryl, amino, substituted amino, —$OR^7$, —$SR^7$, —$SOR^7$, and —$SO_2R^7$ wherein $R^7$ is selected from the group consisting of alkyl, substituted alkyl, cycloalkyl, substituted cycloalkyl, aryl, substituted aryl, heteroaryl, and substituted heteroaryl. In particular embodiments, $R^2$ is selected from the group consisting of halo, —$OR^7$, —$SR^7$, —$SOR^7$, and —$SO_2R^7$ wherein $R^7$ is selected from the group consisting of alkyl, substituted alkyl, cycloalkyl, aryl, substituted aryl, heteroaryl, and substituted heteroaryl. In certain embodiments, $R^2$ is selected from the group consisting of chloro, methoxy, isopropoxy, phenoxy, 4-fluorophenoxy, 4-methoxyphenoxy, 2,6-dimethylphenoxy, 2-ethyl-6-methylphenoxy, 2,4,6-trimethylphenoxy, 4-chloro-2,6-dimethylphenoxy, 4-propoxyphenoxy, 2,3-dihydro-benzofuran-5-yloxy, 2-methyl-benzothiazol-6-yloxy, 2-dimethylamino-benzooxazol-5-yloxy, 2-morpholin-4-yl-benzothiazol-6-yloxy, 2-methyl-benzooxazol-6-yloxy, benzo[1,3]dioxo-5-yloxy, phenylsulfonyl, phenylsulfanyl, and cyclohexyloxy. In certain embodiments wherein, $R^1$, $R^3$, and $R^4$ are hydrogen, $R^2$ is methoxy, phenoxy, or 4-fluorophenoxy.

In some embodiments, $R^5$ is hydrogen. In other embodiments, $R^5$ is methyl.

In some embodiments, $R^6$ is hydrogen. In other embodiments, $R^6$ is methyl.

In some embodiments, R is hydrogen. In other embodiments, R is methyl.

In one aspect, the invention provides compounds of formula II:

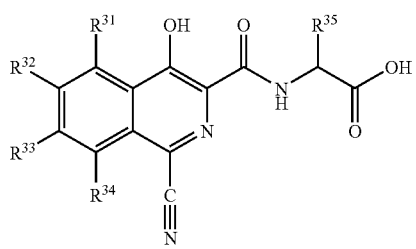

wherein:

$R^{31}$, $R^{32}$, $R^{33}$ and $R^{34}$ are independently selected from the group consisting of hydrogen, cyano, hydroxyl, halo, alkyl, substituted alkyl, aryl, substituted aryl, heteroaryl, substituted heteroaryl, amino, substituted amino, —$OR^{37}$, —$SR^{37}$—$SOR^{37}$, and —$SO_2R^{37}$ wherein $R^{37}$ is selected from the group consisting of alkyl, substituted alkyl, cycloalkyl, substituted cycloalkyl, aryl, substituted aryl, heteroaryl, and substituted heteroaryl; and $R^{35}$ is hydrogen or methyl;

or pharmaceutically acceptable salts, tautomers, stereoisomers, solvates, and/or prodrugs thereof.

In some embodiments, the invention provides compounds of formula II wherein at least three of $R^{31}$, $R^{32}$, $R^{33}$, and $R^{34}$ are hydrogen.

In one embodiment, the invention is directed to compounds of formula II, wherein $R^{31}$, $R^{32}$, $R^{33}$ and $R^{34}$ are independently selected from the group consisting of hydrogen, halo, hydroxy, alkyl, substituted alkyl, haloalkyl, alkoxy, substituted alkoxy, aryl, substituted aryl, aryloxy, substituted aryloxy, heteroaryloxy, substituted heteroaryloxy, cyclalkoxy, substituted cycloalkoxy, amino, and substituted amino; and $R^{35}$ is hydrogen or methyl;

or pharmaceutically acceptable salts, tautomers, stereoisomers, solvates, and/or prodrugs thereof.

In another embodiment, the invention is directed to compounds of formula II, wherein $R^{31}$, $R^{32}$, $R^{33}$ and $R^{34}$ are independently selected from the group consisting of hydrogen, substituted alkyl, aryl, aryloxy, and substituted aryloxy; and $R^{35}$ is hydrogen;

or pharmaceutically acceptable salts, tautomers, stereoisomers, solvates, and/or prodrugs thereof.

Compounds of the invention include, but are not limited to, the following compounds: {[1-cyano-4-hydroxy-isoquinoline-3-carbonyl]-amino}-acetic acid, 2-(S)-[(1-cyano-4-hydroxy-isoquinoline-3-carbonyl)-amino]-propionic acid, {[1-cyano-4-hydroxy-7-phenoxy-isoquinoline-3-carbonyl]-amino}-acetic acid, 2-(S)-[(1-cyano-4-hydroxy-7-phenoxy-isoquinoline-3-carbonyl)-amino]-propionic acid, 2-(R)-[(1-cyano-4-hydroxy-7-phenoxy-isoquinoline-3-carbonyl)-amino]-propionic acid, {[1-cyano-7-(4-fluorophenoxy)-4-hydroxy-isoquinoline-3-carbonyl]-amino}-acetic acid, {[1-cyano-4-hydroxy-7-(trifluoromethyl)-isoquinoline-3-carbonyl]-amino}-acetic acid, {[1-cyano-4-hydroxy-7-chloro-isoquinoline-3-carbonyl]-amino}-acetic acid, {[1-cyano-4-hydroxy-8-phenoxy-isoquinoline-3-carbonyl]-amino}-acetic acid, {[1-cyano-8-(4-fluoro-phenoxy)-4-hydroxy-isoquinoline-3-carbonyl]-amino}-acetic acid, [(1-cyano-4-hydroxy-6-methoxy-isoquinoline-3-carbonyl)-amino]-acetic acid, [(1-cyano-4-hydroxy-6-phenoxy-isoquinoline-3-carbonyl)-amino]-acetic acid, {[1-cyano-6-(4-fluoro-phenoxy)-4-hydroxy-isoquinoline-3-carbonyl]-amino}-acetic acid, {[1-cyano-4-hydroxy-6-(4-methoxy-phenoxy)-isoquinoline-3-carbonyl]-amino}-acetic acid, [(1-cyano-4-hydroxy-6-phenylsulfanyl-isoquinoline-3-carbonyl)-amino]-acetic acid, [(1-cyano-4-hydroxy-7-phenylsulfanyl-isoquinoline-3-carbonyl)-amino]-acetic acid, {[1-cyano-6-(2,6-dimethyl-phenoxy)-4-hydroxy-isoquinoline-3-carbonyl]-amino}-acetic acid, [(1-cyano-4-hydroxy-5-phenoxy-isoquinoline-3-carbonyl)-amino]-acetic acid, {[1-cyano-4-hydroxy-8-(4-methoxy-phenoxy)-isoquinoline-3-carbonyl]-amino}-acetic acid, {[1-cyano-4-hydroxy-8-(3-methoxy-phenoxy)-isoquinoline-3-carbonyl]-amino}-acetic acid, {[1-cyano-4-hydroxy-8-(2-methoxy-phenoxy)-isoquinoline-3-carbonyl]-amino}-acetic acid, [(7-benzyl-1-cyano-4-hydroxy-isoquinoline-3-carbonyl)-amino]-acetic acid, {[1-cyano-5-(4-fluoro-phenoxy)-4-hydroxy-isoquinoline-3-carbonyl]-amino}-acetic acid, {[1-cyano-7-(2,6-dimethyl-phenoxy)-4-hydroxy-isoquinoline-3-carbonyl]-amino}-acetic acid, {[1-cyano-6-(2-ethyl-6-methyl-phenoxy)-4-hydroxy-isoquinoline-3-carbonyl]-amino}-acetic acid, {[1-cyano-4-hydroxy-6-(2,4,6-trimethyl-phenoxy)-isoquinoline-3-carbonyl]-amino}-acetic acid, {[6-(4-chloro-2,6-dimethyl-phenoxy)-1-cyano-4-hydroxy-isoquinoline-3-carbonyl]-amino}-acetic acid, {[1-cyano-4-hydroxy-7-(4-methoxy-phenoxy)-isoquinoline-3-carbonyl]-amino}-acetic acid, [(1-cyano-6-cyclohexyloxy-4-hydroxy-isoquinoline-3-carbonyl)-amino]-acetic acid, [(6-benzenesulfonyl-1-cyano-4-hydroxy-isoquinoline-3-carbonyl)-amino]-acetic acid, {[1-cyano-4-hydroxy-6-(4-propoxy-phenoxy)-isoquinoline-3-carbonyl]-amino}-acetic acid, {[7-(benzo[1,3]dioxol-5-yloxy)-1-cyano-4-hydroxy-isoquinoline-3-carbonyl]-amino}-acetic acid, {[6-(benzo[1,3]dioxol-5-yloxy)-1-cyano-4-hydroxy-isoquinoline-3-carbonyl]-amino}-acetic acid, {[1-cyano-6-(2,3-dihydro-benzofuran-5-yloxy)-4-hydroxy-isoquinoline-3-carbonyl]-amino}-acetic acid, [(1-cyano-4-methoxy-8-phenoxy-isoquinoline-3-carbonyl)-amino]-acetic acid methyl ester, [(1-cyano-4-methoxy-8-phenoxy-isoquinoline-3-carbonyl)-amino]-acetic acid, (S)-2-[(1-cyano-4-hydroxy-8-phenoxy-isoquinoline-3-carbonyl)-amino]-propionic acid, (R)-2-[(1-cyano-4-hydroxy-8-phenoxy-isoquinoline-3-carbonyl)-amino]-propionic acid, {[1-cyano-4-hydroxy-6-(2-methyl-benzothiazol-6-yloxy)-isoquinoline-3-carbonyl]-amino}-acetic acid, {[1-cyano-6-(2-dimethylamino-benzooxazol-5-yloxy)-4-hydroxy-isoquinoline-3-carbonyl]-amino}-acetic acid, {[1-cyano-7-(2-dimethylamino-benzooxazol-5-yloxy)-4-hydroxy-isoquinoline-3-carbonyl]-amino}-acetic acid, {[1-cyano-4-hydroxy-6-(2-morpholin-4-yl-benzothiazol-6-yloxy)-isoquinoline-3-carbonyl]-amino}-acetic acid, {[1-cyano-4-hydroxy-6-(2-methyl-benzooxazol-6-yloxy)-isoquinoline-3-carbonyl]-amino}-acetic acid, [(6-chloro-1-cyano-4-hydroxy-isoquinoline-3-carbonyl)-amino]-acetic acid, [(7-butoxy-1-cyano-4-hydroxy-isoquinoline-3-carbonyl)-amino]-acetic acid, [(1-cyano-4-hydroxy-6,7-diphenoxy-isoquinoline-3-carbonyl)-amino]-acetic acid, [(1-cyano-4-hydroxy-7-methoxy-isoquinoline-3-carbonyl)-amino]-acetic acid, [(1-cyano-4-hydroxy-7-isopropoxy-isoquinoline-3-carbonyl)-amino]-acetic acid, [(1-cyano-4-hydroxy-6-isopropoxy-isoquinoline-3-carbonyl)-amino]-acetic acid, [(1-cyano-4-hydroxy-5-phenyl-isoquinoline-3-carbonyl)-amino]-acetic acid, [(1-cyano-4-hydroxy-8-phenyl-isoquinoline-3-carbonyl)-amino]-acetic acid, [(7-benzyloxy-1-cyano-4-hydroxy-isoquinoline-3-carbonyl)-amino]-acetic acid, and [(1-cyano-4,7-dihydroxy-isoquinoline-3-carbonyl)-amino]-acetic acid.

It will be self-evident to the skilled person that many of the embodiments described above are not mutually exclusive, and may be combined to provide further specific embodiments of the invention. Such specific embodiments are explicitly envisaged herein. Similarly, the dependent claims may be made dependent on any preceding claim, provided that the embodiments described are not mutually exclusive.

B. Definitions

It must be noted that as used herein and in the appended claims, the singular forms "a," "an," and "the" include plural references unless the context clearly dictates otherwise.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications cited herein are incorporated herein by reference in their entirety for the purpose of describing and disclosing the methodologies, reagents, and tools reported in the publications that might be used in connection with the invention. Nothing herein is to be construed as an admission that the invention is not entitled to antedate such disclosure by virtue of prior invention.

The practice of the present invention will employ, unless otherwise indicated, conventional methods of chemistry, biochemistry, molecular biology, cell biology, genetics, immunology and pharmacology, within the skill of the art. Such techniques are explained fully in the literature. (See, e.g., Gennaro, A. R., ed. (1990) Remington's Pharmaceutical Sciences, 18$^{th}$ ed., Mack Publishing Co.; Colowick, S. et al., eds., Methods In Enzymology, Academic Press, Inc.; D. M. Weir, and C. C. Blackwell, eds. (1986) Handbook of Experimental Immunology, Vols. I-IV (Blackwell Scientific Publications); Maniatis, T. et al., eds. (1989) Molecular Cloning: A Laboratory Manual, $2^{nd}$ edition, Vols. I-III, Cold Spring Harbor Laboratory Press; Ausubel, F. M. et al., eds. (1999) Short Protocols in Molecular Biology, $4^{th}$ edition, John Wiley & Sons; Ream et al., eds. (1998) Molecular Biology Techniques: An Intensive Laboratory Course, Academic Press; Newton & Graham eds., 1997 PCR (Introduction to Biotechniques Series), 2nd ed. (Springer Verlag).

The term "anemia" as used herein refers to any abnormality in hemoglobin or erythrocytes that leads to reduced oxygen levels in the blood. Anemia can be associated with abnormal production, processing, or performance of erythrocytes and/or hemoglobin. The term anemia refers to any reduction in the number of red blood cells and/or level of hemoglobin in blood relative to normal blood levels.

Anemia can arise due to conditions such as acute or chronic kidney disease, infections, inflammation, cancer, irradiation, toxins, diabetes, and surgery. Infections may be due to, e.g., virus, bacteria, and/or parasites, etc. Inflammation may be due to infection or autoimmune disorders, such as rheumatoid arthritis, etc. Anemia can also be associated with blood loss due to, e.g., stomach ulcer, duodenal ulcer, hemorrhoids, cancer of the stomach or large intestine, trauma, injury, surgical procedures, etc. Anemia is further associated with radiation therapy, chemotherapy, and kidney dialysis. Anemia is also associated with HIV-infected patients undergoing treatment with azidothymidine (zidovudine) or other reverse transcriptase inhibitors, and can develop in cancer patients undergoing chemotherapy, e.g., with cyclic cisplatin- or non-cisplatin-containing chemotherapeutics. Aplastic anemia and myelodysplastic syndromes are diseases associated with bone marrow failure that result in decreased production of erythrocytes. Further, anemia can result from defective or abnormal hemoglobin or erythrocytes, such as in disorders including microcytic anemia, hypochromic anemia, etc. Anemia can result from disorders in iron transport, processing, and utilization, see, e.g., sideroblastic anemia, etc.

The terms "disorders," "diseases," and "conditions" are used inclusively and refer to any condition deviating from normal.

The terms "anemic conditions" and "anemic disorders" refer to any condition, disease, or disorder associated with anemia. Such disorders include, but are not limited to, those disorders listed above. Anemic disorders further include, but are not limited to, aplastic anemia, autoimmune hemolytic anemia, bone marrow transplantation, Churg-Strauss syndrome, Diamond Blackfan anemia, Fanconi's anemia, Felty syndrome, graft versus host disease, hematopoietic stem cell transplantation, hemolytic uremic syndrome, myelodysplastic syndrome, nocturnal paroxysmal hemoglobinuria, osteomyelofibrosis, pancytopenia, pure red-cell aplasia, purpura Schoenlein-Henoch, sideroblastic anemia, refractory anemia with excess of blasts, rheumatoid arthritis, Shwachman syndrome, sickle cell disease, thalassemia major, thalassemia minor, thrombocytopenic purpura, etc.

The term "erythropoietin-associated conditions" is used inclusively and refers to any condition associated with below normal, abnormal, or inappropriate modulation of erythropoietin. Erythropoietin-associated conditions include any condition wherein an increase in EPO level would provide therapeutic benefit. Levels of erythropoietin associated with such conditions can be determined by any measure accepted and utilized by those of skill in the art. Erythropoietin-associated conditions include anemic conditions such as those described above.

Erythropoietin-associated conditions further include neurological disorders and/or injuries, including cases of stroke, trauma, epilepsy, neurodegenerative disease and the like, wherein erythropoietin may provide a neuroprotective effect. Neurodegenerative diseases contemplated by the invention include Alzheimer's disease, Parkinson's disease, Huntington's disease, and the like.

The term "erythropoietin" refers to any recombinant or naturally occurring erythropoietin or ESP including, e.g., human erythropoietin (GenBank Accession No. AAA52400; Lin et al. (1985) Proc Nat'l Acad. Sci. USA 82:7580-7584), EPOETIN human recombinant erythropoietin (Amgen, Inc., Thousand Oaks Calif.), ARANESP human recombinant erythropoietin (Amgen), PROCRIT human recombinant erythropoietin (Ortho Biotech Products, L. P., Raritan N.J.), glycosylated erythropoietin such as those described in U.S. Pat. No. 6,930,086 (which is incorporated by reference), etc.

The term "HIFα" refers to the alpha subunit of hypoxia inducible factor protein. HIFα may be any human or other mammalian protein, or fragment thereof, including human HIF-1α (Genbank Accession No. Q16665), HIF-2α (Genbank Accession No. AAB41495), and HIF-3α (Genbank Accession No. AAD22668); murine HIF-1α (Genbank Accession No. Q61221), HIF-2α (Genbank Accession No. BAA20130 and AAB41496), and HIF-3α (Genbank Accession No. AAC72734); rat HIF-1α (Genbank Accession No. CAA70701), HIF-2α (Genbank Accession No. CAB96612), and HIF-3α (Genbank Accession No. CAB96611); and bovine HIF-1α (Genbank Accession No. BAA78675). HIFα may also be any non-mammalian protein or fragment thereof, including *Xenopus laevis* HIF-1α (Genbank Accession No. CAB96628), *Drosophila melanogaster* HIF-1α (Genbank Accession No. JC4851), and chicken HIF-1α (Genbank Accession No. BAA34234). HIFα gene sequences may also be obtained by routine cloning techniques, for example by using all or part of a HIFα gene sequence described above as a probe to recover and determine the sequence of a HIFα gene in another species.

A fragment of HIFα includes any fragment retaining at least one functional or structural characteristic of HIFα. Fragments of HIFα include, e.g., the regions defined by human HIF-1α from amino acids 401 to 603 (Huang et al., supra), amino acid 531 to 575 (Jiang et al. (1997) J. Biol. Chem. 272:19253-19260), amino acid 556 to 575 (Tanimoto et al., supra), amino acid 557 to 571 (Srinivas et al. (1999) Biochem Biophys Res. Commun 260:557-561), and amino acid 556 to 575 (Ivan and Kaelin (2001) Science 292:464-468). Further, HIFα fragments include any fragment containing at least one occurrence of the motif LXXLAP. (See Genbank Accession No. Q16665.)

The term "fragment" can refer to any portion of a sequence that retains at least one structural or functional characteristic of the protein. Fragments are of any length but preferably are of about 5 to 100 amino acids in length, particularly of about 15 to 50 amino acids in length, and more particularly of about 20 amino acids in length. Where "amino acid sequence" is used to refer to the polypeptide sequence of a naturally occurring protein molecule, "amino acid sequence" and like terms are not meant to limit the amino acid sequence to the complete native sequence associated with the recited protein molecule.

The term "related proteins" as used herein, for example, to refer to proteins related to HIFα prolyl hydroxylase, encompasses other 2-oxoglutarate dioxygenase enzymes, especially those family members that similarly require $Fe^{2+}$, 2-oxoglutarate, and oxygen to maintain hydroxylase activity. Such enzymes include, but are not limited to, e.g., procollagen lysyl hydroxylase, procollagen prolyl 4-hydroxylase, and Factor Inhibiting HIF (FIH), an asparaginyl hydroxylase responsible for regulating transactivation of HIFα. (GenBank Accession No. AAL27308; Mahon et al. (2001) Genes Dev 15:2675-2686; Lando et al. (2002) Science 295:858-861; and Lando et al. (2002) Genes Dev 16:1466-1471. See also Elkins et al. (2002) J Biol Chem C200644200, etc.).

The term "HIF hydroxylase" refers to any enzyme that modifies the alpha subunit of HIF by hydroxylation of one or more amino acid residues. HIF hydroxylases include Factor Inhibiting HIF (FIH) (GenBank Accession AAL27308; Mahon et al. (2001) Genes Dev 15:2675-2686; Lando et al. (2002) Science 295:858-861; and Lando et al. (2002) Genes Dev 16:1466-1471, which modifies at least one asparagine residue found within HIFα. (Also, see, Elkins et al. (2002) J Biol Chem C200644200.) HIF hydroxylases also include HIF prolyl hydroxylases (HIF PHs), which modify proline residues found within HIFα.

The terms "HIF prolyl hydroxylase" and "HIF PH" refer to any enzyme capable of hydroxylating a proline residue in the HIF protein. Preferably, the proline residue hydroxylated by HIF PH includes the proline found within the motif LXXLAP. HIF PH includes members of the Egl-Nine (EGLN) gene family described by Taylor (2001, Gene 275:125-132), and characterized by Aravind and Koonin (2001, Genome Biol 2: RESEARCH 0007), Epstein et al. (2001, Cell 107:43-54), and Bruick and McKnight (2001, Science 294:1337-1340). Examples of HIF PH enzymes include human SM-20 (EGLN1) (GenBank Accession No. AAG33965; Dupuy et al (2000) Genomics 69:348-54), EGLN2 isoform 1 (GenBank Accession No. CAC42510; Taylor, supra), EGLN2 isoform 2 (GenBank Accession No. NP_060025), and EGLN3 (GenBank Accession No. CAC42511; Taylor, supra); mouse EGLN1 (GenBank Accession No. CAC42515), EGLN2 (GenBank Accession No. CAC42511), and EGLN3 (SM-20) (GenBank Accession No. CAC42517); and rat SM-20 (GenBank Accession No. AAA19321). Additionally, HIF PH may include *Caenorhabditis elegans* EGL-9 (GenBank Accession No. AAD56365) and *Drosophila melanogaster* CG1114 gene product (GenBank Accession No. AAF52050). HIF PH also includes any portion of the foregoing full-length proteins that retain at least one structural or functional characteristic.

The term "excipient" as used herein means an inert or inactive substance used in the production of pharmaceutical products or other tablets, including without limitation any substance used as a binder, disintegrant, coating, compression/encapsulation aid, cream or lotion, lubricant, parenteral, sweetener or flavoring, suspending/gelling agent, or wet granulation agent. Binders include, e.g., carbopol, povidone, xanthan gum, etc.; coatings include, e.g., cellulose acetate phthalate, ethylcellulose, gellan gum, maltodextrin, etc.; compression/encapsulation aids include, e.g., calcium carbonate, dextrose, fructose dc, honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams and lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; parenterals include, e.g., mannitol, povidone, etc.; plasticizers include, e.g., dibutyl sebacate, polyvinylacetate phthalate, etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

The term "subject" is used herein in its broadest sense. Subjects may include isolated cells, either prokaryotic or eukaryotic, or tissues grown in culture. In certain embodiments, a subject is an animal, particularly an animal selected from a mammalian species including rat, rabbit, bovine, ovine, porcine, canine, feline, murine, equine, and primate, particularly human.

The term "alkyl" refers to monovalent hydrocarbyl groups having from 1 to 10 carbon atoms, more particularly from 1 to 5 carbon atoms, and even more particularly 1 to 3 carbon atoms. This term is exemplified by groups such as methyl, ethyl, n-propyl, iso-propyl, n-butyl, t-butyl, n-pentyl and the like.

The term "substituted alkyl" refers to an alkyl group, of from 1 to 10 carbon atoms, particularly 1 to 5 carbon atoms, having from 1 to 5 substituents, more particularly 1 to 3 substituents, each of which is independently selected from the group consisting of alkyl, alkoxy, substituted alkoxy, acyl, acylamino, acyloxy, amino, substituted amino, aminoacyl, aminocarbonylamino, aminothiocarbonylamino, aminocarbonyloxy, aryl, substituted aryl, aryloxy, substituted aryloxy, cyano (—CN), halogen, hydroxyl (—OH), nitro (—NO$_2$), oxo (=O), thioxo (=S), carboxyl, carboxyl esters, cycloalkyl, substituted cycloalkyl, thiol, alkylthio, substituted alkylthio, arylthio, substituted arylthio, cycloalkylthio, substituted cycloalkylthio, heteroarylthio, substituted heteroarylthio, heterocyclicthio, substituted heterocyclicthio, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, OS(O)$_2$-heteroaryl, —OS(O)$_2$-substituted heteroaryl, —OS(O)$_2$-heterocyclic, —OS(O)$_2$-substituted heterocyclic, —NR$^{40}$S(O)$_2$-alkyl, —NR$^{40}$S(O)$_2$-substituted alkyl, —NR$^{40}$S(O)$_2$-aryl, —NR$^{40}$S(O)$_2$-substituted aryl, —NR$^{40}$S(O)$_2$-heteroaryl, —NR$^{40}$S(O)$_2$-substituted heteroaryl, —NR$^{40}$S(O)$_2$-heterocyclic, —NR$^{40}$S(O)$_2$-substituted heterocyclic, —OSO$_2$—NR$^{40}$R$^{40}$, —NR$^{40}$S(O)$_2$—NR$^{40}$-alkyl, —NR$^{40}$S(O)$_2$—NR$^{40}$-substituted alkyl, —NR$^{40}$S(O)$_2$—NR$^{40}$-aryl, —NR$^{40}$S(O)$_2$—NR$^{40}$-substituted aryl, —NR$^{40}$S(O)$_2$—NR$^{40}$-heteroaryl, —NR$^{40}$S(O)$_2$—NR$^{40}$-substituted heteroaryl, —NR$^{40}$S(O)$_2$—NR$^{40}$-heterocyclic, and —NR$^{40}$S(O)$_2$—NR$^{40}$-substituted heterocyclic where each R$^{40}$ is independently selected from hydrogen or alkyl.

The term "haloalkyl" refers to an alkyl group substituted with from 1 to 5, and particularly 1 to 3 halogen atoms. Preferably, the halogen atom is fluoro or chloro. Suitable haloalkyl moieties include, but are not limited to, —CF$_3$, —CH$_2$CF$_3$.

The term "alkoxy" refers to the group "alkyl-O—" which includes, by way of example, methoxy, ethoxy, n-propoxy, iso-propoxy, n-butoxy, t-butoxy, sec-butoxy, n-pentoxy and the like.

The term "substituted alkoxy" refers to the group "substituted alkyl-O—".

The term "acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, heteroaryl-C(O)—, substituted heteroaryl-C(O), heterocyclic-C(O)—, and substituted heterocyclic-C(O)— provided that a nitrogen atom of the heterocyclic or substituted heterocyclic is not bound to the —C(O)— group wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

The term "aminoacyl" and the prefix "carbamoyl" or "carboxamide" or "substituted carbamoyl" or "substituted carboxamide" refer to the group —C(O)NR$^{42}$R$^{42}$ where each R$^{42}$ is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic and substituted heterocyclic; or where each R$^{42}$ is joined to form together with the nitrogen atom a heterocyclic or substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

The term "acyloxy" refers to the moiety —O-acyl, wherein the oxygen atom is attached to the carbonyl (—C(O)) of the acyl moiety.

The term "alkenyl" refers to a vinyl unsaturated monovalent hydrocarbyl group having from 2 to 6 carbon atoms and preferably 2 to 4 carbon atoms, and having at least 1, and preferably from 1 to 2 sites of vinyl (>C=C<) unsaturation. Such groups are exemplified by vinyl (ethen-1-yl), allyl, but-3-enyl and the like.

The term "substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic. This term includes both E (cis) and Z (trans) isomers as appropriate. It also includes mixtures of both E and Z components.

The term "alkynyl" refers to an acetylinic unsaturated monovalent hydrocarbyl groups having from 2 to 6 carbon atoms and preferably 2 to 3 carbon atoms and having at least 1, and preferably from 1 to 2 sites of acetylenic (—C≡C—) unsaturation. This group is exemplified by ethyn-1-yl, propyn-1-yl, propyn-2-yl, and the like.

The term "substituted alkynyl" refers to alkynyl groups having from 1 to 3 substituents, and preferably 1 to 2 substituents, selected from those listed for substituted alkenyl.

The term "amino" refers to the group —NH$_2$.

The term "substituted amino" refers to the group —NR$^{41}$R$^{41}$, where each R$^{41}$ is independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, substituted heterocyclic, —SO$_2$-alkyl, —SO$_2$-substituted alkyl, —SO$_2$-alkenyl, —SO$_2$-substituted alkenyl, —SO$_2$-cycloalkyl, —SO$_2$-substituted cycloalkyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic, provided that both R$^{41}$ groups are not hydrogen; or the R$^{41}$ groups can be joined together with the nitrogen atom to form a heterocyclic or substituted heterocyclic ring.

The term "acylamino" refers to the group —NR$^{45}$C(O) alkyl, —NR$^{45}$C(O)substituted alkyl, —NR$^{45}$C(O)cycloalkyl, —NR$^{45}$C(O)substituted cycloalkyl, —NR$^{45}$C(O) alkenyl, —NR$^{45}$C(O)substituted alkenyl, —NR$^{45}$C(O) alkynyl, —NR$^{45}$C(O)substituted alkynyl, —NR$^{45}$C(O)aryl, —NR$^{45}$C(O)substituted aryl, —NR$^{45}$C(O)heteroaryl, —NR$^{45}$C(O)substituted heteroaryl, —NR$^{45}$C(O)heterocyclic, and —NR$^{45}$C(O)substituted heterocyclic where R$^{45}$ is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are defined herein.

The term "carbonyloxyamino" refers to the groups —NR$^{46}$C(O)O-alkyl, —NR$^{46}$C(O)O-substituted alkyl, —NR$^{46}$C(O)O-alkenyl, —NR$^{46}$C(O)O-substituted alkenyl, —NR$^{46}$C(O)O-alkynyl, —NR$^{46}$C(O)O-substituted alkynyl, —NR$^{46}$C(O)O-cycloalkyl, —NR$^{46}$C(O)O-substituted cycloalkyl, —NR$^{46}$C(O)O-aryl, —NR$^{46}$C(O)O-substituted aryl, —NR$^{46}$C(O)O-heteroaryl, —NR$^{46}$C(O)O-substituted heteroaryl, —NR$^{46}$C(O)O-heterocyclic, and —NR$^{46}$C(O)O-substituted heterocyclic where R$^{46}$ is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein. It should be understood that the group "oxycarbonylamino" refers to groups similar to those just described except that the attachment of the oxygen and carbonyl (—C(=O)—) group are switched. Also, the term "oxythiocarbonylamino" are similar to those just described; however, a thiocarbonyl (—C(=S)—) is used in place of a carbonyl.

The term "aminocarbonyloxy" or as a prefix "carbamoyloxy" or "substituted carbamoyloxy" refers to the groups —OC(O)NR$^{47}$R$^{47}$ where each R$^{47}$ is independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic; or where each R$^{47}$ is joined to form, together with the nitrogen atom a heterocyclic or substituted heterocyclic and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

The term "aminocarbonylamino" refers to the group —NR$^{49}$C(O)NR$^{49}$ where each R$^{49}$ is independently selected from the group consisting of hydrogen and alkyl. The term "aminothiocarbonylamino" refers to the moiety —NR$^{49}$C(S) R$^{49}$—, wherein R$^{49}$ is as defined above.

The term "aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3 (4H)-one-7-yl, and the like) provided that the point of attachment is the aryl group. Preferred aryls include phenyl and naphthyl.

The term "substituted aryl" refers to aryl groups, as defined herein, which are substituted with from 1 to 4, preferably 1 to 3, substituents selected from those listed for substituted alkyl with the exception that such substitution does not include oxo or thioxo.

The term "aryloxy" refers to the group aryl-O— that includes, by way of example, phenoxy, naphthoxy, and the like.

The term "substituted aryloxy" refers to substituted aryl-O— groups.

The term "aryloxyaryl" refers to the group -aryl-O-aryl.

The term "substituted aryloxyaryl" refers to aryloxyaryl groups substituted with from 1 to 3 substituents on either or both aryl rings as defined above for substituted aryl.

The term "carboxyl" refers to —COOH or salts thereof.

The term "carboxyl esters" or "alkoxycarbonyl" refers to the groups —C(O)O-alkyl, —C(O)O-substituted alkyl, —C(O)O-aryl, and —C(O)O-substituted aryl wherein alkyl, substituted alkyl, aryl and substituted aryl are as defined herein.

The term "cycloalkyl" refers to cyclic alkyl groups of from 3 to 10 carbon atoms having single or multiple cyclic rings including, by way of example, adamantyl, cyclopropyl, cyclobutyl, cyclopentyl, cyclooctyl and the like.

The term "substituted cycloalkyl" refers to a cycloalkyl group, having from 1 to 5 substituents selected from those listed for substituted alkyl.

The term "cycloalkoxy" refers to —O-cycloalkyl groups.

The term "substituted cycloalkoxy" refers to —O-substituted cycloalkyl groups.

The term "halo" or "halogen" refers to fluoro, chloro, bromo and iodo and preferably is fluoro or chloro.

The term "heteroaryl" refers to an aromatic group of from 1 to 15 carbon atoms, preferably from 1 to 10 carbon atoms, and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl, benzothienyl, 2-benzoxazolinone-2H-1,4-benzoxazin-3(4H)-one-7-yl, benzofuran, 2,3-dihydrobenzofuran, benzothiazole, benzooxazole, benzo[1,3]dioxolyl, and the like). Preferred heteroaryls include pyridinyl, pyrrolyl, indolyl, thiophenyl, and furyl.

The term "substituted heteroaryl" refers to heteroaryl groups that are substituted with from 1 to 3 substituents selected from the same group of substituents defined for substituted aryl.

The term "heteroaryloxy" refers to the group —O-heteroaryl and "substituted heteroaryloxy" refers to the group —O-substituted heteroaryl.

The term "heterocycle" or "heterocyclic," or "heterocyclyl" refers to a saturated or unsaturated group having a single ring or multiple condensed rings, from 1 to 10 carbon atoms and from 1 to 4 hetero atoms selected from the group consisting of nitrogen, sulfur or oxygen within the ring wherein, in fused ring systems, one or more the rings can be aryl or heteroaryl provided that the point of attachment is at the heterocycle.

The term "substituted heterocyclic" or "substituted heterocyclyl" refers to heterocycle groups that are substituted with from 1 to 3 of the same substituents as defined for substituted cycloalkyl.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydro-isoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), piperidinyl, pyrrolidine, tetrahydrofuranyl, and the like.

The term "heterocyclyloxy" refers to the group —O-heterocyclic and "substituted heterocyclyloxy" refers to the group —O-substituted heterocyclic.

The term "thiol" refers to the group —SH.

The term "alkylthio" refer to the groups —S-alkyl where alkyl is as defined above.

The term "substituted alkylthio" and "substituted alkylsulfanyl" refer to the group —S-substituted alkyl, where substituted alkyl is as defined above.

The term "cycloalkylthio" or "cycloalkylsulfanyl" refers to the groups —S-cycloalkyl where cycloalkyl is as defined above.

The term "substituted cycloalkylthio" refers to the group —S-substituted cycloalkyl where substituted cycloalkyl is as defined above.

The term "arylthio" or "arylsulfanyl" refers to the group —S-aryl and "substituted arylthio" refers to the group —S-substituted aryl where aryl and substituted aryl are as defined above.

The term "heteroarylthio" refers to the group —S-heteroaryl and "substituted heteroarylthio" refers to the group —S-substituted heteroaryl where heteroaryl and substituted heteroaryl are as defined above.

The term "heterocyclicthio" refers to the group —S-heterocyclic and "substituted heterocyclicthio" refers to the group —S-substituted heterocyclic where heterocyclic and substituted heterocyclic are as defined above.

The term "pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

The term "prodrug," refers to compounds of formula I, and/or II of this invention that include chemical groups which, in vivo, can be converted into the carboxylate group on the amino-acid side chain of the compounds and/or can be converted into the amide carbonyl group and/or can be split off from the amide N-atom and/or can be split off from the 4-O atom of the isoquinoline and/or can be converted into the 1-cyano group and/or can be split off from the N-atom of the isoquinoline ring to provide for the active drug, a pharmaceutically acceptable salt thereof or a biologically active metabolite thereof. Suitable groups are well known in the art and particularly include: for the carboxylic acid moiety on the glycine or alanine substituent, a prodrug selected from, e.g., esters including, but not limited to, those derived from alkyl alcohols, substituted alkyl alcohols, hydroxy substituted aryls and heteroaryls and the like; amides, particularly amides derived from amines of the formula $HNR^{20}R^{21}$ where $R^{20}$ and $R^{21}$ are independently hydrogen, alkyl, substituted alkyl, aryl, substituted aryl, and the like; hydroxymethyl, aldehyde and derivatives thereof; and for the isoquinoline N atom, a prodrug selected from, e.g., N-oxides and N-alkyl derivatives.

The term "solvates," refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water.

The term "tautomer" refers to alternate forms of a molecule that differ in the position of a proton, such as enol-ketol and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that, for example, substituted aryl groups are limited to -substituted aryl-(substituted aryl)-substituted aryl.

Similarly, it is understood that the above definitions are not intended to include impermissible substitution patterns (e.g., methyl substituted with 5 fluoro groups or a hydroxyl group alpha to ethenylic or acetylenic unsaturation). Such impermissible substitution patterns are well known to the skilled artisan.

C. Compositions and Methods of the Invention

The invention provides for use of a compound of formula I and/or II for the manufacture of a medicament for use in treating various conditions or disorders as described herein. In one embodiment, a pharmaceutical composition is provided comprising a pharmaceutically acceptable excipient or carrier, and a therapeutically effective amount of at least one compound of formula I and/or II.

The medicament or composition can further comprise at least one additional therapeutic agent selected from the group including, but not limited to, vitamin $B_{12}$, ferrous sulfate, folic acid, and/or recombinant erythropoietin or an erythropoiesis stimulating protein (ESP).

The compounds of the present invention, or medicaments or compositions comprising the compounds, can be used to modulate the stability and/or activity of HIF, and thereby activate HIF-regulated gene expression. The compound, or composition or medicament thereof, can be used in methods to treat, pretreat, or delay progression or onset of conditions associated with HIF including, but not limited to, anemic, ischemic, and hypoxic conditions. In various embodiments, the compound is administered immediately following a condition producing acute ischemia, e.g., myocardial infarction, pulmonary embolism, intestinal infarction, ischemic stroke, and renal ischemic-reperfusion injury. In another embodiment, the compound, or composition or medicament thereof, is administered to a patient diagnosed with a condition associated with the development of chronic ischemia, e.g., cardiac cirrhosis, macular degeneration, pulmonary embolism, acute respiratory failure, neonatal respiratory distress syndrome, and congestive heart failure. In yet another embodiment, the compound, or composition or medicament thereof, is administered immediately after a trauma or injury. In other embodiments, the compound, or composition or medicament thereof, can be administered to a subject based on predisposing conditions, e.g., hypertension, diabetes, occlusive arterial disease, chronic venous insufficiency, Raynaud's disease, chronic skin ulcers, cirrhosis, congestive heart failure, and systemic sclerosis. In still other embodiments, compounds may be administered to pretreat a subject to decrease or prevent the development of tissue damage associated with ischemia or hypoxia.

The compounds of the present invention, or compositions or medicaments thereof, can also be used to increase endogenous erythropoietin (EPO). The compounds, or composition or medicament thereof, can be administered to prevent, pretreat, or treat EPO-associated conditions, including, e.g., conditions associated with anemia and neurological disorders. Conditions associated with anemia include disorders such as acute or chronic kidney disease, diabetes, cancer, ulcers, infection with virus, e.g., HIV, bacteria, or parasites; inflammation, etc. Anemic conditions can further include those associated with procedures or treatments including, e.g., radiation therapy, chemotherapy, dialysis, and surgery. Disorders associated with anemia additionally include abnormal hemoglobin and/or erythrocytes, such as found in disorders such as microcytic anemia, hypochromic anemia, aplastic anemia, etc.

The compounds can be used to increase endogenous EPO in a subject undergoing a specific treatment or procedure, prophylactically or concurrently, for example, an HIV-infected anemic patient being treated with azidothymidine (zidovudine) or other reverse transcriptase inhibitors, an anemic cancer patient receiving cyclic cisplatin- or non-cisplatin-containing chemotherapeutics, or an anemic or non-anemic patient scheduled to undergo surgery. Additionally, the compounds can be used to increase endogenous EPO levels in an anemic or non-anemic patient scheduled to undergo surgery to reduce the need for allogenic blood transfusions or to facilitate banking of blood prior to surgery.

The invention is also directed to use of a compound, or composition or medicament thereof, to treat, pretreat, or delay onset of a condition associated with a disorder selected from the group consisting of anemic disorders; neurological disorders and/or injuries including cases of stroke, trauma, epilepsy, and neurodegenerative disease; cardiac ischemia including, but not limited to, myocardial infarction and congestive heart failure; liver ischemia including, but not limited to, cardiac cirrhosis; renal ischemia including, but not limited to, acute kidney failure and chronic kidney failure; peripheral vascular disorders, ulcers, burns, and chronic wounds; pulmonary embolism; and ischemic-reperfusion injury.

The invention is also directed to a method of inhibiting the activity of at least one hydroxylase enzyme which modifies the alpha subunit of hypoxia inducible factor. The HIF hydroxylase enzyme may be an asparaginyl hydroxylase such as Factor Inhibiting HIF (FIH); and/or a prolyl hydroxylase including, but not limited to, the group consisting of EGLN1, EGLN2, and EGLN3. The method comprises contacting the enzyme with an inhibiting effective amount of one or more compounds selected from the group comprising compounds of formula I and/or II.

D. Synthesis of Compounds of the Invention

The compounds of this invention can be prepared from readily available starting materials using the following general methods and procedures. It will be appreciated that where typical or preferred process conditions (i.e., reaction temperatures, times, mol ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis*, Third Edition, Wiley, New York, 1999, and references cited therein.

Furthermore, the compounds of this invention may contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989), Organic Reactions, Volumes 1-40 (John Wiley, and Sons, 1991), March's Advanced Organic Chemistry, (John Wiley, and Sons, 5$^{th}$ Edition, 2001), and Larock's Comprehensive Organic Transformations (VCH Publishers Inc., 1989).

The isoquinolines 300, 1000, and 1100 of this invention can be prepared by the synthetic protocols illustrated in Scheme 1.

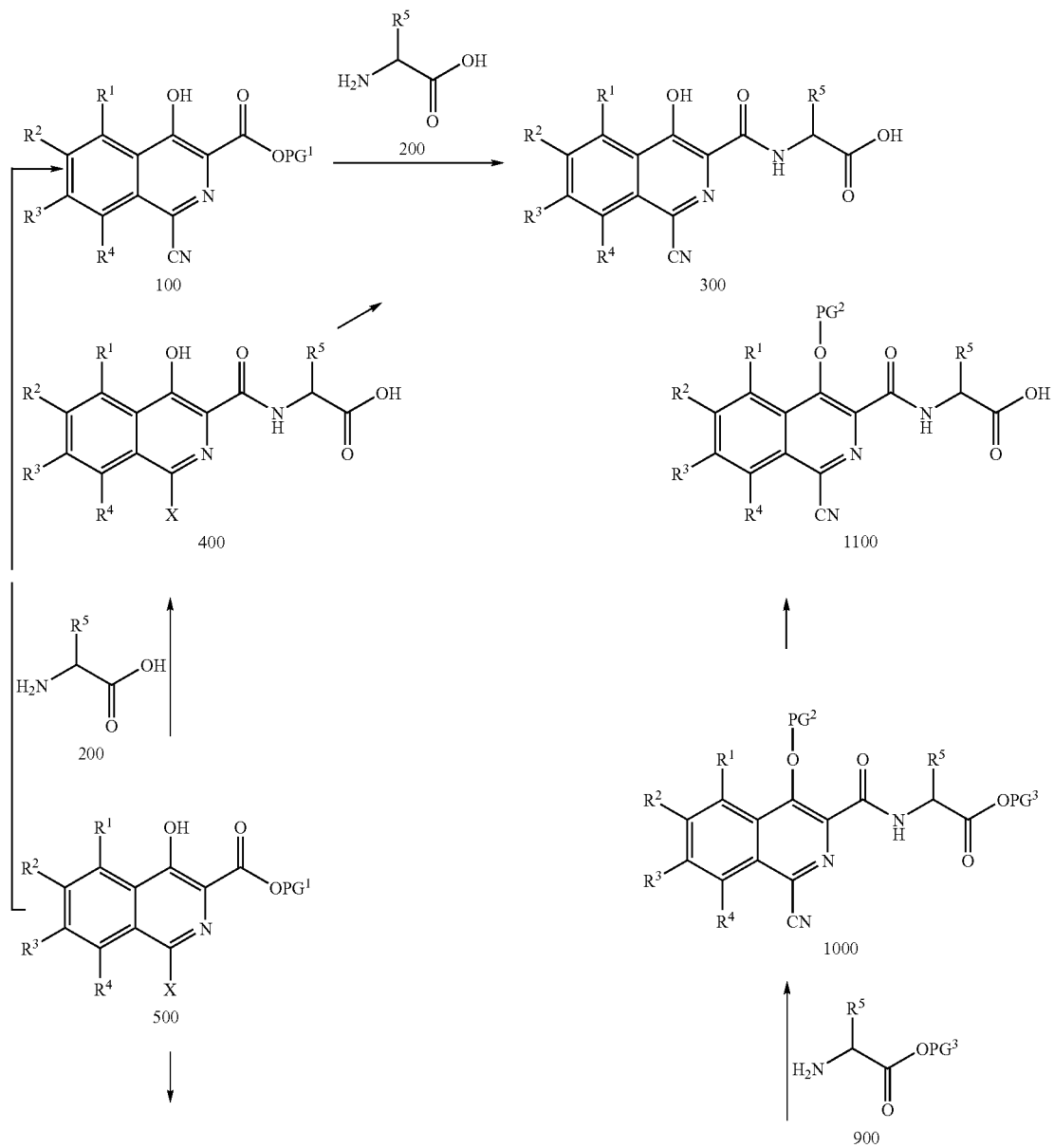

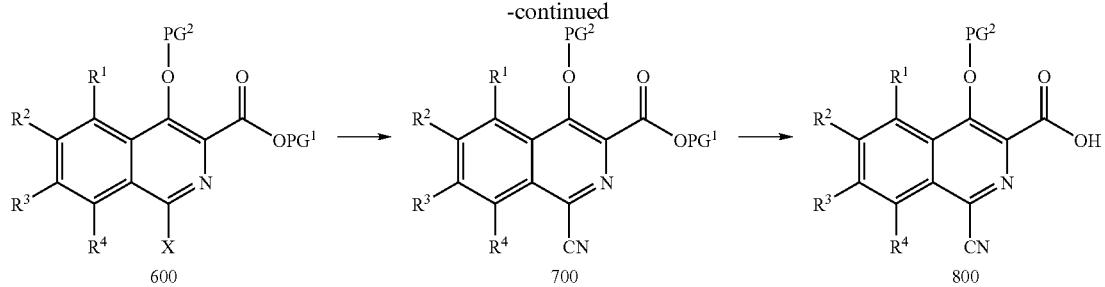

$R^1$, $R^2$, $R^3$, $R^4$, and $R^5$ are as defined herein. Compound 100 (wherein $PG^1$ refers to a suitable protecting group such as methyl, ethyl, butyl, etc.) are reacted with at least a stoichiometric amount and preferably an excess of a suitable alpha-amino acid, compound 200 (particularly, but not limited to, glycine). The reaction is conducted under conventional coupling conditions well known in the art. In one embodiment, the reaction is conducted in the presence of sodium methoxide or another suitable base in methanol or another suitable solvent under elevated reaction temperatures and particularly at reflux. The reaction is continued until it is substantially complete which typically occurs within about 1 to 72 h. Alternatively, the reaction can be performed at elevated temperatures in a microwave oven. Upon reaction completion, the compound 300 can be recovered by conventional techniques such as neutralization, extraction, precipitation, chromatography, filtration and the like.

Alternatively, coupling of compound 100 (typically as the corresponding free acid) with compound 200 (typically as ester derivatives) can proceed via conventional peptide coupling procedures well known in the art. This coupling reaction is typically conducted using well-known coupling reagents such as carbodiimides, BOP reagent (benzotriazol-1-yloxytris(dimethylamino)-phosphonium hexafluorophosphonate) and the like. Suitable carbodiimides include, by way of example, dicyclohexylcarbodiimide (DCC), 1-(3-dimethylamino-propyl)-3-ethylcarbodiimide (DECI) and the like. If desired, polymer supported forms of carbodiimide coupling reagents may also be used including, for example, those described in *Tetrahedron Letters*, 34(48), 7685 (1993). Additionally, well-known coupling promoters, such as N-hydroxysuccinimide, 1-hydroxybenzotriazole and the like, may be used to facilitate the coupling reaction. This coupling reaction is typically conducted by contacting the corresponding free acids of compound 100 with about 1 to about 2 equivalents of the coupling reagent and at least one equivalent, preferably about 1 to about 1.2 equivalents, of an ester of compound 200, in an inert diluent such as dichloromethane, chloroform, acetonitrile, tetrahydrofuran, N,N-dimethylformamide and the like. Generally, this reaction is conducted at a temperature ranging from about 0° C. to about 37° C. for about 12 to about 24 hours. Upon completion of the reaction, the corresponding ester of compound 300 is recovered by conventional methods including neutralization, extraction, precipitation, chromatography, filtration, and the like, and is then transformed into compound 300 by hydrolysis.

Alternatively, compound 100 (typically as the corresponding free acid) can be converted into an acid halide and the acid halide coupled with the ester of compound 200 to provide for the esters of compound 300. The acid halide of compound 100 can be prepared by contacting compound 100 (typically as the corresponding free acid) with an inorganic acid halide such as thionyl chloride, phosphorous trichloride, phosphorous tribromide, or phosphorous pentachloride, or, particularly, with oxalyl chloride under conventional conditions. Generally, this reaction is conducted using about 1 to 5 molar equivalents of the inorganic acid halide or oxalyl chloride, either neat or in an inert solvent such as dichloromethane or carbon tetrachloride, at temperature in the range of about 0° C. to about 80° C. for about 1 to about 48 hours. A catalyst, such as DMF, may also be used in this reaction.

The acid halide (not shown) is then contacted with at least one equivalent, preferably about 1.1 to about 1.5 equivalents, of an ester of compound 200, in an inert diluent such as dichloromethane, at a temperature ranging from about −70° C. to about 40° C. for about 1 to about 24 hours. Preferably, this reaction is conducted in the presence of a suitable base to scavenge the acid generated during the reaction. Suitable bases include, by way of example, tertiary amines such as triethylamine, diisopropylethylamine, N-methyl-morpholine, and the like. Alternatively, the reaction can be conducted under Schotten-Baumann-type conditions using aqueous alkali such as sodium hydroxide and the like. Upon completion of the reaction, the ester of compound 300 is recovered by conventional methods including neutralization, extraction, precipitation, chromatography, filtration, and the like, and is then transformed into compound 300 by hydrolysis.

Compound 100 may be obtained by cyanation of compound 500 (wherein X is Cl, Br, or I; and $PG^1$ refers to a suitable protecting group such as methyl, ethyl, butyl, etc.) with a suitable cyanide source such as, by way of example, CuCN, $Zn(CN)_2$, etc. The cyanation may occur in the presence of a suitable catalyst such as, by way of example, palladium catalyst such as tris(dibenzylideneacetone)dipalladium (0) (see, e.g., Sundermeier et al. (2003) Eur. J. Inorg. Chem. 2003(19):3513-3526) and/or additives using a suitable solvent such as, by way of example, DMF or N,N-dimethylacetamide. Upon reaction completion, compound 100 can be recovered by conventional techniques such as neutralization, extraction, precipitation, chromatography, filtration and the like; or, alternatively, used in the next step without purification and/or isolation. Compound 100 obtained by this method may be further altered by modifying its $R^1$, $R^2$, $R^3$, and/or $R^4$ moieties, e.g., if $R^3$ is $OCH_2Ph$, the $R^3$ moiety can be transformed into OH using conventional reduction techniques (particularly by hydrogenation catalyzed by palladium on carbon, etc.).

Alternatively, compound 400 (wherein X is selected from Cl, Br, or I) may be reacted with a suitable cyanide source such as, by way of example, CuCN, $Zn(CN)_2$, etc. to give compound 300. The cyanation may be carried out as described above. Upon reaction completion, compound 300 can be recovered by conventional techniques such as neutralization, extraction, precipitation, chromatography, filtration and the like; or, alternatively, used in the next step without purification and/or isolation. Compound 400 may be obtained by reaction between compound 500 (wherein X is selected from Cl, Br, or I; and PG¹ refers to a suitable protecting group such as methyl, ethyl, butyl, etc.) and compound 200 in analogy to the corresponding reactions between compound 100 and compound 200 (Scheme 1; also, see U.S. Pat. No. 6,093, 730 and U.S. Patent Application Publication No. 2006/217416, which is hereby incorporated by reference).

Alternatively, the 4-hydroxy group of compound 500 can be alkylated with suitable reagents such as, by way of example, alkyl halides, alkyl sulfates, benzyl halides, diazo compounds, etc. The alkylation may take place in the presence of suitable base such as $Cs_2CO_3$ and/or additives using a suitable solvent such as, by way of example, DMF to give compound 600 (wherein $PG^2$ is preferably but not limited to, methyl). Upon reaction completion, compound 600 can be recovered by conventional techniques such as neutralization, extraction, precipitation, chromatography, filtration and the like; or, alternatively, used in the next step without purification and/or isolation.

Compound 600 (wherein X is selected from Cl, Br, or I) can be reacted with a suitable cyanide source such as, by way of example, CuCN, $Zn(CN)_2$, etc., to give compound 700. The cyanation may be carried out as described above. Hydrolysis of compound 700 using conventional standard conditions provides compound 800. Upon reaction completion, compound 800 can be recovered by conventional techniques such as neutralization, extraction, precipitation, chromatography, filtration and the like; or, alternatively, used in the next step without purification and/or isolation.

Coupling of compound 800 with compound 900 (wherein $PG^3$ refers to a suitable protecting group such as methyl, ethyl, butyl, etc.; preformed or generated in situ from its salts by addition of a suitable base) can proceed via conventional peptide coupling procedures well known in the art and as described above. The coupling reaction is typically conducted by contacting compound 800 with about 1 to about 2 equivalents of the coupling reagent and at least one equivalent, preferably about 1 to about 1.2 equivalents, of compound 900, in an inert diluent such as dichloromethane, chloroform, acetonitrile, tetrahydrofuran, N,N-dimethylformamide and the like and, if required, in the presence of a suitable base. Generally, this reaction is conducted at a temperature ranging from about 0° C. to about 37° C. for about 12 to about 24 hours. Upon completion of the reaction, compound 1000 is recovered by conventional methods including neutralization, extraction, precipitation, chromatography, filtration, and the like, and can then be transformed into compound 1100 by hydrolysis.

Alternatively, compound 800 can be converted into an acid halide and the acid halide coupled with compound 900 to provide compound 1000. The acid halide of compound 800 can be prepared by contacting compounds 800 with an inorganic acid halide or with oxalyl chloride under conventional conditions, e.g., as described above. The acid halide (not shown) is then contacted with at least one equivalent, preferably about 1.1 to about 1.5 equivalents of compound 900 in an inert diluent such as dichloromethane, at a temperature ranging from about −70° C. to about 40° C. for about 1 to about 24 hours. Preferably, this reaction is conducted in the presence of a suitable base to scavenge the acid generated during the reaction. Suitable bases include tertiary amines such as triethylamine, diisopropylethylamine, N-methyl-morpholine, and the like. Alternatively, the reaction can be conducted under Schotten-Baumann-type conditions using aqueous alkali such as sodium hydroxide and the like. Upon completion of the reaction, compound 1000 is recovered by conventional methods including neutralization, extraction, precipitation, chromatography, filtration, and the like, and can then be transformed into compound 1100 by hydrolysis (Scheme 1).

Compound 500, for use in the reactions above, can be prepared according to synthetic routes as depicted in Scheme 2.

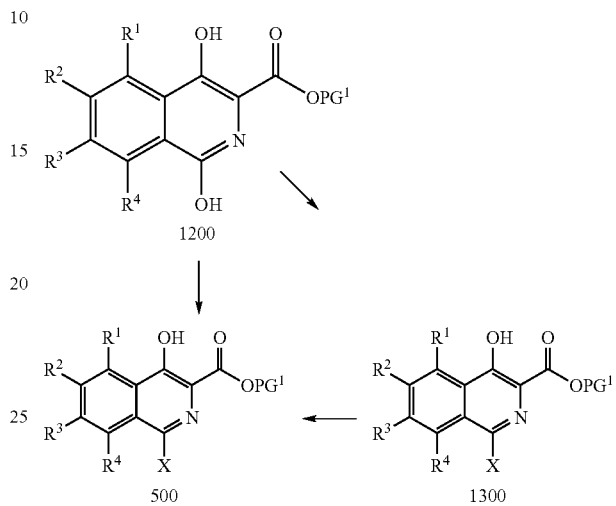

Scheme 2

$R^1$, $R^2$, $R^3$, and $R^4$ are as defined herein. Treatment of compound 1200 with phosphorous oxychloride or phosphorous oxybromide using a suitable solvent such as acetonitrile or toluene particularly at reflux temperature gives compound 500 wherein X is Cl or Br, respectively. The reaction typically occurs within about 1 to 72 h. Alternatively, the reaction can be performed at elevated temperatures in a microwave oven. Upon reaction completion, compound 500 can be recovered by conventional techniques such as neutralization, extraction, precipitation, chromatography, filtration and the like; or, alternatively, used in the next step without purification and/or isolation.

Alternatively, compound 1300 can be halogenated using conventional methods to give compound 500 wherein X is Cl, Br, or I. The halogenation of compound 1300 can be performed with a stoichiometric amount or slight excess of, e.g., N-bromosuccinimide in the presence of a catalytic amount of benzoylperoxide, azobisisobutyronitrile, or another suitable free radical initiator, in $CCl_4$, benzene, or another suitable solvent known to one skilled in the art typically at reflux temperature or higher temperatures using a microwave oven. Upon reaction completion, compounds 500 can be recovered by conventional techniques such as neutralization, extraction, precipitation, chromatography, filtration and the like; or, alternatively, used in the next step without purification and/or isolation. Alternatively, compound 1300 can be obtained by halogenating compound 1200 as described above followed by reduction using conventional methods such as hydrogenation catalyzed by palladium on carbon, etc.

The synthesis of substituted isoquinoline carboxylic acids are generally known in the art and are described by, for example, Weidmann, et al., U.S. Pat. No. 6,093,730, which is incorporated herein by reference in its entirety. Compound 1200, for use in the reactions above, can be obtained using the methods outlined in Scheme 3 (see US2006/217416, which is hereby incorporated by reference).

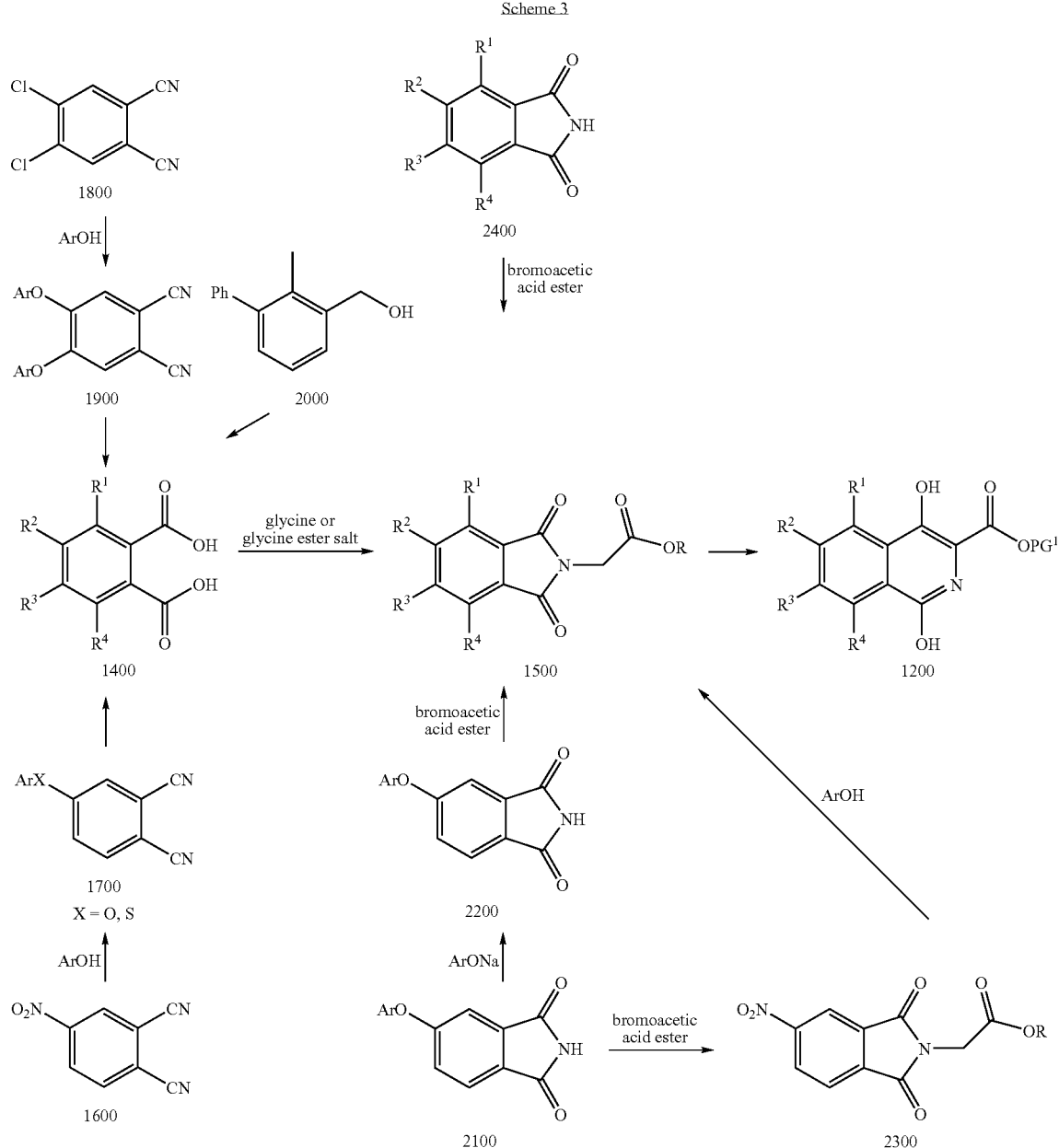

Scheme 3

$R^1$, $R^2$, $R^3$, and $R^4$ are as defined herein. Compound 1200 can be obtained from compound 1500 (particularly wherein R is methyl, ethyl, or butyl) by Gabriel-Colman rearrangement with a solution of 2 equivalents of sodium in an appropriate alcohol such as n-butanol at an elevated temperature of about 95-100° C. for about 1 to 4 h. Compound 1500 is either commercially available or are easily obtained by reacting the phthalic acid, compound 1400 or its derivatives (particularly the corresponding acid anhydrides) with an equimolar amount of glycine or salts of glycine esters (particularly hydrochloride salts of glycine methyl, ethyl or butyl ester) neat typically at 150 to 250° C. for 15 to 90 min until no water is released. If glycine is used, the product (R=H) is esterified using conventional methods, e.g., by refluxing in a suitable alcohol such as methanol or ethanol in the presence of a concentrated sulfuric acid, etc. Compound 1400 and its derivatives, e.g., the corresponding acid anhydrides, are either commercially available or are easily accessible by reacting compound 1600 with an excess of phenol ArOH in a suitable solvent such as, e.g., DMF, in the presence of a base such as, by example, an excess of potassium carbonate. The resulting compound 1700 is readily hydrolyzed by refluxing in a solution of KOH in water/methanol (typically 1 to 3 days) to give the compound 1400.

Alternatively, compound 1400 can be obtained by analogous methods from compound 1800. Reaction between compound 1800 and phenol ArOH provides compound 1900, which can be readily hydrolyzed to the corresponding phthalic acid, compound 1400. Biphenyl-2,3-dicarboxylic acid can be obtained by oxidation of compound 2000 with potassium permanganate in the presence of a phase transfer catalyst. Alternatively, compound 1500 can be obtained by reacting compound 2100 with an excess of a phenolate such as, by way of example, sodium phenolates ArONa, typically by heating in DMF. The resulting phthalimide, compound 2200, can be transformed to compound 1500 by N-alkylation with an excess of a haloacetic acid ester such as, by way of example, the methyl or ethyl esters of bromoacetic acid, using conventional methods such as refluxing in a suitable solvent such as acetone in the presence of a suitable base such as potassium carbonate. Compound 1500 can be obtained analogously by N-alkylation of commercially available phthalimides, compound 2400. Alternatively, compound 1500 can be obtained by N-alkylation of compound 2100 using methods as described above. The resulting compound 2300 can be transformed to compound 1500 by reaction with phenols ArOH in a suitable solvent, such as dimethylacetamide at 105° C., in the presence of a suitable base such as potassium carbonate. Alternatively, compound 1500 with a phenolic OH group can be transformed to the corresponding phenol ethers by O-alkylation using conventional methods such as, by way of example, refluxing with electrophiles such as methyl iodide (MeI), isopropyl iodide (iPrI), butyl iodide (BuI), etc. in the presence of a base or by alkylating the phenolic OH group with an alcohol such as cyclohexanol using a variant of the Mitsunobu reaction.

Compound 1300, for use in the reactions above, can be obtained using the methods outlined in Scheme 4 (see also US2006/217416).

without purification and/or isolation. Alternatively, compound 2700 with a phenolic OH group can be transformed to the corresponding phenol ethers by O-alkylation using conventional methods such as, by way of example, refluxing with electrophiles such as benzyl bromide, etc. in the presence of a base.

Compound 2700 wherein $PG^4$ is, e.g., 2,4-dimethoxybenzyl, can be cyclized to compound 2800 by treatment with a suitable base such as, by way of example, 2 equivalents of potassium tert-butoxide, in THF at 0° C. for about 1 h and then room temperature for about 3 h. Upon reaction completion, the resulting compound 2800 can be recovered by conventional techniques such as neutralization, extraction, precipitation, chromatography, filtration and the like; or, alternatively, used in the next step without purification and/or isolation. Compound 2800 is then treated with thionyl chloride, e.g., about 1.5 equivalents, in a suitable solvent such as dichloromethane at 0° C. for about 1 h and then room temperature for about 3 h. Upon reaction completion, the resulting compound 1300 can be recovered by conventional techniques such as neutralization, extraction, precipitation, chromatography, filtration and the like; or, alternatively, used in the next step without purification and/or isolation. Alternatively, compound 2700 wherein $PG^4$ is, e.g., toluene-4-sulfonyl, can be cyclized by treatment with a suitable base such as, by way of example, 3 to 4 equivalents of sodium methoxide in methanol at room temperature for 3 h to 3 d.

Scheme 4

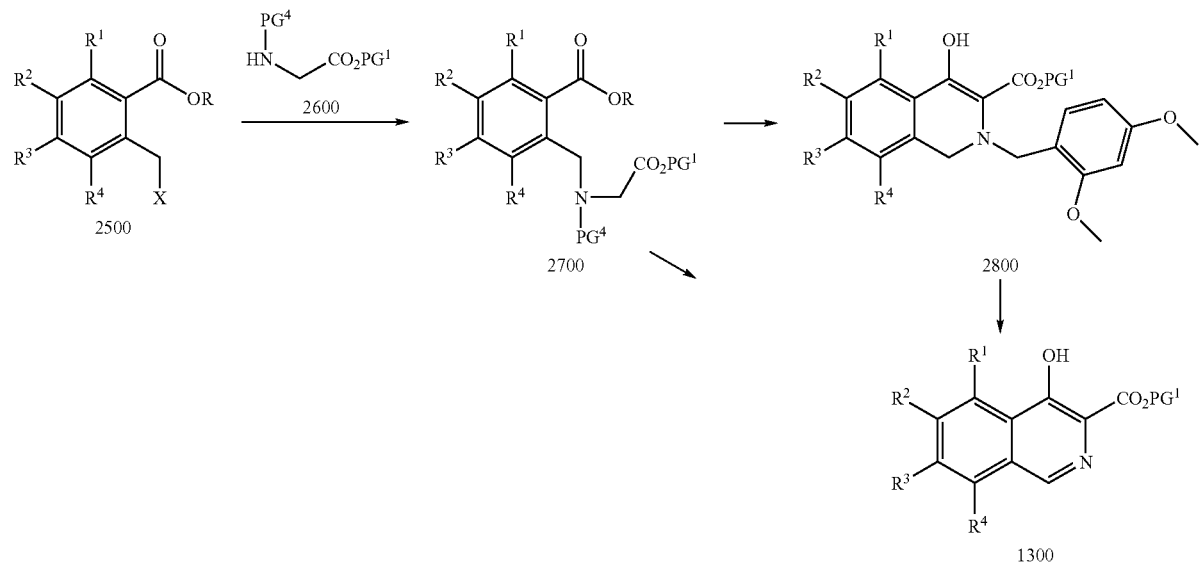

$R^1$, $R^2$, $R^3$, and $R^4$ are as defined herein. Compound 2500 (particularly wherein R is methyl or ethyl, and X is Cl, Br, or I; preformed or generated in situ by anion exchange using sodium iodide) is reacted with a protected glycine ester, compound 2600 (particularly wherein $PG^1$ is methyl or ethyl and $PG^4$ is toluene-4-sulfonyl or 2,4-dimethoxybenzyl) in the presence of a suitable base such as potassium carbonate, optionally in the presence of sodium iodide, in a suitable solvent such as DMF at, e.g., room temperature for about 2 to 24 h. Upon reaction completion, the resulting compound 2700 can be recovered by conventional techniques such as neutralization, extraction, precipitation, chromatography, filtration and the like; or, alternatively, used in the next step Upon reaction completion, the resulting compound 1300 can be recovered by conventional techniques such as neutralization, extraction, precipitation, chromatography, filtration and the like; or, alternatively, used in the next step without purification and/or isolation.

Compound 1300 can be further altered by modifying its $R^1$, $R^2$, $R^3$, and/or $R^4$ moieties. For example, $R^2$ is SPh then the $R^2$ moiety can be transformed into $SO_2Ph$ using conventional oxidation techniques such as, by way of example, treatment with m-chloroperoxybenzoic acid in methylenechloride at room temperature. Alternatively, if $R^4$ is, e.g., iodine, the iodine atom can be substituted with phenols ArOH such as, e.g., ortho-, metha-, and para-methoxyphenol, to give the corresponding 8-aryloxy isoquinolines by reacting the iodo-isoquinoline with ArOH, e.g., 5 equivalents in a suitable solvent such as DMF at reflux temperature in the presence of a suitable base, such as 5 equivalent of cesium carbonate, and a suitable catalyst, such as 1 equivalent of CuCl and 0.4 equivalents of 2,2,6,6-tetramethyl-heptane-3,5-dione, for about 15 min. Upon reaction completion, the resulting compound 1300 can be recovered by conventional techniques such as neutralization, extraction, precipitation, chromatography, filtration and the like; or, alternatively, used in the next step without purification and/or isolation.

Compound 2500, for use in the reactions described above, can be obtained using the methods outlined in Scheme 5 (see also US2006/217416).

extraction, precipitation, chromatography, filtration and the like; or, alternatively, used in the next step without purification and/or isolation.

Compound 3100 is accessible typically by reacting a mixture of the sodium salt of compound 2900, a slight excess of a sodium phenolate ArONa, a catalytic amount of copper bronze, and 1,2-dichlorobenzene at, e.g., reflux temperature for about 2 h. Upon reaction completion, compound 3000 can be recovered by conventional techniques such as neutralization, extraction, precipitation, chromatography, filtration and the like; or, alternatively, used in the next step without purification and/or isolation. Compounds 3000 and 3200 are easily converted to the corresponding esters, compounds 3100 and 3300, respectively, using conventional methods such as

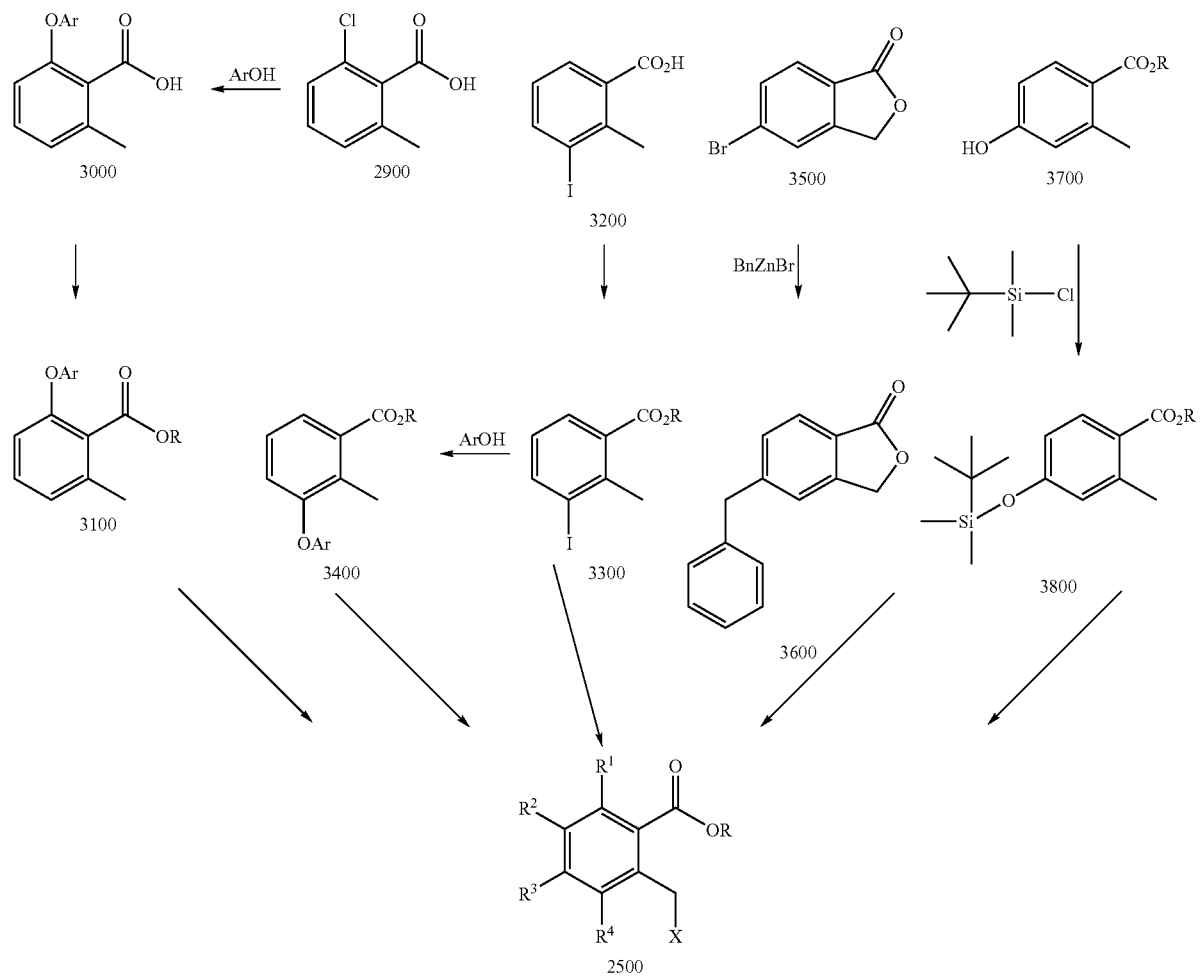

Scheme 5

$R^1$, $R^2$, $R^3$, and $R^4$ are as defined herein. Compound 2500, particularly ortho-toluic acid esters such as 3100, 3300, 3400, or 3800 wherein R is, e.g., methyl or ethyl, can be halogenated, by way of example, by addition of a stoichiometric amount or a slight excess of N-bromosuccinimide in the presence of a catalytic amount of benzoylperoxide, azobisisobutyronitrile, or another suitable free radical initiator in $CCl_4$, benzene or another suitable solvent at, e.g., reflux temperature. Upon reaction completion, compound 2500 can be recovered by conventional techniques such as neutralization, refluxing in a suitable alcohol such as methanol or ethanol in the presence of concentrated sulfuric acid; or refluxing together with an alkylating reagent such as dimethylsulfate in the presence of a base such as potassium carbonate in a suitable solvent such as diethylketone. Compound 3400 can be obtained by adding compound 3300, an excess of phenol, an excess of cesium carbonate, and an excess of 1-naphthoic acid, molecular sieves, a catalytic amount of ethyl acetate, and an appropriate solvent such as anhydrous toluene to a catalytic amount of copper(I) trifluoromethanesulfonate-benzene complex at room temperature. The mixture is refluxed under nitrogen for about 2 days before it is cooled to room temperature and filtered. Compound 3400 can be recovered by conventional techniques such as neutralization, extraction, precipitation, chromatography, filtration and the like; or, alternatively, used in the next step without purification and/or isolation. Alternatively, a mixture of compound 3300, an excess of an appropriately substituted phenol, an excess of cesium carbonate, an excess of 2,2,6,6-tetramethylheptane-3,5-dione, and copper (I) chloride in N-methyl-2-pyrrolidone can be heated at 100 to 150° C. for 1-5 days, cooled to room temperature, and quenched with water. Compound 3400 can then be recovered by conventional techniques such as neutralization, extraction, precipitation, chromatography, filtration and the like; or, alternatively, used in the next step without purification and/or isolation. Compound 3800 are easily accessible by treatment of 3700 with tert-butyl-dimethylsilylchloride.

Alternatively, compound 2500 is obtained by reaction of appropriately substituted phthalides such as compound 3600 with suitable halogenating reagents such as, by way of example, 1.3 equivalents of thionylchloride in the presence of suitable catalysts such as boric acid and triphenylphosphine oxide at 130 to 140° C. for about 18 h followed by treatment with an appropriate alcohol such as methanol. Compound 2500 can be recovered by conventional techniques such as neutralization, extraction, precipitation, chromatography, filtration and the like; or, alternatively, used in the next step without purification and/or isolation. Compound 3600 is easily obtained by reacting 3500 with benzylzinc bromide using a variant of the Negishi coupling.

E. Compound Testing

The biological activity of the compounds of the invention may be assessed using any conventionally known methods. Suitable assay methods are well known in the art. The following assays are presented only as examples and are not intended to be limiting. The compounds of the invention are active in at least one of the following assays.

It is contemplated that due to the cyano substitution at the C-1 position of the isoquinoline compounds, the compounds of the invention show surprising and unexpected improved efficacy over comparable compounds not possessing cyano at the C-1 position. For example, compounds having a cyano at the C-1 position of the isoquininoline ring, when compared to corresponding compounds having, for example, hydrogen, methyl, or halogen, at the C-1 position are more than 2-fold, more particularly, more than 4-fold, even more particularly more than 10-fold or 50-fold more potent at increasing circulating erythropoietin levels. Examples of this are more thoroughly discussed in Example 54.

a. Cell-Based HIFα Stabilization Assay

Human cells derived from various tissues are separately seeded into 35 mm culture dishes and grown at 37° C., 20% $O_2$, 5% $CO_2$ in standard culture medium, e.g., DMEM, 10% FBS. When cell layers reach confluence, the media is replaced with OPTI-MEM media (Invitrogen Life Technologies, Carlsbad Calif.) and cell layers are incubated for approximately 24 hours in 20% $O_2$, 5% $CO_2$ at 37° C. Compound or 0.013% DMSO is then added to existing medium, and incubation is continued overnight.

Following incubation, the media is removed, centrifuged, and stored for analysis (see VEGF and EPO assays below). The cells are washed two times in cold phosphate buffered saline (PBS) and then lysed in 1 mL of 10 mM Tris (pH 7.4), 1 mM EDTA, 150 mM NaCl, 0.5% IGEPAL (Sigma-Aldrich, St. Louis Mo.), and a protease inhibitor mix (Roche Molecular Biochemicals) for 15 minutes on ice. Cell lysates are centrifuged at 3,000×g for 5 minutes at 4° C., and the cytosolic fractions (supernatant) are collected. The nuclei (pellet) are resuspended and lysed in 100 μL of 20 mM HEPES (pH 7.2), 400 mM NaCl, 1 mM EDTA, 1 mM dithiothreitol, and a protease mix (Roche Molecular Biochemicals), centrifuged at 13,000×g for 5 minutes at 4° C., and the nuclear protein fractions (supernatant) are collected.

Nuclear fractions are analyzed for HIF-1α using a QUANTIKINE immunoassay (R&D Systems, Inc., Minneapolis Minn.) according to the manufacturer's instructions.

b. Cell-Based VEGF and EPO ELISA Assays

Conditioned media collected from cell cultures as described above is analyzed for vascular endothelial growth factor (VEGF) and/or erythropoietin (EPO) expression using an appropriate QUANTIKINE immunoassay (R&D Systems) according to the manufacturer's instructions.

c. HIF-PH Assay

Ketoglutaric acid α-[1-$^{14}$C]-sodium salt, Ketoglutaric acid-[1-$^{14}$C]-sodium salt, alpha-ketoglutaric acid sodium salt, and HPLC purified peptide may be obtained from commercial sources, e.g., Perkin-Elmer (Wellesley Mass.), Sigma-Aldrich, and SynPep Corp. (Dublin Calif.), respectively. Peptides for use in the assay may be fragments of HIFα as described above or as disclosed in International Publication WO 2005/118836, incorporated by reference herein. HIF-PH, e.g., HIF-PH2 (EGLN1) can be expressed in, e.g., insect Hi5 cells and partially purified, e.g., through a SP ion exchange chromatography column. Enzyme activity is determined by capturing $^{14}CO_2$ using an assay described by Kivirikko and Myllyla (1982, Methods Enzymol 82:245-304). Assay reactions contain 50 mM HEPES (pH 7.4), 100 μM α-ketoglutaric acid sodium salt, 0.30 μCi/mL ketoglutaric acid α-[1-$^{14}$C]-sodium salt; 40 μM $FeSO_4$, 1 mM ascorbate, 1541.8 units/mL Catalase, with or without 50 μM peptide substrate and various concentrations of compound of the invention. Reactions are initiated by addition of HIF-PH enzyme.

The peptide-dependent percent turnover is calculated by subtracting percent turnover in the absence of peptide from percent turnover in the presence of substrate peptide. Percent inhibition and $IC_{50}$ are calculated using peptide-dependent percent turnover at given inhibitor concentrations. Calculation of $IC_{50}$ values for each inhibitor is conducted, e.g., using GraFit software (Erithacus Software Ltd., Surrey UK).

The compounds of the present invention when tested in assays, demonstrated improved activity as compared to non-cyano compounds, as shown in Table 1 below. Table 1 can be found in example 54.

F. Pharmaceutical Formulations and Routes of Administration

The compounds of the present invention can be delivered directly or in pharmaceutical compositions along with suitable carriers or excipients, as is well known in the art. Various treatments embodied herein can comprise administration of an effective amount of a compound of the invention to a subject in need, e.g., a subject having or at risk for anemia due to, e.g., chronic renal failure, diabetes, cancer, AIDS, radiation therapy, chemotherapy, kidney dialysis, or surgery. In a preferred embodiment, the subject is a mammalian subject, and in a most preferred embodiment, the subject is a human subject.

An effective amount of a compound can readily be determined by routine experimentation, as can the most effective and convenient route of administration and the most appropriate formulation. Various formulations and drug delivery systems are available in the art. See, e.g., Gennaro, A. R., ed. (1995) *Remington's Pharmaceutical Sciences, supra.*

Suitable routes of administration may, for example, include oral, rectal, transmucosal, nasal, or intestinal administration and parenteral delivery, including intramuscular, subcutaneous, intramedullary injections, as well as intrathecal, direct intraventricular, intravenous, intraperitoneal, intranasal, or intraocular injections. The compound or composition thereof may be administered in a local rather than a systemic manner. For example, a compound or composition thereof can be delivered via injection or in a targeted drug delivery system, such as a depot or sustained release formulation.

The pharmaceutical compositions of the present invention may be manufactured by any of the methods well-known in the art, such as by conventional mixing, dissolving, granulating, dragee-making, levigating, emulsifying, encapsulating, entrapping, or lyophilizing processes. As noted above, the compositions of the present invention can include one or more physiologically acceptable carriers such as excipients and auxiliaries that facilitate processing of active molecules into preparations for pharmaceutical use.

Proper formulation is dependent upon the route of administration chosen. For injection, for example, the composition may be formulated in aqueous solutions, preferably in physiologically compatible buffers such as Hanks' solution, Ringer's solution, or physiological saline buffer. For transmucosal or nasal administration, penetrants appropriate to the barrier to be permeated are used in the formulation. Such penetrants are generally known in the art. In a preferred embodiment of the present invention, the present compounds are prepared in a formulation intended for oral administration. For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject. The compounds may also be formulated in rectal compositions such as suppositories or retention enemas, e.g., containing conventional suppository bases such as cocoa butter or other glycerides.

Pharmaceutical preparations for oral use can be obtained as solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Also, wetting agents such as sodium dodecyl sulfate may be included.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations for oral administration include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

In one embodiment, the compounds of the present invention can be administered transdermally, such as through a skin patch, or topically. In one aspect, the transdermal or topical formulations of the present invention can additionally comprise one or multiple penetration enhancers or other effectors, including agents that enhance migration of the delivered compound. Transdermal or topical administration could be preferred, for example, in situations in which location specific delivery is desired.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide, or any other suitable gas. In the case of a pressurized aerosol, the appropriate dosage unit may be determined by providing a valve to deliver a metered amount. Capsules and cartridges of, for example, gelatin, for use in an inhaler or insufflator may be formulated. These typically contain a powder mix of the compound and a suitable powder base such as lactose or starch.

Compositions formulated for parenteral administration by injection, e.g., by bolus injection or continuous infusion can be presented in unit dosage form, e.g., in ampoules or in multi-dose containers, with an added preservative. The compositions may take such forms as suspensions, solutions, or emulsions in oily or aqueous vehicles, and may contain formulatory agents such as suspending, stabilizing and/or dispersing agents. Formulations for parenteral administration include aqueous solutions or other compositions in water-soluble form.

Suspensions of the active compounds may also be prepared as appropriate oily injection suspensions. Suitable lipophilic solvents or vehicles include fatty oils such as sesame oil and synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Alternatively, the active ingredient may be in powder form for constitution with a suitable vehicle, e.g., sterile pyrogen-free water, before use.

As mentioned above, the compositions of the present invention may also be formulated as a depot preparation. Such long acting formulations may be administered by implantation (for example, subcutaneously or intramuscularly) or by intramuscular injection. Thus, for example, the present compounds may be formulated with suitable polymeric or hydrophobic materials (for example as an emulsion in an acceptable oil) or ion exchange resins, or as sparingly soluble derivatives, for example, as a sparingly soluble salt.

Suitable carriers for the hydrophobic molecules of the invention are well known in the art and include co-solvent systems comprising, for example, benzyl alcohol, a nonpolar surfactant, a water-miscible organic polymer, and an aqueous phase. The co-solvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5 W) consists of VPD diluted 1:1 with a 5% dextrose in water solution. This co-solvent system is effective in dissolving hydrophobic compounds and produces low toxicity upon systemic administration. Naturally, the proportions of a co-solvent system may be varied considerably without destroying its solubility and toxicity characteristics. Furthermore, the identity of the co-solvent components may be varied. For example, other low-toxicity nonpolar surfactants may be used instead of polysorbate 80, the fraction size of polyethylene glycol may be varied, other biocompatible polymers may replace polyethylene glycol, e.g., polyvinyl pyrrolidone, and other sugars or polysaccharides may substitute for dextrose.

Alternatively, other delivery systems for hydrophobic molecules may be employed. Liposomes and emulsions are well known examples of delivery vehicles or carriers for hydrophobic drugs. Liposomal delivery systems are discussed above in the context of gene-delivery systems. Certain organic solvents such as dimethylsulfoxide also may be employed, although usually at the cost of greater toxicity. Additionally, the compounds may be delivered using sustained-release systems, such as semi-permeable matrices of solid hydrophobic polymers containing the effective amount of the composition to be administered. Various sustained-release materials are established and available to those of skill in the art. Sustained-release capsules may, depending on their chemical nature, release the compounds for a few weeks up to over 100 days. Depending on the chemical nature and the biological stability of the therapeutic reagent, additional strategies for protein stabilization may be employed.

For any composition used in the various treatments embodied herein, a therapeutically effective dose can be estimated initially using a variety of techniques well known in the art. For example, in a cell culture assay, a dose can be formulated in animal models to achieve a circulating concentration range that includes the $IC_{50}$ as determined in cell culture. Dosage ranges appropriate for human subjects can be determined, for example, using data obtained from cell culture assays and other animal studies.

A therapeutically effective dose of a compound refers to that amount of the compound that results in amelioration of symptoms or a prolongation of survival in a subject. Toxicity and therapeutic efficacy of such molecules can be determined by standard pharmaceutical procedures in cell cultures or experimental animals, e.g., by determining the $LD_{50}$ (the dose lethal to 50% of the population) and the $ED_{50}$ (the dose therapeutically effective in 50% of the population). The dose ratio of toxic to therapeutic effects is the therapeutic index, which can be expressed as the ratio $LD_{50}/ED_{50}$. Compounds that exhibit high therapeutic indices are preferred.

Dosages preferably fall within a range of circulating concentrations that includes the $ED_{50}$ with little or no toxicity. Dosages may vary within this range depending upon the dosage form employed and the route of administration utilized. The exact formulation, route of administration, and dosage should be chosen, according to methods known in the art, in view of the specifics of a subject's condition.

Dosage amount and interval may be adjusted individually to provide plasma levels of the active moiety that are sufficient to modulate a desired parameter, e.g., endogenous erythropoietin plasma levels, i.e. minimal effective concentration (MEC). The MEC will vary for each compound but can be estimated from, for example, in vitro data. Dosages necessary to achieve the MEC will depend on individual characteristics and route of administration. Compounds or compositions thereof should be administered using a regimen which maintains plasma levels above the MEC for about 10-90% of the duration of treatment, preferably about 30-90% of the duration of treatment, and most preferably between 50-90%. In cases of local administration or selective uptake, the effective local concentration of the drug may not be related to plasma concentration. Alternatively, modulation of a desired parameter, e.g., stimulation of endogenous erythropoietin, may be achieved by 1) administering a loading dose followed by a maintenance dose, 2) administering an induction dose to rapidly achieve the desired parameter, e.g., erythropoietin levels, within a target range, followed by a lower maintenance dose to maintain, e.g., hematocrit, within a desired target range, or 3) repeated intermittent dosing.

The amount of compound or composition administered will, of course, be dependent on a variety of factors, including the sex, age, and weight of the subject being treated, the severity of the affliction, the manner of administration, and the judgment of the prescribing physician.

The present compositions may, if desired, be presented in a pack or dispenser device containing one or more unit dosage forms containing the active ingredient. Such a pack or device may, for example, comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labeled for treatment of an indicated condition. Suitable conditions indicated on the label may include treatment of conditions, disorders, or diseases in which anemia is a major indication.

These and other embodiments of the present invention will readily occur to those of ordinary skill in the art in view of the disclosure herein, and are specifically contemplated.

EXAMPLES

The invention is further understood by reference to the following examples, which are intended to be purely exemplary of the invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description and accompanying figures. Such modifications fall within the scope of the appended claims.

Unless otherwise stated all temperatures are in degrees Celsius. Also, in these examples and elsewhere, abbreviations have the following meanings:

bs=broad singlet
DMSO=dimethyl sulfoxide
d=doublet
dd=doublet of doublets
dppf 1,1'-bis(diphenylphosphino)ferroceno
DMF=dimethyl formamide
DMEM=Dulbecco's Modified Eagle Medium
EtOAc=ethyl acetate
EDTA=ethylenediaminetetraacetic acid
FBS=fetal bovine serum
g=gram
h=hour
HPLC=High Performance Liquid Chromatography
Hz=hertz
MS=Mass Spectroscopy
MeONa=sodium methoxide
MeOH=methanol
MHz=mega Hertz
μM=micromolar
μL=microliter
mg=milligram
mL=milliliter
mM=millimolar
mm=millimeter
mmol=millimolar
min=minute
M=molar
mol=moles
m=multiplet
N=normal
NMR=nuclear magnetic resonance
Pd/C=palladium over carbon
$Pd_2(dba)_3$=tris(dibenzylideneacetone)dipalladium(0)
q=quartet
s=singlet
Ts=toluene-4-sulfonyl
t=triplet Example 1

[(1-Cyano-4-hydroxy-isoquinoline-3-carbonyl)-amino]-acetic acid a. 1-Cyano-4-hydroxy-isoquinoline-3-carboxylic acid butyl ester A mixture of 1-bromo-4-hydroxy-isoquinoline-3-carboxylic acid butyl ester (1.621 g, 5 mmol; prepared as shown in Scheme 2, according to US 2004/0254215 A1; $^1$H NMR (200 MHz, $CD_3OD$) δ 11.89 (s, 1H), 8.41 (m, 1H), 8.25 (m, 1H), 7.84 (m, 2H), 4.49 (t, J=7.0 Hz, 2H), 1.87 (m, 2H), 1.47 (m, 2H), 1.00 (t, J=7.2 Hz, 3H)), CuCN (905 mg, 10 mmol) and dimethylformamide (20 mL) was refluxed with stirring under nitrogen for 5 min. After cooling to ambient temperature the mixture was diluted with water (300 mL). Then ethyl acetate (150 mL) was added and the mixture was shaken thoroughly for 5 min before it was filtered through a pad of celite. The organic phase of the filtrate was separated, and dried over $MgSO_4$ before silica gel was added. The mixture was concentrated in vacuo. The residue was added on top of a short column filled with silica gel. Elution with dichloromethane gave the title compound as a yellowish solid (627 mg); MS-(−)-ion: M−1=269.2.

b. [(1-Cyano-4-hydroxy-isoquinoline-3-carbonyl)-amino]-acetic acid

A mixture of 1-cyano-4-hydroxy-isoquinoline-3-carboxylic acid butyl ester (89 mg, 0.33 mmol), glycine (375 mg, 5 mmol), and a 0.5 N solution of MeONa in MeOH (8 mL, 4 mmol) was refluxed with stirring for 48 h before it was concentrated in vacuo. The residue was dissolved in water (20 mL). The solution was washed with diethyl ether before its pH was adjusted to 2 to 3 by addition of aqueous 6 N HCl. The resulting suspension was extracted with ethyl acetate (1×30 mL). The organic phase was dried over $MgSO_4$ and concentrated in vacuo to give the title compound as a yellowish solid (72 mg); MS-(−)-ion: M−1=270.2.

Example 2

2-(S)-[(1-Cyano-4-hydroxy-isoquinoline-3-carbonyl)-amino]-propionic acid

A mixture of 1-cyano-4-hydroxy-isoquinoline-3-carboxylic acid butyl ester (135 mg, 0.5 mmol, see Example 1(a)), (S)-alanine (225 mg, 2.5 mmol) and a 0.5 N solution of MeONa in methanol (5 mL, 2.5 mmol) was heated in a microwave oven with stirring for 40 min at 120° C. before the mixture was concentrated in vacuo. To the residue was added water (10 mL) and the mixture was washed with diethyl ether (4×40 mL). The pH of the purified solution was adjusted to about 2 by the addition of aqueous 6 N HCl. The resulting suspension was extracted with ethyl acetate (1×40 mL). The organic phase was dried over $MgSO_4$ and concentrated in vacuo to give the title compound as a yellowish solid (101 mg); MS-(−)-ion: M−1=284.1.

Example 3

[(1-Cyano-4-hydroxy-7-phenoxy-isoquinoline-3-carbonyl)-amino]-acetic acid a. 1-Cyano-4-hydroxy-7-phenoxy-isoquinoline-3-carboxylic acid butyl ester A mixture of 1-bromo-4-hydroxy-7-phenoxy-isoquinoline-3-carboxylic acid butyl ester (624 mg, 1.5 mmol; prepared as shown in Scheme 2, and according to US 2004/0254215 A1, $^1$H NMR ($CDCl_3$): δ=11.89 (s, 1H), 8.35 (d, 1H), 7.63 (d, 1H), 7.08 to 7.52 (m, 6H), 4.47 (t, 2H), 1.84 (m, 2H), 1.48 (m, 2H), 0.99 (t, 3H)), CuCN (271 mg, 3 mmol) and dimethylformamide (6 mL) was refluxed with stirring under nitrogen for 15 min. After cooling to ambient temperature the mixture was diluted with ethyl acetate (100 mL). The resulting suspension was filtered through a pad of celite. The filtrate was washed with water (2×250 mL), and dried over $MgSO_4$ before silica gel was added. Subsequently, the mixture was concentrated in vacuo. The residue was added on top of a short column filled with silica gel. Elution with dichloromethane gave the title compound as a white solid (313 mg); MS-(−)-ion: M−1=361.2.

b. [(1-Cyano-4-hydroxy-7-phenoxy-isoquinoline-3-carbonyl)-amino]-acetic acid

The title compound was obtained from 1-cyano-4-hydroxy-7-phenoxy-isoquinoline-3-carboxylic acid butyl ester and glycine analogous to Example 1(b)); MS-(−)-ion: M−1=362.0.

Example 4

2-(S)-[(1-Cyano-4-hydroxy-7-phenoxy-isoquinoline-3-carbonyl)-amino]-propionic acid The title compound was obtained from 1-cyano-4-hydroxy-7-phenoxy-isoquinoline-3-carboxylic acid butyl ester (see Example 3a) and (S)-alanine in analogy to Example 2; MS-(−)-ion: M−1=376.0.

Example 5

2-(R)-[(1-Cyano-4-hydroxy-7-phenoxy-isoquinoline-3-carbonyl)-amino]-propionic acid The title compound was obtained from 1-cyano-4-hydroxy-7-phenoxy-isoquinoline-3-carboxylic acid butyl ester (see Example 3a) and (R)-alanine in analogy to Example 2; MS-(−)-ion: M−1=376.1.

Example 6

{[1-Cyano-7-(4-fluoro-phenoxy)-4-hydroxy-isoquinoline-3-carbonyl]-amino}-acetic acid a. 1-Cyano-7-(4-fluoro-phenoxy)-4-hydroxy-isoquinoline-3-carboxylic acid butyl ester This compound was synthesized from 1-bromo-7-(4-fluoro-phenoxy)-4-hydroxy-isoquinoline-3-carboxylic acid butyl ester (prepared as shown in Scheme 2, according to US 2004/0254215 A1, $^1$H NMR (CDCl$_3$) δ=11.89 (s, 1H), 8.36 (d, 1H), 7.57 (d, 1H), 7.44 to 7.50 (m, 1H), 7.08 to 7.16 (m, 4H), 4.47 (t, 2H), 1.78 to 1.93 (m, 2H), 1.38 to 1.58 (m, 2H), 0.99 (t, 3H)) and CuCN in analogy to Example 3(a)); MS-(−)-ion: M−1=379.2.

b. {[1-Cyano-7-(4-fluoro-phenoxy)-4-hydroxy-isoquinoline-3-carbonyl]-amino}-acetic acid The title compound was obtained from 1-cyano-7-(4-fluoro-phenoxy)-4-hydroxy-isoquinoline-3-carboxylic acid butyl ester and glycine in analogy to example 1b); MS-(−)-ion: M−1=380.0.

Example 7

[(1-Cyano-4-hydroxy-7-trifluoromethyl-isoquinoline-3-carbonyl)-amino]-acetic acid a. 1-Cyano-4-hydroxy-7-trifluoromethyl-isoquinoline-3-carboxylic acid butyl ester This compound was synthesized from 1-bromo-4-hydroxy-7-trifluoromethyl-isoquinoline-3-carboxylic acid butyl ester (prepared as shown in Scheme 2, according to US 2004/0254215 A1, $^1$H NMR (CDCl$_3$): δ=11.96 (s, 1H), 8.52 to 8.56 (m, 2H), 7.99 (dd, 1H), 4.51 (t, 2H), 1.86 (m, 2H), 1.48 (m, 2H), 1.00 (t, 3H)) and CuCN in analogy to Example 1(a)); MS-(−)-ion: M−1=337.1.

b. [(1-Cyano-4-hydroxy-7-trifluoromethyl-isoquinoline-3-carbonyl)-amino]-acetic acid The title compound was obtained from 1-cyano-4-hydroxy-7-trifluoromethyl-isoquinoline-3-carboxylic acid butyl ester and glycine in analogy to Example 1(b)); MS-(−)-ion: M−1=338.0.

Example 8

[(7-Chloro-1-cyano-4-hydroxy-isoquinoline-3-carbonyl)-amino]-acetic acid a. 7-Chloro-1-cyano-4-hydroxy-isoquinoline-3-carboxylic acid butyl ester

This compound was synthesized from 1-bromo-7-chloro-4-hydroxy-isoquinoline-3-carboxylic acid butyl ester (prepared as shown in Scheme 2, according to US 2004/0254215 A1, $^1$H NMR (CDCl$_3$): δ=11.92 (s, 1H), 8.34 (d, 1H), 8.25 (d, 1H), 7.75 (dd, 1H), 4.49 (t, 2H), 1.86 (m, 2H), 1.48 (m, 2H), 1.00 (t, 3H)) and CuCN in analogy to Example 1(a)); MS-(−)-ion: M−1=303.2.

b. [(7-Chloro-1-cyano-4-hydroxy-isoquinoline-3-carbonyl)-amino]-acetic acid The title compound was obtained from 7-chloro-1-cyano-4-hydroxy-isoquinoline-3-carboxylic acid butyl ester and glycine in analogy to Example 1(b)); MS-(−)-ion: M−1=303.9

Example 9

[(1-Cyano-4-hydroxy-8-phenoxy-isoquinoline-3-carbonyl)-amino]-acetic acid a. 3-Iodo-2-methyl-benzoic acid ethyl ester

To a stirred solution of 3-iodo-2-methyl-benzoic acid (30 g, 0.11 mol) in ethanol (425 mL) was added thionyl chloride (42 mL, 0.57 mol) at 0° C. The mixture was refluxed for 4.5 h before it was cooled to room temperature and concentrated in vacuo. The residue was partitioned between ethyl ether and saturated sodium bicarbonate solution. The organic layer was washed with brine, dried over anhydrous sodium sulfate and was concentrated in vacuo to give the title compound as a pale yellow oil (32.28 g): $^1$H NMR (CDCl$_3$, 200 MHz): δ=7.94 (d, J=7.8 Hz, 1H), 7.70 (d, J=7.4 Hz, 1H), 6.90 (t, J=7.8 Hz, 1H), 4.35 (q, J=7.2 Hz, 2H), 2.65 (s, 3H), 1.38 (t, J=7.0 Hz, 3H).

b. 2-Methyl-3-phenoxy-benzoic acid ethyl ester

To a mixture of 3-iodo-2-methyl-benzoic acid ethyl ester (30.04 g, 0.10 mol), phenol (14.62 g, 0.16 mol), cesium carbonate (50.6 g, 0.16 mol), 1-naphthoic acid (26.7 g, 0.16 mol), molecular sieves (25.6 g, 4 angstrom, 4-8 mesh), ethyl acetate (505 μL, 5 mmol), and anhydrous toluene (108 mL) was added a copper(I) trifluoromethanesulfonate-benzene complex (5.21 g, 0.01 mol) at room temperature. The mixture was refluxed under nitrogen for 43 h before it was cooled to room temperature and filtered. The filter cake was suspended in ethyl acetate (250 mL) and the slurry was stirred for 0.5 h. The solid components were then separated by filtration and discarded. The filtrates were combined, washed with water, aqueous 0.5 N sodium hydroxide solution (2×), and brine, dried over anhydrous sodium sulfate and concentrated in vacuo. The residue was purified by flash column chromatography on silica gel with a gradient of ethyl acetate and hexanes. Fractions containing both the title compound and the starting material 3-iodo-2-methyl-benzoic acid ethyl ester were pooled and concentrated in vacuo to give a yellow oil (15.9 g); fractions containing only the title compound were pooled and concentrated in vacuo to give a yellow oil (5.25 g): $^1$H NMR (CDCl$_3$, 200 MHz): δ=7.63 (m, 1H), 7.24 (m, 3H), 7.05 (m, 2H), 6.87 (m, 2H), 4.37 (q, J=7.0 Hz, 2H), 2.45 (s, 3H), 1.40 (t, J=7.0 Hz, 3H).

c. 2-Bromomethyl-3-phenoxy-benzoic acid ethyl ester

A mixture of 2-methyl-3-phenoxy-benzoic acid ethyl ester (5.23 g, 0.02 mol), N-bromosuccinimide (3.82 g, 0.02 mol) and benzoyl peroxide (247.5 mg, 1.1 mmol) in carbon tetrachloride (80 mL) was refluxed for 4 h before it was cooled to room temperature and filtered. The filtrate was washed with water, saturated aqueous sodium bicarbonate solution, and brine before it was dried over anhydrous sodium sulfate and concentrated in vacuo to give the title compound as a yellow oil (7.08 g): $^1$H NMR (CDCl$_3$, 200 MHz): δ=7.66 (m, 1H), 7.24 (m, 3H), 7.03 (m, 1H), 6.98 (m, 3H), 5.09 (s, 3H), 4.42 (q, J=7.2 Hz, 2H), 1.44 (t, J=7.2 Hz, 3H).

d. 2-{[Methoxycarbonylmethyl-(toluene-4-sulfonyl)-amino]-methyl}-3-phenoxy-benzoic acid ethyl ester A mixture of 2-bromomethyl-3-phenoxy-benzoic acid ethyl ester (6.83 g, 0.02 mol), (toluene-4-sulfonylamino)-acetic acid methyl ester (4.97 g, 0.02 mol), sodium iodide (4.59 g, 0.03 mol), potassium carbonate (4.24 g, 0.03 mol), and anhydrous dimethylformamide (50 mL) was stirred at room temperature for 4 h before it was diluted with water and extracted with ethyl acetate. The organic layer was separated and washed with water and brine. Then it was dried over anhydrous sodium sulfate and concentrated in vacuo. The residue was purified by flash column chromatography on silica gel with a gradient of ethyl acetate and hexanes to give the title compound as a yellow oil (5.10 g): MS: (+) m/z 497.8 (M+1).

e. 4-Hydroxy-8-phenoxy-isoquinoline-3-carboxylic acid methyl ester

To a stirred solution of 2-{[methoxycarbonylmethyl-(toluene-4-sulfonyl)-amino]-methyl}-3-phenoxy-benzoic acid ethyl ester (5.07 g, 0.01 mol) in anhydrous methanol (22 mL) was added dropwise a mixture of sodium methoxide solution (30% wt, 5.6 mL) and anhydrous methanol (4 mL) at 0° C. The mixture was stirred at 0° C. for 10 minutes and then at room temperature for additional 3 h before it was concentrated in vacuo. Water was added and the pH of the slurry was adjusted with aqueous 1 N HCl to pH=10. The precipitate formed was separated by filtration, washed with water, saturated sodium bicarbonate solution, and water before it was dried in vacuo to give the title compound as a white solid (2.21 g): $^1$H NMR (CDCl$_3$, 200 MHz): δ=11.73 (s, 1H), 9.21 (s, 1H), 8.06 (d, J=8.2 Hz, 1H), 7.61 (t, J=8.0 Hz, 1H), 7.40 (m, 2H), 7.13 (m, 4H), 4.10 (s, 3H).

f. 1-Bromo-4-hydroxy-8-phenoxy-isoquinoline-3-carboxylic acid methyl ester

A mixture of 4-hydroxy-8-phenoxy-isoquinoline-3-carboxylic acid methyl ester (103 mg, 0.35 mmol), N-bromosuccinimide (65 mg, 0.37 mmol), benzoyl peroxide (4.2 mg, 0.02 mmol), and carbon tetrachloride (2.5 mL) was refluxed for 4 h before it was cooled to room temperature and filtered. The filtrate was washed with water, saturated aqueous sodium bicarbonate solution, and brine before it was dried over anhydrous sodium sulfate and concentrated in vacuo to give the title compound as a yellow solid (128 mg): MS: (+) m/z 374.0, 376.0 (M+1, $^{79}$Br/$^{81}$Br), MS: (−) m/z 372.1, 374.1 (M−1, $^{79}$Br/$^{81}$Br).

g. 1-Cyano-4-hydroxy-8-phenoxy-isoquinoline-3-carboxylic acid methyl ester

A mixture of 1-bromo-4-hydroxy-8-phenoxy-isoquinoline-3-carboxylic acid methyl ester (1.22 g, 3.3 mmol), copper(I) cyanide (585 mg, 6.6 mmol), and anhydrous dimethylformamide (16 mL) was refluxed for ten minutes before it was cooled to room temperature and diluted with water. To the resulting slurry was added a chloroform/isopropanol mixture (3:1, 150 mL). After stirring for 10 minutes the solid components were separated by filtration and discarded. The organic layer of the filtrate was washed with water, and brine before it was dried over anhydrous sodium sulfate and concentrated in vacuo. The residue was purified by flash column chromatography on silica gel with a gradient of methanol and dichloromethane to give the title compound as a white solid (574 mg): $^1$H NMR (CDCl$_3$, 200 MHz): δ=12.26 (s, 1H), 8.15 (m, 1H), 7.71 (t, J=8.2 Hz, 1H), 7.38 (m, 2H), 7.17 (m, 4H), 4.12 (s, 3H).

h. [(1-Cyano-4-hydroxy-8-phenoxy-isoquinoline-3-carbonyl)-amino]-acetic acid A mixture of 1-cyano-4-hydroxy-8-phenoxy-isoquinoline-3-carboxylic acid methyl ester (322 mg, 1.0 mmol), glycine (1.51 g, 20.1 mmol), and a 0.5 M sodium methoxide solution in methanol (38.2 mL) was refluxed for 31 h before it was cooled to room temperature and concentrated in vacuo. Water (75 mL) was added and the pH of the yellow suspension was adjusted to 10 with aqueous 1 N HCl. A clear yellow solution was obtained after 5 minutes of sonication. The solution was washed with dichloromethane (2×50 mL). The remaining aqueous layer was acidified to pH=3 with aqueous 1 N HCl. The white precipitate formed was separated by filtration, washed with water and dried in vacuo to give the title compound as a white solid (354 mg): $^1$H NMR (DMSO-d$_6$, 200 MHz): δ=12.86 (bs, 1H), 9.56 (t, 1H), 8.09 (m, 1H), 7.88 (t, J=8.2 Hz, 1H), 7.47 (m, 2H), 7.21 (m, 4H), 4.05 (d, J=5.8 Hz, 2H).

Example 10

{[1-Cyano-8-(4-fluoro-phenoxy)-4-hydroxy-isoquinoline-3-carbonyl]-amino}-acetic acid a. 3-(4-Fluoro-phenoxy)-2-methyl-benzoic acid ethyl ester

A mixture of 3-iodo-2-methyl-benzoic acid ethyl ester (6.29 g, 0.02 mol), para-fluorophenol (4.86 g, 0.04 mol), cesium carbonate (14.14 g, 0.04 mol), 2,2,6,6-tetramethyl-heptane-3,5-dione (447 µL, 2 mmol) and copper (I) chloride (1.07 g, 0.01 mol) in anhydrous N-methyl-2-pyrrolidone (38 mL) was heated at 130° C. for 3 days before it was cooled to room temperature, quenched with water and filtered. The filtrate was extracted with ethyl acetate. The organic layer was washed twice with 0.5 N sodium hydroxide, brine, dried over anhydrous sodium sulfate and concentrated in vacuo. The residue was purified by flash column chromatography on silica gel with a gradient of ethyl acetate and hexanes to give the title compound as a pale green oil (2.99 g): $^1$H NMR (CDCl$_3$, 200 MHz): δ=7.63 (m, 1H), 7.18 (m, 2H), 6.98 (m, 2H), 6.85 (m, 2H), 4.37 (q, J=7.0 Hz, 2H), 2.45 (s, 3H), 1.40 (t, J=7.0 Hz, 3H).

b. 2-Bromomethyl-3-(4-fluoro-phenoxy)-benzoic acid ethyl ester

A mixture of 3-(4-fluoro-phenoxy)-2-methyl-benzoic acid ethyl ester (2.63 g, 9.60 mmol), N-bromosuccinimide (1.79 g, 10.08 mmol) and benzoyl peroxide (116 mg, 0.48 mmol) in carbon tetrachloride (35 mL) was refluxed for 4 h before it was cooled to room temperature and partitioned between dichloromethane and water. The organic layer was washed with saturated aqueous sodium bicarbonate solution, brine, dried over anhydrous sodium sulfate and concentrated in vacuo to give the title compound as a yellow oil (3.44 g): $^1$H NMR (CDCl$_3$, 200 MHz): δ=7.67 (m, 1H), 7.27 (m, 2H), 7.01 (m, 4H), 5.09 (s, 3H), 4.42 (q, J=7.2 Hz, 2H), 1.44 (t, J=7.2 Hz, 3H).

c. 3-(4-Fluoro-phenoxy)-2-{[methoxycarbonylmethyl-(toluene-4-sulfonyl)-amino]-methyl}-benzoic acid ethyl ester A mixture of 2-bromomethyl-3-(4-fluoro-phenoxy)-benzoic acid ethyl ester (3.37 g, 9.57 mmol), (toluene-4-sulfonylamino)-acetic acid methyl ester (2.33 g, 9.57 mmol), sodium iodide (2.15 g, 14.36 mmol) and potassium carbonate (1.98 g, 14.36 mmol) in anhydrous dimethylformamide (22 mL) was stirred at room temperature for 24 h before it was quenched with water, and extracted with ethyl acetate. The organic layer was washed with water, brine, dried over anhydrous sodium sulfate and concentrated in vacuo. The residue was purified by flash column chromatography on silica gel with a gradient of ethyl acetate and hexane to give the title compound as a yellow oil (2.67 g): MS: (+) m/z 538.13 (M+Na$^+$).

d. 8-(4-Fluoro-phenoxy)-4-hydroxy-isoquinoline-3-carboxylic acid methyl ester

To a stirred solution of 3-(4-fluoro-phenoxy)-2-{[methoxycarbonylmethyl-(toluene-4-sulfonyl)-amino]-methyl}-benzoic acid ethyl ester (2.66 g, 5.17 mmol) in anhydrous methanol (8 mL) was added dropwise a solution of sodium methoxide (30% wt, 2.8 mL) and methanol (2 mL) at 0° C. The mixture was stirred at 0° C. for 10 minutes and then 3 h at room temperature before it was concentrated in vacuo. Water was added and the pH of the slurry was adjusted with 1 N HCl to pH=10. The resulting precipitate was collected by filtration, washed with water, saturated sodium bicarbonate, and water, and was dried in vacuo to give the title compound as a white solid (1.51 g): MS: (+) m/z 314.07 (M+1).

e. 1-Bromo-8-(4-fluoro-phenoxy)-4-hydroxy-isoquinoline-3-carboxylic acid methyl ester A mixture of 8-(4-fluoro-phenoxy)-4-hydroxy-isoquinoline-3-carboxylic acid methyl ester (1.21 g, 3.87 mmol), N-bromosuccinimide (723 mg, 4.06 mmol) and benzoyl peroxide (47 mg, 0.19 mmol) in carbon tetrachloride (20 mL) was refluxed for 4 h before it was cooled to room temperature and partitioned between dichloromethane and water. The organic layer was washed with saturated aqueous sodium bicarbonate, brine, and was dried over anhydrous sodium sulfate and concentrated in vacuo. The residue was purified by flash column chromatography on silica gel with a gradient of dichloromethane and hexane to give the title compound as a pale yellow solid (843 mg): MS: (+) m/z 392.00, 393.93 (M+1, $^{79}$Br/$^{81}$Br).

f. 1-Cyano-8-(4-fluoro-phenoxy)-4-hydroxy-isoquinoline-3-carboxylic acid methyl ester A mixture of 1-bromo-8-(4-fluoro-phenoxy)-4-hydroxy-isoquinoline-3-carboxylic acid methyl ester (400 mg, 1.02 mmol) and copper(I) cyanide (183 mg, 2.04 mmol) in anhydrous dimethylformamide (4 mL) was refluxed for ten minutes before it was cooled to room temperature and quenched with water. The slurry was stirred with chloroform/isopropanol (3:1, 70 mL) and water for ten minutes and filtered. The organic layer was washed with water, brine, dried over anhydrous sodium sulfate, concentrated in vacuo, and purified by flash column chromatography on silica gel with a gradient of methanol and dichloromethane to give the title compound as a white solid (158 mg): MS: (+) m/z 339.07 (M+1).

g. {[1-Cyano-8-(4-fluoro-phenoxy)-4-hydroxy-isoquinoline-3-carbonyl]-amino}-acetic acid A mixture of 1-cyano-8-(4-fluoro-phenoxy)-4-hydroxy-isoquinoline-3-carboxylic acid methyl ester (112 mg, 0.33 mmol), glycine (496 mg, 6.6 mmol), and a 0.5 M solution of sodium methoxide in methanol (12.5 mL, 6.25 mmol) was refluxed for 39 h before it was cooled to room temperature and concentrated in vacuo. Water (75 mL) was added and the pH of the yellow suspension was adjusted to pH=10 with 1 N HCl. The suspension was washed with methylene chloride (2×50 mL). The remaining aqueous layer was acidified to pH=3 with 1 N HCl. The resulting white precipitate was collected by filtration, washed with water, and dried in vacuo to give the title compound as a white solid (109 mg): $^1$H NMR (DMSO-d$_6$, 200 MHz): δ=12.85 (bs, 1H), 9.57 (br s, 1H), 8.09 (d, 1H), 7.83 (t, 1H), 7.27 (m, 5H), 4.05 (d, J=5.8 Hz, 2H); MS: (+) m/z 382.00 (M+1).

Example 11

[(1-Cyano-4-hydroxy-6-methoxy-isoquinoline-3-carbonyl)-amino]-acetic acid a. 1-Bromo-4-hydroxy-6-methoxy-isoquinoline-3-carboxylic acid butyl ester A mixture of 1,4-dihydroxy-6-methoxy-isoquinoline-3-carboxylic acid butyl ester (1.53 g, 5.26 mmol, prepared according to US 2004/0254215 A1 or scheme 2), phosphorus oxybromide (6.04 g, 21.05 mmol), and acetonitrile (40 mL) was refluxed for 16 h before it was cooled to room temperature and partitioned between dichloromethane and aqueous saturated sodium bicarbonate solution for twenty minutes. The mixture was then filtered. The organic layer of the filtrate was separated, washed with water, and brine, dried over anhydrous sodium sulfate and was concentrated in vacuo. The residue was purified by flash column chromatography on silica gel with a gradient of ethyl acetate and dichloromethane to give the title compound as a yellow solid (290 mg): $^1$H NMR (CDCl$_3$, 200 MHz): δ=11.84 (s, 1H), 8.14 (d, J=9.4 Hz, 1H), 7.62 (d, J=2.3 Hz, 1H), 7.83 (dd, J=8.0 Hz, 2.7 Hz, 1H), 4.48 (t, J=7.0 Hz, 2H), 1.86 (m, 1H), 1.55 (m, 1H), 0.99 (t, J=7.4 Hz).

b. 1-Cyano-4-hydroxy-6-methoxy-isoquinoline-3-carboxylic acid butyl ester

A mixture of 1-bromo-4-hydroxy-6-methoxy-isoquinoline-3-carboxylic acid butyl ester (290 mg, 0.82 mmol) and copper(I) cyanide (147 mg, 1.64 mmol) in anhydrous dimethylformamide (4 mL) was refluxed for ten minutes before it was cooled to room temperature and quenched with water. The resulting slurry was stirred with chloroform/isopropanol (3:1, 40 mL) and water for ten minutes and was then filtered. The organic layer of the filtrate was separated, washed with water, and brine, before it was dried over anhydrous sodium sulfate and concentrated in vacuo. The residue was purified by flash column chromatography on silica gel with a gradient of methanol and dichloromethane to give the title compound as a white solid (120 mg): MS: (+) m/z 301.01 (M+1).

c. [(1-Cyano-4-hydroxy-6-methoxy-isoquinoline-3-carbonyl)-amino]-acetic acid A mixture of 1-cyano-4-hydroxy-6-methoxy-isoquinoline-3-carboxylic acid butyl ester (104 mg, 0.35 mmol), glycine (523 mg, 6.97 mmol), and a 0.5 M solution of sodium methoxide in methanol (13.2 mL, 6.6 mmol) was refluxed for 3 days before it was cooled to room temperature and concentrated in vacuo. The residue was dissolved in water (30 mL) and the solution was extracted with methyl tert-butyl ether (2×25 mL). The remaining aqueous layer was acidified to pH=3 with 1N HCl (10 mL). The resulting white precipitate was collected by filtration, washed with water and dried in vacuo to give the title compound as a white solid (82 mg): $^1$H NMR (DMSO-$d_6$, 200 MHz): δ=9.53 (t, 1H), 8.10 (d, J=9.0 Hz, 1H), 7.57 (m, 2H), 4.02 (d, J=6.2 Hz, 2H), 3.98 (s, 3H); MS: (+) m/z 302.00 (M+1).

Example 12

[(1-Cyano-4-hydroxy-6-phenoxy-isoquinoline-3-carbonyl)-amino]-acetic acid a. 1-Cyano-4-hydroxy-6-phenoxy-isoquinoline-3-carboxylic acid butyl ester

Synthesized from 1-bromo-4-hydroxy-6-phenoxy-isoquinoline-3-carboxylic acid butyl ester (prepared according to US 2004/0254215 A1 or scheme 2, $^1$H NMR (CDCl$_3$): δ=11.76 (s, 1H), 8.22 (d, 1H), 7.68 (d, 1H), 7.10 to 7.55 (m, 6H), 4.46 (t, 2H), 1.85 (m, 2H), 1.48 (m, 2H), 0.99 (t, 3H)) and CuCN in analogy to Example 3a.; MS-(−)-ion: M−1=361.3.

b. [(1-Cyano-4-hydroxy-6-phenoxy-isoquinoline-3-carbonyl)-amino]-acetic acid The title compound was obtained from 1-cyano-4-hydroxy-6-phenoxy-isoquinoline-3-carboxylic acid butyl ester and glycine in analogy to Example 1b.; MS-(−)-ion: M−1=362.1.

Example 13

{[1-Cyano-6-(4-fluoro-phenoxy)-4-hydroxy-isoquinoline-3-carbonyl]-amino}-acetic acid a. 1-Bromo-6-(4-fluoro-phenoxy)-4-hydroxy-isoquinoline-3-carboxylic acid butyl ester A mixture of 6-(4-fluoro-phenoxy)-1,4-dihydroxy-isoquinoline-3-carboxylic acid butyl ester (7.43 g, 20 mmol, prepared according to US 2004/0254215 A1 or scheme), POBr$_3$ (17.38 g, 60 mmol), and anhydrous acetonitrile (140 mL) was refluxed with stirring for 60 minutes before it was concentrated in vacuo. To the residue was added ethyl acetate (400 mL), NaHCO$_3$ (60 g), and then water in small portions (400 mL) with stirring. After stirring for 30 min at room temperature the mixture was filtered through a pad of celite. The organic phase of the filtrate was separated, and dried over MgSO$_4$. Then silica gel was added and the mixture was concentrated in vacuo. The residue was added on top of a short column filled with silica gel. Elution using CH$_2$Cl$_2$ as the solvent gave the title compound as an off-white solid (930 mg); $^1$H NMR (CDCl$_3$, 200 MHz): δ=11.76 (s, 1H), 8.22 (d, J=9.4 Hz, 1H), 7.61 (d, J=2.3 Hz, 1H), 7.50 (dd, J=9.0, 2.3 Hz, 1H), 7.10 to 7.13 (m, 4H), 4.46 (t, J=7.0 Hz, 2H), 1.85 (m, 2H), 1.45 (m, 2H), 0.99 (t, J=7.4 Hz, 3H).

b. 1-Cyano-6-(4-fluoro-phenoxy)-4-hydroxy-isoquinoline-3-carboxylic acid butyl ester Synthesized from 1-bromo-6-(4-fluoro-phenoxy)-4-hydroxy-isoquinoline-3-carboxylic acid butyl ester and CuCN in analogy to Example 3a.; MS-(−)-ion: M−1=379.2.

c. {[1-Cyano-6-(4-fluoro-phenoxy)-4-hydroxy-isoquinoline-3-carbonyl]-amino}-acetic acid The title compound was obtained from 1-cyano-6-(4-fluoro-phenoxy)-4-hydroxy-isoquinoline-3-carboxylic acid butyl ester and glycine in analogy to Example 1b.; MS-(−)-ion: M−1=380.0.

Example 14

{[1-Cyano-4-hydroxy-6-(4-methoxy-phenoxy)-isoquinoline-3-carbonyl]-amino}-acetic acid a. 1-Bromo-4-hydroxy-6-(4-methoxy-phenoxy)-isoquinoline-3-carboxylic acid butyl ester To mixture of 4-Hydroxy-6-(4-methoxy-phenoxy)-isoquinoline-3-carboxylic acid butyl ester (1.837 g, 5 mmol; for preparation, see example 28b) and N-bromosuccinimide (1.079 g, 6 mmol) was added anhydrous MeCN with stirring. After ca. 10 min another portion of MeCN (3 mL) was added and stirring continued for 20 min. The mixture was then partitioned between water (100 mL) and CCl$_4$ (100 mL). The organic phase was separated, dried over MgSO$_4$ and concentrated in vacuo. The residue was recrystallized from EtOAc to give the title compound as white needles (1.345 g); MS-(+)-ion: M+1, $^{79}$Br/$^{81}$Br=445.8 and 447.8.

b. 1-Cyano-4-hydroxy-6-(4-methoxy-phenoxy)-isoquinoline-3-carboxylic acid butyl ester The title compound was synthesized from 1-Bromo-4-hydroxy-6-(4-methoxy-phenoxy)-isoquinoline-3-carboxylic acid butyl ester and CuCN in analogy to example 3a; MS-(+)-ion: M+1=392.9.

c. {[1-Cyano-4-hydroxy-6-(4-methoxy-phenoxy)-isoquinoline-3-carbonyl]-amino}-acetic acid The title compound was synthesized from 1-Cyano-4-hydroxy-6-(4-methoxy-phenoxy)-isoquinoline-3-carboxylic acid butyl ester and glycine in analogy to example 1b; MS-(−)-ion: M−1=391.9.

Example 15

[(1-Cyano-4-hydroxy-6-phenylsulfanyl-isoquinoline-3-carbonyl)-amino]-acetic acid a. 1-Cyano-4-hydroxy-6-phenylsulfanyl-isoquinoline-3-carboxylic acid butyl ester The title compound was synthesized from 1-Bromo-4-hydroxy-6-phenylsulfanyl-isoquinoline-3-carboxylic acid butyl ester (prepared as shown in Scheme 2, according to US 2004/0254215 A1) and CuCN in analogy to example 3a; MS-(+)-ion: M+1=378.9.

b. [(1-Cyano-4-hydroxy-6-phenylsulfanyl-isoquinoline-3-carbonyl)-amino]-acetic acid The title compound was synthesized from 1-Cyano-4-hydroxy-6-phenylsulfanyl-isoquinoline-3-carboxylic acid butyl ester and glycine in analogy to example 1b; MS-(−)-ion: M−1=377.9.

Example 16

[(1-Cyano-4-hydroxy-7-phenylsulfanyl-isoquinoline-3-carbonyl)-amino]-acetic acid a. 1-Cyano-4-hydroxy-7-phenylsulfanyl-isoquinoline-3-carboxylic acid butyl ester The title compound was synthesized from 1-Bromo-4-hydroxy-7-phenylsulfanyl-isoquinoline-3-carboxylic acid butyl ester (prepared as shown in Scheme 2, according to US 2004/0254215 A1) and CuCN in analogy to example 3a; MS-(+)-ion: M+1=378.9.

b. [(1-Cyano-4-hydroxy-7-phenylsulfanyl-isoquinoline-3-carbonyl)-amino]-acetic acid The title compound was synthesized from 1-Cyano-4-hydroxy-7-phenylsulfanyl-isoquinoline-3-carboxylic acid butyl ester and glycine in analogy to example 1b; MS-(−)-ion: M−1=378.0.

Example 17

{[1-Cyano-6-(2,6-dimethyl-phenoxy)-4-hydroxy-isoquinoline-3-carbonyl]-amino}-acetic acid a. 4-(2,6-Dimethyl-phenoxy)-phthalonitrile

A mixture of 4-nitro-phthalonitrile (1 eq), 2,6-dimethylphenol (1.2 eq), $K_2CO_3$ (2 eq), and DMF (1 mL/mmol 4-nitro-phthalonitrile) was heated under nitrogen at 60° C. for 3 h with stirring After cooling to ambient temperature the mixture was poured into water (6 mL/mL DMF) with stirring. The mixture was extracted twice with EtOAc. The combined organic phases were dried over $MgSO_4$ and concentrated in vacuo. The residue was recrystallized from EtOH to give the title compound as a tan solid (yield: 87%); $^1$H NMR (CDCl$_3$, 200 MHz): δ=7.70 (d, 1H), 7.05 to 7.16 (m, 5H), 2.08 (s, 6H).

b. 4-(2,6-Dimethyl-phenoxy)-phthalic acid

A mixture of 4-(2,6-dimethyl-phenoxy)-phthalonitrile, aqueous KOH (45 wt % KOH; 0.5 mL/mmol), and MeOH (0.5 mL/mmol) was refluxed for 4 days with stirring before it was diluted with water (5 mL/mmol) and acidified by addition of concentrated hydrochloric acid. The resulting mixture was extracted with EtOAc. The organic phase was dried over $MgSO_4$ and concentrated in vacuo to give the title compound as a tan solid (yield: 99%); MS-(−)-ion: M−1=285.5.

c. [5-(2,6-Dimethyl-phenoxy)-1,3-dioxo-1,3-dihydro-isoindol-2-yl]-acetic acid 4-(2,6-Dimethyl-phenoxy)-phthalic acid and an equimolar amount of glycine were ground thoroughly together in a mortar. The mixture was then heated at 220 to 240° C. in an oil-bath in vacuo until the formation of water ceased (ca. 30 min) to give the title compound as a dark glass (yield: 99%); MS-(−)-ion: M−1=324.5.

d. [5-(2,6-Dimethyl-phenoxy)-1,3-dioxo-1,3-dihydro-isoindol-2-yl]-acetic acid methyl ester To a solution of [5-(2,6-Dimethyl-phenoxy)-1,3-dioxo-1,3-dihydro-isoindol-2-yl]-acetic acid in MeOH (1 mL/mmol) was added concentrated sulfuric acid (35 µl/mmol) and the mixture was refluxed with stirring for 16 h before it was diluted with water (6.5 mL/mmol) and extracted twice with EtOAc. The combined organic phases were washed with saturated $NaHCO_3$ solution, dried over $MgSO_4$, and concentrated in vacuo to give the title compound as a tan solid (yield: 96%); MS-(+)-ion: M+1=340.5.

e. 6-(2,6-Dimethyl-phenoxy)-1,4-dihydroxy-isoquinoline-3-carboxylic acid butyl ester Sodium (1 eq) was dissolved in n-butanol (1.6 mL/mmol) with stirring at 70° C. Subsequently, the temperature was raised to 95° C. before a solution of [5-(2,6-Dimethyl-phenoxy)-1,3-dioxo-1,3-dihydro-isoindol-2-yl]-acetic acid methyl ester (0.5 eq) in hot n-butanol (2.3 mL/mmol) was added in one portion with stirring. Stirring was continued at 95° C. for 3 h before the mixture was concentrated in vacuo. To the residue was added 2 N hydrochloric acid (1.3 eq) and EtOAc (ca. 4-fold volume) and the mixture was stirred vigorously for 45 min. Subsequently, the solid component was sucked off, washed with water and dried in vacuo before it was suspended in EtOAc (ca. 20 mL/g) and the mixture was refluxed with stirring for 2 h. After cooling to ambient temperature the solid component was sucked off, washed with EtOAc and dried in vacuo to give the title compound as an off-white solid (yield: 43%); MS-(+)-ion: M+1=382.5.

f. 1-Bromo-6-(2,6-dimethyl-phenoxy)-4-hydroxy-isoquinoline-3-carboxylic acid butyl ester A mixture of 6-(2,6-Dimethyl-phenoxy)-1,4-dihydroxy-isoquinoline-3-carboxylic acid butyl ester (4 mmol, 1.53 g), POBr$_3$ (16 mmol, 4.63 g), MeCN (30 mL) was refluxed gently with stirring before it was concentrated in vacuo. The residue was dissolved in $CH_2Cl_2$ (100 mL). To the solution was added $NaHCO_3$ (20 g) and then water (100 mL) in small portions with stirring. The mixture was stirred for 1 h at ambient temperature before the organic phase was separated and dried over $MgSO_4$. Concentration and purification of the residue by flash column chromatography on silica gel using $CH_2Cl_2$ as the eluent gave the title compound as a yellowish oil (640 mg); MS-(+)-ion: M+1, $^{79}$Br/$^{81}$Br=443.9 and 445.9.

g. 1-Cyano-6-(2,6-dimethyl-phenoxy)-4-hydroxy-isoquinoline-3-carboxylic acid butyl ester The title compound was synthesized from 1-Bromo-6-(2,6-dimethyl-phenoxy)-4-hydroxy-isoquinoline-3-carboxylic acid butyl ester and CuCN in analogy to example 3a; MS-(+)-ion: M+1=390.9.

h. {[1-Cyano-6-(2,6-dimethyl-phenoxy)-4-hydroxy-isoquinoline-3-carbonyl]-amino}-acetic acid The title compound was synthesized from 1-Cyano-6-(2,6-dimethyl-phenoxy)-4-hydroxy-isoquinoline-3-carboxylic acid butyl ester and glycine in analogy to example 1b; MS-(−)-ion: M−1=390.0.

Example 18

[(1-Cyano-4-hydroxy-5-phenoxy-isoquinoline-3-carbonyl)-amino]-acetic acid a. 2-Methyl-6-phenoxy-benzoic acid

2-Chloro-6-methyl-benzoic acid (30 mmol, 5.22 g) and phenol (40 mmol, 3.8 g) were dissolved in a solution of NaOMe (30 wt %) in MeOH (ca. 66 mmol, 12 mL). To the solution was added copper bronze (3 mmol, 193 mg) before it was concentrated in vacuo. Then, 1,2-dichlorobenzene (24 mL) was added and the mixture was refluxed under nitrogen for 2 h with stirring. After cooling to ambient temperature water (200 mL) and $Et_2O$ (150 mL) were added and the mixture was stirred vigorously for 30 min before the organic phase was separated and discarded. The aqueous phase was washed with $Et_2O$ (150 mL) before it was acidified by addition of 5 N hydrochloric acid. The resulting mixture was extracted with ethyl acetate (1×100 mL). The organic phase was dried over $MgSO_4$ and concentrated in vacuo. The residue was recrystallized from hexanes/toluene to give the title compound as a tan solid (4.55 g); MS-(−)-ion: M−1=226.8.

b. 2-Methyl-6-phenoxy-benzoic acid methyl ester

A mixture of 2-methyl-6-phenoxy-benzoic acid (19.9 mmol, 4.54 g), methanol (20 mL), and concentrated sulfuric acid (1.5 mL) was refluxed with stirring for 18 h before it was concentrated in vacuo. To the residue was added water (50 mL) and the mixture was neutralized by adding small portions of $NaHCO_3$ with stirring. Subsequently, the mixture was extracted with ethyl acetate (1×50 mL). The organic phase was dried over $MgSO_4$ and concentrated in vacuo. Purification of the residue by flash column chromatography on silica gel using hexanes:ethyl acetate=7:3 as the eluent gave the title compound as a yellowish oil (2.16 g); MS-(+)-ion: M+1=242.8.

c. 2-{[Methoxycarbonylmethyl-(toluene-4-sulfonyl)-amino]-methyl}-6-phenoxy-benzoic acid methyl ester A mixture of 2-methyl-6-phenoxy-benzoic acid methyl ester (8.9 mmol, 2.15 g), N-bromosuccinimide (9.1 mmol, 1.64 g), benzoyl peroxide (0.44 mmol, 110 mg), and $CCl_4$ (35 mL) was refluxed with stirring for 6 h. After cooling to ambient temperature the mixture was filtered and the filtrate was concentrated in vacuo to give a yellowish oil (3.01 g). The oil (3.00 g) was dissolved in dry DMF (8 mL). NaI (2.42 g), $K_2CO_3$ (2.21 g), and (toluene-4-sulfonylamino)-acetic acid methyl ester (2.04 g) were added and the mixture was stirred at ambient temperature for 18 h before water was added with stirring. The aqueous phase was then decanted from the oily precipitate formed. The oil was dissolved in ethyl acetate (70 mL) and the solution was washed with concentrated aqueous $NaHCO_3$ solution before it was dried over $MgSO_4$ and concentrated in vacuo to give the title compound as a dark oil (3.87 g). The crude product was used in the next step without further purification; MS-(+)-ion: M+23=506.0.

d. 4-Hydroxy-5-phenoxy-isoquinoline-3-carboxylic acid methyl ester

To a solution of crude 2-{[Methoxycarbonylmethyl-(toluene-4-sulfonyl)-amino]-methyl}-6-phenoxy-benzoic acid methyl ester (3.87 g) in methanol (24 mL) was added a solution of NaOMe (30 wt %) in methanol (4 mL) with stirring. After stirring for 3 days at ambient temperature the mixture was concentrated in vacuo. To the residue was added 1 N hydrochloric acid (20 mL) and the mixture was extracted with ethyl acetate (1×100 mL). The organic phase was then washed with concentrated aqueous $NaHCO_3$ solution (3×100 mL), dried over $MgSO_4$ and concentrated in vacuo. The residue was recrystallized from ethyl acetate to give the title compound as a yellowish solid (630 mg); MS-(+)-ion: M+1=295.8.

e. 1-Bromo-4-hydroxy-5-phenoxy-isoquinoline-3-carboxylic acid methyl ester

A mixture of 4-hydroxy-5-phenoxy-isoquinoline-3-carboxylic acid methyl ester (1.55 mmol, 458 mg), N-bromosuccinimide (1.7 mmol, 306 mg), benzoyl peroxide (0.08 mmol, 19 mg), and $CCl_4$ (10 mL) was refluxed with stirring for 2 h. After cooling to ambient temperature the mixture was filtered and the filtrate was concentrated in vacuo. The residue was purified by flash column chromatography on silica gel using hexanes:ethyl acetate=9:1 as the eluent to give the title compound as an off-white solid (225 mg); MS-(+)-ion: M+1, $^{79}Br/^{81}Br$=373.9 and 375.8.

f. 1-Cyano-4-hydroxy-5-phenoxy-isoquinoline-3-carboxylic acid methyl ester

The title compound was synthesized from 1-Bromo-4-hydroxy-5-phenoxy-isoquinoline-3-carboxylic acid methyl ester and CuCN in analogy to example 3a; MS-(+)-ion: M+1=320.8.

g. [(1-Cyano-4-hydroxy-5-phenoxy-isoquinoline-3-carbonyl)-amino]-acetic acid The title compound was synthesized from 1-Cyano-4-hydroxy-5-phenoxy-isoquinoline-3-carboxylic acid methyl ester and glycine in analogy to example 1b; MS-(+)-ion: M+1=363.9.

Example 19

{[1-Cyano-4-hydroxy-8-(4-methoxy-phenoxy)-isoquinoline-3-carbonyl]-amino}-acetic acid a. 3-Iodo-2-methyl-benzoic acid methyl ester

A mixture of 3-iodo-2-methyl-benzoic acid (90 mmol, 23.6 g), methanol (250 mL), and concentrated sulfuric acid (13 mL) was refluxed with stirring for 40 h before it was concentrated in vacuo. The residue was dissolved in ethyl acetate and the mixture was neutralized by adding small portions of a saturated aqueous $NaHCO_3$ solution with stirring. The organic phase was dried over $MgSO_4$ and concentrated in vacuo to give the title compound as a yellowish oil (24.3 g); $^1H$ NMR ($CDCl_3$, 200 MHz): δ=7.96 (d, 1H), 7.71 (d, 1H), 6.91 (t, 1H), 3.89 (s, 3H), 2.66 (s, 3H).

b. 3-Iodo-2-{[methoxycarbonylmethyl-(toluene-4-sulfonyl)-amino]-methyl}-benzoic acid methyl ester A mixture of 3-iodo-2-methyl-benzoic acid methyl ester (75 mmol, 20.7 g), N-bromosuccinimide (76.6 mmol, 13.8 g), benzoyl peroxide (890 mg), and $CCl_4$ (300 mL) was refluxed with stirring for 15 h. After cooling to ambient temperature the mixture was filtered and the filtrate was concentrated in vacuo to give the title compound as a tan oil. The oil (26.3 g) was dissolved in dry DMF (75 mL). NaI (22.4 g), $K_2CO_3$ (20.5 g), and (toluene-4-sulfonylamino)-acetic acid methyl ester (19 g) were added and the mixture was stirred at ambient temperature for 24 h before it was poured into water (900 mL). The mixture was extracted with ethyl acetate (2×250 mL). The combined organic phases were washed with a solution of sodium meta-bisulfite (20 g) in water (300 mL) and water (2×300 mL) before they were dried over $MgSO_4$ and concentrated in vacuo to give the title compound as a dark gum (38.1 g). The crude product was used in the next step without further purification; MS-(+)-ion: M+23=539.9.

c. 4-Hydroxy-8-iodo-isoquinoline-3-carboxylic acid methyl ester

To a solution of crude 3-Iodo-2-{[methoxycarbonylmethyl-(toluene-4-sulfonyl)-amino]-methyl}-benzoic acid methyl ester (37.8 g) in methanol (220 mL) was added a solution of NaOMe (30 wt %) in methanol (40 mL) with stirring. After stirring for 18 h at ambient temperature the mixture was concentrated in vacuo. To the residue was added 1 N hydrochloric acid (200 mL) and the mixture was extracted with hot ethyl acetate (1×300 mL). The organic phase was then washed with concentrated aqueous $NaHCO_3$ solution (3×200 mL), dried over $MgSO_4$ and concentrated in vacuo. The residue was recrystallized from ethyl acetate to give the title compound as a tan solid (10.1 g); MS-(+)-ion: M+1=329.8.

d. 4-Hydroxy-8-(4-methoxy-phenoxy)-isoquinoline-3-carboxylic acid methyl ester A mixture of 4-Hydroxy-8-iodo-isoquinoline-3-carboxylic acid methyl ester (7 mmol, 2.3 g), 4-methoxy-phenol (35 mmol, 4.39 g), $Cs_2CO_3$ (35 mmol, 11.42 g), 2,2,6,6-tetramethyl-heptane-3,5-dione (2.8 mmol, 0.59 mL), CuCl (7 mmol, 0.70 g), and anhydrous DMF (42 mL) was refluxed under nitrogen with stirring for 15 min. before it was poured into ethyl acetate (700 mL). Water (700 mL) and 5 N hydrochloric acid (5 mL) were added and the mixture was stirred for 15 min. The organic phase was then separated and washed with water (2×700 mL) before it was dried over $MgSO_4$ and concentrated in vacuo. Purification of the residue by flash column chromatography on silica gel using hexanes:EtOAc=75:25 as the eluent gave the title compound as a tan solid (234 mg); MS-(+)-ion: M+1=326.4.

e. 1-Bromo-4-hydroxy-8-(4-methoxy-phenoxy)-isoquinoline-3-carboxylic acid methyl ester A mixture of 4-hydroxy-8-(4-methoxy-phenoxy)-isoquinoline-3-carboxylic acid methyl ester (1.17 mmol, 381 mg), N-bromosuccinimide (1.3 mmol, 234 mg), benzoyl peroxide (0.06 mmol, 15 mg), and $CCl_4$ (8 mL) was refluxed with stirring for 2.5 h. After cooling to ambient temperature silica gel was added and the mixture was concentrated in vacuo. The residue was added on top of a chromatography column filled with silica gel. Elution with $CH_2Cl_2$ gave the title compound as a tan solid (403 mg); MS-(+)-ion: M+1, $^{79}$Br/$^{81}$Br=404.3 and 406.3.

f. 1-Cyano-4-hydroxy-8-(4-methoxy-phenoxy)-isoquinoline-3-carboxylic acid methyl ester The title compound was synthesized from 1-bromo-4-hydroxy-8-(4-methoxy-phenoxy)-isoquinoline-3-carboxylic acid methyl ester and CuCN in analogy to example 3a; MS-(+)-ion: M+1=351.4.

g. {[1-Cyano-4-hydroxy-8-(4-methoxy-phenoxy)-isoquinoline-3-carbonyl]-amino}-acetic acid The title compound was synthesized from 1-cyano-4-hydroxy-8-(4-methoxy-phenoxy)-isoquinoline-3-carboxylic acid methyl ester and glycine in analogy to example 1b; MS-(−)-ion: M−1=392.4.

Example 20

{[1-Cyano-4-hydroxy-8-(3-methoxy-phenoxy)-isoquinoline-3-carbonyl]-amino}-acetic acid a. 4-Hydroxy-8-(3-methoxy-phenoxy)-isoquinoline-3-carboxylic acid methyl ester The title compound was synthesized from 4-hydroxy-8-iodo-isoquinoline-3-carboxylic acid methyl ester and 3-methoxy-phenol in analogy to example 19d; MS-(+)-ion: M+1=326.4.

b. 1-Bromo-4-hydroxy-8-(3-methoxy-phenoxy)-isoquinoline-3-carboxylic acid methyl ester A mixture of 4-hydroxy-8-(3-methoxy-phenoxy)-isoquinoline-3-carboxylic acid methyl ester (1.75 mmol, 569 mg), N-bromosuccinimide (2 mmol, 360 mg), benzoyl peroxide (0.09 mmol, 22 mg), and $CCl_4$ (12 mL) was refluxed with stirring for 4 h. After cooling to ambient temperature the mixture was filtered, silica gel was added to the filtrate and the mixture was concentrated in vacuo. The residue was added on top of a chromatography column filled with silica gel. Elution with $CH_2Cl_2$ gave a yellowish solid (435 mg). A mixture of this solid (283 mg), CuCN (127 mg), and anhydrous DMF (2.8 mL) was refluxed with stirring under nitrogen for 15 min. After cooling to ambient temperature the mixture was diluted with ethyl acetate (200 mL). The resulting mixture was stirred for 15 min and then filtered through a pad of celite. The filtrate was washed with 0.1N hydrochloric acid (1×300 mL) and water (2×300 mL), and dried over $MgSO_4$. Subsequently, the mixture was concentrated in vacuo to give a tan solid (178 mg). A mixture of this solid (175 mg), sodium acetate (49 mg), Pd/C (10 wt % Pd, 50 wt % water; 100 mg), methanol (10 mL), and ethyl acetate (20 mL) was stirred under a hydrogen atmosphere (ambient pressure) for 18 h before it was filtered through a pad of celite. The filtrate was concentrated in vacuo. To the residue was added saturated aqueous $NaHCO_3$ solution (20 mL) and the mixture was extracted with ethyl acetate (1×40 mL). The organic phase was dried over $MgSO_4$ and concentrated in vacuo. Purification of the residue by flash column chromatography on silica gel using $CH_2Cl_2$: ethyl acetate=98:2 as the eluent gave the title compound as an off-white solid (101 mg); MS-(−)-ion: M−1=349.4.

c. {[1-Cyano-4-hydroxy-8-(3-methoxy-phenoxy)-isoquinoline-3-carbonyl]-amino}-acetic acid The title compound was synthesized from 1-cyano-4-hydroxy-8-(3-methoxy-phenoxy)-isoquinoline-3-carboxylic acid methyl ester and glycine in analogy to example 1b; MS-(−)-ion: M−1=392.4.

Example 21

{[1-Cyano-4-hydroxy-8-(2-methoxy-phenoxy)-isoquinoline-3-carbonyl]-amino}-acetic acid a. 4-Hydroxy-8-(2-methoxy-phenoxy)-isoquinoline-3-carboxylic acid methyl ester The title compound was synthesized from 4-hydroxy-8-iodo-isoquinoline-3-carboxylic acid methyl ester and 2-methoxy-phenol in analogy to example 19d; MS-(+)-ion: M+1=326.4.

b. 1-Bromo-4-hydroxy-8-(2-methoxy-phenoxy)-isoquinoline-3-carboxylic acid methyl ester The title compound was synthesized from 4-hydroxy-8-(2-methoxy-phenoxy)-isoquinoline-3-carboxylic acid methyl ester and N-bromosuccinimide in analogy to example 19e; MS-(+)-ion: M+1, $^{79}$Br/$^{81}$Br=404.3 and 406.3.

c. 1-Cyano-4-hydroxy-8-(2-methoxy-phenoxy)-isoquinoline-3-carboxylic acid methyl ester The title compound was synthesized from 1-bromo-4-hydroxy-8-(2-methoxy-phenoxy)-isoquinoline-3-carboxylic acid methyl ester and CuCN in analogy to example 3a; MS-(+)-ion: M+1=351.4.

d. {[1-Cyano-4-hydroxy-8-(2-methoxy-phenoxy)-isoquinoline-3-carbonyl]-amino}-acetic acid The title compound was synthesized from 1-cyano-4-hydroxy-8-(2-methoxy-phenoxy)-isoquinoline-3-carboxylic acid methyl ester and glycine in analogy to example 1b; MS-(−)-ion: M−1=392.5.

Example 22

[(7-Benzyl-1-cyano-4-hydroxy-isoquinoline-3-carbonyl)-amino]-acetic acid a. 5-Benzyl-3H-isobenzofuran-1-one

A mixture of 5-bromo-3H-isobenzofuran-1-one (14 mmol, 3.04 g), benzylzinc bromide solution (0.5 M in THF, 28 mmol, 56 mL), [1,1'bis(diphenylphosphino)-ferrocene]dichloropalladium(II) 1:1 complex with $CH_2Cl_2$ (0.07 mmol, 57 mg), and anhydrous 1,4-dioxane (70 mL) was refluxed with stirring under nitrogen for 40 h. After cooling to ambient temperature silica gel was added and the mixture was concentrated in vacuo. The residue was added on top of a chromatography column filled with silica gel. Elution with hexanes:ethyl acetate=9:1 gave a yellow solid. Further purification by recrystallization from ethyl acetate/hexanes gave the title compound (1.37 g) as white needles; $^1$H NMR (CDCl$_3$, 200 MHz): δ=7.83 (d, 1H), 7.16 to 7.39 (m, 7H), 5.26 (s, 2H), 4.11 (s, 2H).

b. 4-Benzyl-2-{[methoxycarbonylmethyl-(toluene-4-sulfonyl)-amino]-methyl}-benzoic acid methyl ester A mixture of 5-benzyl-3H-isobenzofuran-1-one (6 mmol, 1.35 g), boric acid (0.18 mmol, 11 mg), triphenylphosphine oxide (0.18 mmol, 51 mg), and thionyl chloride (7.8 mmol, 0.59 mL) was refluxed in an oil bath (bath temperature 130 to 140° C.) for 18 h with stirring. Subsequently, methanol (6 mL) was added and the mixture was stirred for 15 min before it was concentrated in vacuo. The residue was dissolved in ethyl acetate (40 mL). The solution was washed with saturated aqueous NaHCO$_3$ solution (2×20 mL), dried over MgSO$_4$ and was concentrated in vacuo to give a yellowish oil (1.51 g). The oil (906 mg) was dissolved in anhydrous DMF (5 mL). NaI (1.0 g), K$_2$CO$_3$ (912 mg), and (toluene-4-sulfonylamino)-acetic acid methyl ester (803 mg) were added and the mixture was stirred at ambient temperature for 15 h before it was poured into water (50 mL). Traces of iodine were removed by adding a small amount of sodium meta-bisulfite before extracting the mixture with ethyl acetate (1×50 mL). The organic phase was then washed with water (1×50 mL), dried over MgSO$_4$ and concentrated in vacuo to give the crude title compound as a dark gum (1.58 g) that was used in the next step without further purification; MS-(+)-ion: M+1=481.8.

c. 7-Benzyl-4-hydroxy-isoquinoline-3-carboxylic acid methyl ester

To a solution of crude 4-benzyl-2-{[methoxycarbonylmethyl-(toluene-4-sulfonyl)-amino]-methyl}-benzoic acid methyl ester (1.54 g) in methanol (1.75 mL) was added a solution of NaOMe (30 wt %) in methanol (1.75 mL) with stirring. After stirring for 5 h at ambient temperature the mixture was concentrated in vacuo and water (20 mL) was added. The pH of the mixture was adjusted to 7 to 8 by addition of 6N hydrochloric acid before the mixture was extracted with ethyl acetate (2×25 mL). The combined organic phases were then dried over MgSO$_4$ and concentrated in vacuo. The residue was purified by flash column chromatography on silica gel using hexanes:ethyl acetate=7:3 as the eluent to give the title compound as an off-white solid (451 mg); MS-(+)-ion: M+1=294.0.

d. 7-Benzyl-1-bromo-4-hydroxy-isoquinoline-3-carboxylic acid methyl ester

A mixture of 7-benzyl-4-hydroxy-isoquinoline-3-carboxylic acid methyl ester (1 mmol, 293 mg), N-bromosuccinimide (1.2 mmol, 214 mg) and anhydrous MeCN (10 mL) was stirred at ambient temperature for 4 days before silica gel was added and the mixture was concentrated in vacuo. The residue was added on top of a chromatography column filled with silica gel. Elution with hexanes:ethyl acetate=75:25 gave the title compound as an off-white solid (48 mg); MS-(+)-ion: M+1, $^{79}$Br/$^{81}$Br=372.4 and 374.4.

e. 7-Benzyl-1-cyano-4-hydroxy-isoquinoline-3-carboxylic acid methyl ester

The title compound was synthesized from 7-benzyl-1-bromo-4-hydroxy-isoquinoline-3-carboxylic acid methyl ester and CuCN in analogy to example 3a; MS-(−)-ion: M−1=317.4.

f. [(7-Benzyl-1-cyano-4-hydroxy-isoquinoline-3-carbonyl)-amino]-acetic acid The title compound was synthesized from 7-benzyl-1-cyano-4-hydroxy-isoquinoline-3-carboxylic acid methyl ester and glycine in analogy to example 1b; MS-(−)-ion: M−1=360.5.

Example 23

{[1-Cyano-5-(4-fluoro-phenoxy)-4-hydroxy-isoquinoline-3-carbonyl]-amino}-acetic acid a. 2-(4-Fluoro-phenoxy)-6-methyl-benzoic acid

The title compound was synthesized from 2-chloro-6-methyl-benzoic acid and 4-fluorophenol in analogy to example 18a; MS-(−)-ion: M−1=245.5.

b. 2-(4-Fluoro-phenoxy)-6-methyl-benzoic acid methyl ester

A mixture of 2-(4-fluoro-phenoxy)-6-methyl-benzoic acid (21.6 mmol, 5.32 g), dimethylsulfate (43.2 mmol, 4.2 mL), $K_2CO_3$ (43.2 mmol, 6 g), and diethyl ketone (80 mL) was refluxed with stirring for 18 h before it was concentrated in vacuo. To the residue was added water (50 mL) and the mixture was extracted with ethyl acetate (1×100 mL). The organic phase was dried over $MgSO_4$ and concentrated in vacuo to give the title compound as a tan oil (5.5 g); $^1$H NMR ($CDCl_3$, 200 MHz): δ=7.20 (t, 1H), 6.92 to 7.04 (m, 5H), 6.66 (d, 1H), 3.84 (s, 3H), 2.35 (s, 3H).

c. 2-(4-Fluoro-phenoxy)-6-{[methoxycarbonylmethyl-(toluene-4-sulfonyl)-amino]-methyl}-benzoic acid methyl ester The crude title compound was synthesized from 2-(4-fluoro-phenoxy)-6-methyl-benzoic acid methyl ester, N-bromosuccinimide, and (toluene-4-sulfonylamino)-acetic acid methyl ester in analogy to example 18c and was used in the following step without further purification; MS-(+)-ion: M+23=524.4.

d. 5-(4-Fluoro-phenoxy)-4-hydroxy-isoquinoline-3-carboxylic acid methyl ester The title compound was synthesized from crude 2-(4-fluoro-phenoxy)-6-{[methoxycarbonylmethyl-(toluene-4-sulfonyl)-amino]-methyl}-benzoic acid methyl ester in analogy to example 18d; MS-(+)-ion: M+1=314.4.

e. 1-Bromo-5-(4-fluoro-phenoxy)-4-hydroxy-isoquinoline-3-carboxylic acid methyl ester The title compound was synthesized from 5-(4-fluoro-phenoxy)-4-hydroxy-isoquinoline-3-carboxylic acid methyl ester and N-bromosuccinimide in analogy to example 18e; MS-(+)-ion: M+1, $^{79}$Br/$^{81}$Br=392.4 and 394.3.

f. 1-Cyano-5-(4-fluoro-phenoxy)-4-hydroxy-isoquinoline-3-carboxylic acid methyl ester The title compound was synthesized from 1-bromo-5-(4-fluoro-phenoxy)-4-hydroxy-isoquinoline-3-carboxylic acid methyl ester and CuCN in analogy to example 3a; MS-(−)-ion: M−1=337.4.

g. {[1-Cyano-5-(4-fluoro-phenoxy)-4-hydroxy-isoquinoline-3-carbonyl]-amino}-acetic acid The title compound was synthesized from 1-cyano-5-(4-fluoro-phenoxy)-4-hydroxy-isoquinoline-3-carboxylic acid methyl ester and glycine in analogy to example 1b; MS-(−)-ion: M−1=380.4.

Example 24

{[1-Cyano-7-(2,6-dimethyl-phenoxy)-4-hydroxy-isoquinoline-3-carbonyl]-amino}-acetic acid a. 1-Cyano-7-(2,6-dimethyl-phenoxy)-4-hydroxy-isoquinoline-3-carboxylic acid butyl ester Synthesized from 1-bromo-7-(2,6-dimethyl-phenoxy)-4-hydroxy-isoquinoline-3-carboxylic acid butyl ester (for synthesis, see US 2004/0254215 A1) and CuCN in analogy to Example 3a; MS-(−)-ion: M−1=389.5.

b. {[1-Cyano-7-(2,6-dimethyl-phenoxy)-4-hydroxy-isoquinoline-3-carbonyl]-amino}-acetic acid The title compound was obtained from 1-cyano-7-(2,6-dimethyl-phenoxy)-4-hydroxy-isoquinoline-3-carboxylic acid butyl ester and glycine in analogy to Example 1b; MS-(−)-ion: M−1=390.5.

Example 25

{[1-Cyano-6-(2-ethyl-6-methyl-phenoxy)-4-hydroxy-isoquinoline-3-carbonyl]-amino}-acetic acid a. 4-(2-Ethyl-6-methyl-phenoxy)-phthalonitrile

The title compound was obtained from 4-nitro-phthalonitrile and 2-ethyl-6-methyl-phenol in analogy to example 17a; MS-(+)-ion: M+1=263.5.

b. 4-(2-Ethyl-6-methyl-phenoxy)-phthalic acid

The title compound was obtained from 4-(2-Ethyl-6-methyl-phenoxy)-phthalonitrile in analogy to example 17b; MS-(−)-ion: M−1=299.4.

c. [5-(2-Ethyl-6-methyl-phenoxy)-1,3-dioxo-1,3-dihydro-isoindol-2-yl]-acetic acid The title compound was obtained from 4-(2-Ethyl-6-methyl-phenoxy)-phthalic acid and glycine in analogy to example 17c; MS-(−)-ion: M−1=338.4.

d. [5-(2-Ethyl-6-methyl-phenoxy)-1,3-dioxo-1,3-dihydro-isoindol-2-yl]-acetic acid methyl ester The title compound was obtained from [5-(2-Ethyl-6-methyl-phenoxy)-1,3-dioxo-1,3-dihydro-isoindol-2-yl]-acetic acid and methanol in analogy to example 17d; MS-(+)-ion: M+1=354.4.

e. 6-(2-Ethyl-6-methyl-phenoxy)-1,4-dihydroxy-isoquinoline-3-carboxylic acid butyl ester To a solution of [5-(2-Ethyl-6-methyl-phenoxy)-1,3-dioxo-1,3-dihydro-isoindol-2-yl]-acetic acid methyl ester (22 mmol, 7.77 g) in anhydrous n-butanol (150 mL) was added a 1 N solution of sodium in n-butanol (45 mmol, 45 mL) at 95° C. in one portion with stirring. Stirring was continued at 95° C. for 3 h before the mixture was concentrated in vacuo. To the residue was added 2 N hydrochloric acid (60 mmol, 30 mL) and EtOAc (150 mL) and the mixture was stirred vigorously for 45 min. Subsequently, the solid component was sucked off, washed with water and dried in vacuo to give the title compound as a tan solid (623 mg); MS-(+)-ion: M+1=396.5.

f. 1-Bromo-6-(2-ethyl-6-methyl-phenoxy)-4-hydroxy-isoquinoline-3-carboxylic acid butyl ester A mixture of 6-(2-Ethyl-6-methyl-phenoxy)-1,4-dihydroxy-isoquinoline-3-carboxylic acid butyl ester (2.83 mmol, 1.12 g), $POBr_3$ (11 mmol, 3.19 g), MeCN (20 mL) was refluxed gently with stirring for 1 h before it was concentrated in vacuo. The residue was dissolved in $CHCl_3$ (50 mL). Water (10 mL) and subsequently small portions of $NaHCO_3$ (6 g) were added with stirring. The mixture was stirred for 30 min at ambient temperature before it was filtered through a pad of celite. The filtrate was dried over $MgSO_4$. Concentration and purification of the residue by flash column chromatography on silica gel using $CH_2Cl_2$ as the eluent gave the title compound as a tan oil (450 mg); MS-(+)-ion: M+1, $^{79}Br/^{81}Br$=458.4 and 460.6.

g. 1-Cyano-6-(2-ethyl-6-methyl-phenoxy)-4-hydroxy-isoquinoline-3-carboxylic acid butyl ester The title compound was synthesized from 1-Bromo-6-(2-ethyl-6-methyl-phenoxy)-4-hydroxy-isoquinoline-3-carboxylic acid butyl ester and CuCN in analogy to example 3a; MS-(−)-ion: M−1=403.5.

h. {[1-Cyano-6-(2-ethyl-6-methyl-phenoxy)-4-hydroxy-isoquinoline-3-carbonyl]-amino}-acetic acid The title compound was synthesized from 1-Cyano-6-(2-ethyl-6-methyl-phenoxy)-4-hydroxy-isoquinoline-3-carboxylic acid butyl ester and glycine in analogy to example 1b; MS-(−)-ion: M−1=404.4.

Example 26

{[1-Cyano-4-hydroxy-6-(2,4,6-trimethyl-phenoxy)-isoquinoline-3-carbonyl]-amino}-acetic acid a. 4-(2,4,6-Trimethyl-phenoxy)-phthalonitrile The title compound was obtained from 4-nitro-phthalonitrile and 2,4,6-trimethylphenol in analogy to example 17a; MS-(−)-ion: M−1=261.5.

b. 4-(2,4,6-Trimethyl-phenoxy)-phthalic acid

The title compound was obtained from 4-(2,4,6-trimethyl-phenoxy)-phthalonitrile in analogy to example 17b; MS-(−)-ion: M−1=299.4.

c. [1,3-Dioxo-5-(2,4,6-trimethyl-phenoxy)-1,3-dihydro-isoindol-2-yl]-acetic acid The title compound was obtained from 4-(2,4,6-trimethyl-phenoxy)-phthalic acid and glycine in analogy to example 17c; MS-(−)-ion: M−1=338.4.

d. [1,3-Dioxo-5-(2,4,6-trimethyl-phenoxy)-1,3-dihydro-isoindol-2-yl]-acetic acid methyl ester The title compound was obtained from [1,3-dioxo-5-(2,4,6-trimethyl-phenoxy)-1,3-dihydro-isoindol-2-yl]-acetic acid and methanol in analogy to example 17d; MS-(+)-ion: M+1=354.4.

e. 1,4-Dihydroxy-6-(2,4,6-trimethyl-phenoxy)-isoquinoline-3-carboxylic acid butyl ester The title compound was obtained from [1,3-dioxo-5-(2,4,6-trimethyl-phenoxy)-1,3-dihydro-isoindol-2-yl]-acetic acid methyl ester in analogy to example 25e; MS-(+)-ion: M+1=396.4.

f. 1-Bromo-4-hydroxy-6-(2,4,6-trimethyl-phenoxy)-isoquinoline-3-carboxylic acid butyl ester The title compound was obtained from 1,4-dihydroxy-6-(2,4,6-trimethyl-phenoxy)-isoquinoline-3-carboxylic acid butyl ester and $POBr_3$ in analogy to example 25f; MS-(+)-ion: M+1, $^{79}Br/^{81}Br$=458.4 and 460.4.

g. 1-Cyano-4-hydroxy-6-(2,4,6-trimethyl-phenoxy)-isoquinoline-3-carboxylic acid butyl ester The title compound was synthesized from 1-bromo-4-hydroxy-6-(2,4,6-trimethyl-phenoxy)-isoquinoline-3-carboxylic acid butyl ester and CuCN in analogy to example 3a; MS-(−)-ion: M−1=403.4.

h. {[1-Cyano-4-hydroxy-6-(2,4,6-trimethyl-phenoxy)-isoquinoline-3-carbonyl]-amino}-acetic acid The title compound was synthesized from 1-cyano-4-hydroxy-6-(2,4,6-trimethyl-phenoxy)-isoquinoline-3-carboxylic acid butyl ester and glycine in analogy to example 1b; MS-(−)-ion: M−1=404.4.

Example 27

{[6-(4-Chloro-2,6-dimethyl-phenoxy)-1-cyano-4-hydroxy-isoquinoline-3-carbonyl]-amino}-acetic acid a. 4-(4-Chloro-2,6-dimethyl-phenoxy)-phthalonitrile The title compound was obtained from 4-nitro-phthalonitrile and 4-chloro-2,6-dimethyl-phenol in analogy to example 17a; MS-(+)-ion: M+1=283.4.

b. 4-(4-Chloro-2,6-dimethyl-phenoxy)-phthalic acid

The title compound was obtained from 4-(4-chloro-2,6-dimethyl-phenoxy)-phthalonitrile in analogy to example 17b; MS-(−)-ion: M−1=319.4.

c. [5-(4-Chloro-2,6-dimethyl-phenoxy)-1,3-dioxo-1,3-dihydro-isoindol-2-yl]-acetic acid The title compound was obtained from 4-(4-chloro-2,6-dimethyl-phenoxy)-phthalic acid and glycine in analogy to example 17c; MS-(−)-ion: M−1=358.4.

d. [5-(4-Chloro-2,6-dimethyl-phenoxy)-1,3-dioxo-1,3-dihydro-isoindol-2-yl]-acetic acid methyl ester The title compound was obtained from [5-(4-chloro-2,6-dimethyl-phenoxy)-1,3-dioxo-1,3-dihydro-isoindol-2-yl]-acetic acid and methanol in analogy to example 17d; MS-(−)-ion: M−1=372.4.

e. 6-(4-Chloro-2,6-dimethyl-phenoxy)-1,4-dihydroxy-isoquinoline-3-carboxylic acid butyl ester The title compound was obtained from [5-(4-chloro-2,6-dimethyl-phenoxy)-1,3-dioxo-1,3-dihydro-isoindol-2-yl]-acetic acid methyl ester in analogy to example 25e; MS-(+)-ion: M+1=416.4.

f. 1-Bromo-6-(4-chloro-2,6-dimethyl-phenoxy)-4-hydroxy-isoquinoline-3-carboxylic acid butyl ester The title compound was obtained from 6-(4-chloro-2,6-dimethyl-phenoxy)-1,4-dihydroxy-isoquinoline-3-carboxylic acid butyl ester and $POBr_3$ in analogy to example 25f, MS-(+)-ion: M+1, $^{79}Br/^{81}Br$=478.3 and 480.3.

g. 6-(4-Chloro-2,6-dimethyl-phenoxy)-1-cyano-4-hydroxy-isoquinoline-3-carboxylic acid butyl ester The title compound was synthesized from 1-bromo-6-(4-chloro-2,6-dimethyl-phenoxy)-4-hydroxy-isoquinoline-3-carboxylic acid butyl ester and CuCN in analogy to example 3a; MS-(−)-ion: M−1=423.4.

h. {[6-(4-Chloro-2,6-dimethyl-phenoxy)-1-cyano-4-hydroxy-isoquinoline-3-carbonyl]-amino}-acetic acid The title compound was synthesized from 6-(4-Chloro-2,6-dimethyl-phenoxy)-1-cyano-4-hydroxy-isoquinoline-3-carboxylic acid butyl ester and glycine in analogy to example 1b; MS-(−)-ion: M−1=424.3.

Example 28

{[1-Cyano-4-hydroxy-7-(4-methoxy-phenoxy)-isoquinoline-3-carbonyl]-amino}-acetic acid a) 6- and 7-(4-Methoxy-phenoxy)-1-chloro-4-hydroxy-isoquinoline-3-carboxylic acid butyl ester $POCl_3$ (1.2 g, 7.8 mmol) was added to a mixture of 6- and 7-(4-methoxy-phenoxy)-1,4-dihydroxy-isoquinoline-3-carboxylic acid butyl ester (see U.S. Patent Application Publication No. 2004/02542.15) (3.0 g, 7.8 mmol) in anhydrous toluene (40 mL). Resulting mixture was microwaved at 130° C. for 15 min (ramp time 20 min). Reaction mixture was concentrated and carefully quenched with saturated $NaHCO_3$ solution (150 mL). After stirred at room temperature for 10 min, it was extracted with EtOAc (2×200 mL). Combined organic layers were washed with water and brine, dried over $MgSO_4$, filtered, and concentrated to give a mixture of the title compounds (2.4 g). MS-(+)-ion: M+1=402.25.

b) 7-(4-Methoxy-phenoxy)-4-hydroxy-isoquinoline-3-carboxylic acid butyl ester

To a solution of a 6- and 7-(4-methoxy-phenoxy)-1-chloro-4-hydroxy-isoquinoline-3-carboxylic acid butyl ester mixture (10 g, 24.9 mmol) in EtOAc (160 mL) was added 10% Pd/C (50% wet) (3.7 g) and then ammonium formate (15.7 g, 249 mmol). Resulting mixture was refluxed for 4 h. After cooled, it was diluted with EtOAc (100 mL) and then filtered. Filtrate was concentrated and residue was purified by silica gel chromatography (eluting with 20%-80% ethyl acetate in hexanes) to provide the title compound (3.2 g); MS-(+)-ion: M+1=368.16. In addition, 6-(4-methoxy-phenoxy)-4-hydroxy-isoquinoline-3-carboxylic acid butyl ester, was also isolated (5.04 g). MS-(+)-ion: M+1=368.17.

c) 1-Bromo-4-hydroxy-7-(4-methoxy-phenoxy)-isoquinoline-3-carboxylic acid butyl ester To a solid mixture of 7-(4-methoxy-phenoxy)-4-hydroxy-isoquinoline-3-carboxylic acid butyl ester (305 mg, 0.83 mmol) and N-bromosuccinimide (162 mg, 0.91 mmol) cooled with an ice bath was added acetonitrile (6 mL). Resulting mixture was stirred at 0° C. for 1.5 h and was concentrated. The residue was purified by silica gel chromatography (eluting with 10%-40% ethyl acetate in hexanes) to provide the title compound (217 mg). $^1$H NMR (200 MHz, $CDCl_3$) δ 11.88 (s, 1H), 8.32 (d, J=9.0 Hz, 1H), 7.54 (d, J=2.4 Hz, 1H), 7.46 (dd, J=9.0, 2.4 Hz, 1H), 7.08 (d, J=9.4 Hz, 2H), 6.95 (d, J=9.8 Hz, 2H), 4.46 (t, J=7.0 Hz, 2H), 3.85 (s, 3H), 1.85 (m, 2H), 1.47 (m, 2H), 0.98 (t, J=7.4 Hz, 3H).

d) 1-Cyano-4-hydroxy-7-(4-methoxy-phenoxy)-isoquinoline-3-carboxylic acid butyl ester A mixture of 1-bromo-4-hydroxy-7-(4-methoxy-phenoxy)-isoquinoline-3-carboxylic acid butyl ester (190 mg, 0.43 mmol), copper(I) cyanide (76.3 mg, 0.85 mmol) and N-methyl-pyrrolidine (3 mL) was heated at 130° C. for 1 h. After cooled, reaction mixture was partitioned between ethyl acetate and water. Organic layer was washed with brine, dried over magnesium sulfate, filtered, and concentrated. Crude product was purified by silica gel chromatography (eluting with 2%-25% ethyl acetate in methylene chloride) to give the title compound (129 mg). MS-(+)-ion: M+1=392.80.

e) {[1-Cyano-4-hydroxy-7-(4-methoxy-phenoxy)-isoquinoline-3-carbonyl]-amino}-acetic acid A mixture of 1-cyano-4-hydroxy-7-(4-methoxy-phenoxy)-isoquinoline-3-carboxylic acid butyl ester (110 mg, 0.28 mmol) and glycine (275 mg, 2.82 mmol) in a solution of sodium methoxide (0.5 M in methanol; 5.7 mL) was refluxed overnight. Reaction mixture was concentrated and dissolved in water (50 mL). It was washed with ethyl acetate (10 mL). Aqueous layer was acidified by 1 N HCl to pH=3-4 and extracted with ethyl acetate. Organic layer was washed with brine, dried over magnesium sulfate, filtered, and concentrated. Crude product was triturated with methanol (3 mL) and solid was collected and dried to give the title compound (72 mg). MS-(+)-ion: M+1=394.32.

Example 29

[(1-Cyano-6-cyclohexyloxy-4-hydroxy-isoquinoline-3-carbonyl)-amino]-acetic acid a) 1-Cyano-6-cyclohexyloxy-4-hydroxy-isoquinoline-3-carboxylic acid butyl ester A mixture of 1-bromo-6-cyclohexyloxy-4-hydroxy-isoquinoline-3-carboxylic acid butyl ester (see U.S. Patent Application Publication No. 2004/0254215; 350 mg, 0.83 mmol), CuCN (149 mg, 1.66 mmol) and N-methyl-pyrrolidine (2.5 mL) was heated at 130° C. for 2 h. After cooled, reaction mixture was poured into water (50 mL) with stirring. Precipitate was collected and rinsed with water. Resulting solid was partitioned between ethyl acetate and 10% aqueous $NH_4OH$ (50 mL), and vigorously stirred for 15 min. The mixture was acidified by aqueous concentrated HCl and then 1 N HCl solution to pH=4. The organic phase was separated and the aqueous phase was extracted with ethyl acetate. Combined organic layers were washed with brine, dried over magnesium sulfate, filtered and concentrated to give the title product (234 mg). MS-(+)-ion: M+1=369.43.

b) [(1-Cyano-6-cyclohexyloxy-4-hydroxy-isoquinoline-3-carbonyl)-amino]-acetic acid Prepared from 1-Cyano-6-cyclohexyloxy-4-hydroxy-isoquinoline-3-carboxylic acid butyl ester and glycine in analogy to example 28e (94% yield). MS-(+)-ion: M+1=370.32.

Example 30

[(6-Benzenesulfonyl-1-cyano-4-hydroxy-isoquinoline-3-carbonyl)-amino]-acetic acid a) 6-Benzenesulfonyl-1-bromo-4-hydroxy-isoquinoline-3-carboxylic acid butyl ester To a mixture of 6-benzenesulfonyl-4-hydroxy-isoquinoline-3-carboxylic acid butyl ester (100 mg, 0.26 mmol; see U.S. Patent Application Publication No. 2004/0254215) and benzene (4.5 mL) was added benzoyl peroxide (6.3 mg, 0.026 mmol). Resulting mixture was refluxed for 15 min. prior to the addition of N-bromosuccinimide (51 mg, 0.29 mmol). Reaction mixture was refluxed overnight. It was concentrated and the crude product was purified by silica gel chromatography (eluting with 20%-80%) ethyl acetate/hexanes to provide the title compound (91 mg). MS-(+)-ion: M+1=466.18, 464.14.

b) 6-Benzenesulfonyl-1-cyano-4-hydroxy-isoquinoline-3-carboxylic acid butyl ester Prepared from 6-benzenesulfonyl-1-bromo-4-hydroxy-isoquinoline-3-carboxylic acid butyl ester and CuCN in analogy to example 29a. Crude product was purified by silica gel chromatography (2%-20% ethyl acetate in methylene chloride) to give the title compound (49% yield). MS-(+)-ion: M+1=411.30.

c) [(6-Benzenesulfonyl-1-cyano-4-hydroxy-isoquinoline-3-carbonyl)-amino]-acetic acid Prepared from 6-benzenesulfonyl-1-cyano-4-hydroxy-isoquinoline-3-carboxylic acid butyl ester and glycine in analogy to example 28e (56% yield). MS-(+)-ion: M+1=412.26.

Example 31

{[1-Cyano-4-hydroxy-6-(4-propoxy-phenoxy)-isoquinoline-3-carbonyl]-amino}-acetic acid a) 4-(4-Benzyloxy-phenoxy)-phthalonitrile A mixture of 4-benzyloxyphenol (14.53 g, 72.6 mmol), 4-nitrophthalonitrile (10.47 g, 60.5 mmol), potassium carbonate (16.69 g, 120.9 mmol), and acetone (170 mL) was refluxed overnight; the reaction mixture was cooled, and the solids were filtered off and rinsed with EtOAc. All liquids were combined and concentrated in vacuo. The resulting residue was partitioned between EtOAc and 2 M NaOH solution in a 500-mL separation funnel. The organic phase was subsequently washed with 1 M HCl, saturated NaCl solution, dried over sodium sulfate, and concentrated in vacuo to give the crude title compound (22.1 g) that was used in the next step without further purification. $^1$H NMR (200 MHz, CDCl$_3$): δ (ppm)=7.7-6.6 (m, 12H), 5.08 (s, 2H).

b) 4-(4-Benzyloxy-phenoxy)-phthalic acid

A mixture of 4-(4-benzyloxy-phenoxy)-phthalonitrile (22.1 g), KOH (50 mL, 45 wt % in water), and MeOH (50 mL) was refluxed for 3 days. Then water was added and the resulting solution was acidified to pH 3-4 with 6 M HCl. The precipitate formed was collected by filtration, washed with water, and subsequently dried in vacuo to give the crude title compound as solid (23.5 g) that was used in the next step without further purification. $^1$H NMR (200 MHz, DMSO-d6): δ (ppm)=7.7-6.6 (m, 12H), 5.10 (s, 2H).

c) [5-(4-Benzyloxy-phenoxy)-1,3-dioxo-1,3-dihydro-isoindol-2-yl]-acetic acid ethyl ester and [5-(4-Hydroxy-phenoxy)-1,3-dioxo-1,3-dihydro-isoindol-2-yl]-acetic acid ethyl ester A mixture of 4-(4-Benzyloxy-phenoxy)-phthalic acid (23.5 g, 60.47 mmol) and ethyl glycine HCl salt (8.44 g, 60.47 mmol) was melted with a heating mantle and stirred for 30 min. Then while the mixture was hot, dichloromethane was added to give a solution. After cooling the solution was passed through a plug of silica gel. Elution was continued with a mixture of EtOAc and dichloromethate (1:1, v/v). The combined fractions were concentrated in vacuo to give a brown oil, which was purified by column chromatography to give the two title compounds: [5-(4-benzyloxy-phenoxy)-1,3-dioxo-1,3-dihydro-isoindol-2-yl]-acetic acid ethyl ester (9.41 g) and [5-(4-hydroxy-phenoxy)-1,3-dioxo-1,3-dihydro-isoindol-2-yl]-acetic acid ethyl ester (8.6 g). [5-(4-Benzyloxy-phenoxy)-1,3-dioxo-1,3-dihydro-isoindol-2-yl]-acetic acid ethyl ester: $^1$H NMR (200 MHz, CDCl$_3$): δ (ppm)=7.9-7.2 (m, 12H), 5.07 (s, 2H), 4.38 (s, 2H), 4.21 (q, 2H, J=7.2 Hz), 1.27 (t, 3H, J=7.2 Hz); [5-(4-Hydroxy-phenoxy)-1,3-dioxo-1,3-dihydro-isoindol-2-yl]-acetic acid ethyl ester: $^1$H NMR (200 MHz, CDCl$_3$): δ (ppm)=7.9-7.2 (m, 12H), 4.40 (s, 2H), 4.21 (q, 2H, J=7.2 Hz), 1.28 (t, 3H, J=7.2 Hz);

d) [1,3-Dioxo-5-(4-propoxy-phenoxy)-1,3-dihydro-isoindol-2-yl]-acetic acid ethyl ester A mixture of [5-(4-hydroxy-phenoxy)-1,3-dioxo-1,3-dihydro-isoindol-2-yl]-acetic acid ethyl ester (2.479 g, 7.26 mmol), 1-bromopropane (1.32 mL, 14.52 mmol), potassium carbonate (2.01 g, 14.52 mmol), and acetone (25 mL) was refluxed overnight. After cooling to ambient temperature the mixture was concentrated in vacuo and the residue was partitioned between EtOAc and water. The organic phase was washed with saturated NaCl, dried over anhydrous sodium sulfate, and concentrated in vacuo to give the title compound (2.485 g). $^1$H NMR (200 MHz, CDCl$_3$): δ (ppm)=7.77 (q, 1H, J=8.1 Hz), 7.3-6.8 (m, 6H), 4.38 (s, 2H), 4.20 (q, 2H, J=7.0 Hz), 3.93 (t, 2H, J=6.4 Hz), 1.82 (q, 2H, 6.6 Hz), 1.28 (t, 3H, J=7.0 Hz), 1.06 (t, 3H, J=7.5 Hz).

e) 4-Hydroxy-1-oxo-6-(4-propoxy-phenoxy)-1,2-dihydro-isoquinoline-3-carboxylic acid butyl ester A mixture of [1,3-dioxo-5-(4-propoxy-phenoxy)-1,3-dihydro-isoindol-2-yl]-acetic acid ethyl ester (2.485 g, 6.48 mmol), sodium butoxide, and butanol (14.3 mmol, 27 mL butanol) was heated at 90° C. to 100° C. for 2 h. Then the f) 1-Bromo-4-hydroxy-6-(4-propoxy-phenoxy)-isoquinoline-3-carboxylic acid butyl ester A mixture of 4-hydroxy-1-oxo-6-(4-propoxy-phenoxy)-1,2-dihydro-isoquinoline-3-carboxylic acid butyl ester (495 mg, 1.20 mmol), POBr$_3$ (379 mg, 1.32 mmol), and toluene was microwaved at 110° C. for 25 min. Subsequently, the mixture was diluted with EtOAc, washed with aqueous NaHCO$_3$ and saturated NaCl solution before it was dried over anhydrous sodium sulfate and concentrated in vacuo to give the crude title product (509 mg) that was used in the next step without further purification. $^1$H NMR (200 MHz, CDCl$_3$): δ (ppm)=11.74 (s, 1H), 8.19 (d, 1H, J=9.2 Hz), 7.60-7.46 (m, 2H), 7.07-6.92 (m, 4H), 4.46 (t, 2H, =7.1 Hz), 3.94 (t, 2H, J=6.6 Hz), 1.83 (m, 4H), 1.45 (m, 2H), 1.10-0.94 (m, 6H).

g) 1-Cyano-4-hydroxy-6-(4-propoxy-phenoxy)-isoquinoline-3-carboxylic acid butyl ester A mixture of 1-bromo-4-hydroxy-6-(4-propoxy-phenoxy)-isoquinoline-3-carboxylic acid butyl ester (315 mg, 0.664 mmol), CuCN (66 mg, 0.730 mmol), and N-methylpyrrolidinone (2 mL) was stirred at 120° C. for 4 h. After cooling to room temperature the mixture was poured into EtOAc (20 mL) and saturated ammonium hydroxide solution (~1 mL) was added. The mixture was rapidly stirred for 2 min. Then it was acidified with concentrated HCl, washed with water, and saturated NaCl solution before it was dried over anhydrous sodium sulfate, and concentrated in vacuo. The residue was purified by column chromatography to give title compound (206 mg). ESI MS (m/z): 421 (M+H$^+$).

h) {[1-Cyano-4-hydroxy-6-(4-propoxy-phenoxy)-isoquinoline-3-carbonyl]-amino}-acetic acid A mixture of 1-cyano-4-hydroxy-6-(4-propoxy-phenoxy)-isoquinoline-3-carboxylic acid butyl ester (200 mg, 0.422 mmol), glycine (633 mg, 8.43 mmol) and NaOMe/MeOH solution (12.7 mL, 6.33 mmol) was refluxed overnight. Then the mixture was concentrated in vacuo and the residue was dissolved in water. The solution was acidified with 2 M HCl to pH=3~4. The resulting precipitate was collected by filtration, washed with water, and freeze-dried to give the title compound as a powder (209 mg); ESI MS (m/z): 422 (M+H)$^+$.

Example 32

{[7-(Benzo[1,3]dioxol-5-yloxy)-1-cyano-4-hydroxy-isoquinoline-3-carbonyl]-amino}-acetic acid a) 4-(Benzo[1,3]dioxol-5-yloxy)-phthalonitrile

Prepared in analogy to example 31a from benzo[1,3]dioxol-5-ol. $^1$H NMR (200 MHz, CDCl$_3$): δ (ppm)=7.8-6.5 (m, 8H).

b) 4-(Benzo[1,3]dioxol-5-yloxy)-phthalic acid

Prepared in analogy to example 31b from 4-(benzo[1,3]dioxol-5-yloxy)-phthalonitrile. $^1$H NMR (200 MHz, DMSO-d6): δ (ppm)=7.95 (d, 1H, 8.7 Hz), 7.3-6.5 (m, 7 Hz).

c) [5-(Benzo[1,3]dioxol-5-yloxy)-1,3-dioxo-1,3-dihydro-isoindol-2-yl]-acetic acid ethyl ester Prepared in analogy to example 31c from 4-(benzo[1,3]dioxol-5-yloxy)-phthalic acid. $^1$H NMR (200 MHz, CDCl$_3$): δ (ppm)=7.78 (d, 1H, J=7.4 Hz), 7.29-7.21 (m, 2H), 6.81 (d, 1H, J=6.4 Hz), 6.60-6.52 (m, 2H), 4.39 (s, 2H), 4.21 (q, 2H, J=6.8 Hz), 1.28 (t, 3H, J=6.8 Hz).

d) 7-(Benzo[1,3]dioxol-5-yloxy)-4-hydroxy-1-oxo-1,2-dihydro-isoquinoline-3-carboxylic acid butyl ester and 6-(Benzo[1,3]dioxol-5-yloxy)-4-hydroxy-1-oxo-1,2-dihydro-isoquinoline-3-carboxylic acid butyl ester Prepared in analogy to example 31e from [5-(benzo[1,3]dioxol-5-yloxy)-1,3-dioxo-1,3-dihydro-isoindol-2-yl]-acetic acid ethyl ester. 7-(benzo[1,3]dioxol-5-yloxy)-4-hydroxy-1-oxo-1,2-dihydro-isoquinoline-3-carboxylic acid butyl ester: $^1$H NMR (200 MHz, CDCl$_3$): δ (ppm)=10.56 (br, s, 1H), 8.30 (br, s, 1H), 8.2-6.5 (m, 6H), 6.01 (s, 2H), 4.39 (t, 2H), 1.78 (m, 2H), 1.50 (m, 2H), 0.99 (t, 3H, J=7.3 Hz); 6-(benzo[1,3]dioxol-5-yloxy)-4-hydroxy-1-oxo-1,2-dihydro-isoquinoline-3-carboxylic acid butyl ester: $^1$H NMR (200 MHz, CDCl$_3$): δ (ppm)=10.4 (br, s, 1H), 8.4-6.5 (m, 7H), 6.02 (s, 2H), 4.40 (t, 2H, J=6.6 Hz), 1.85-1.40 (m, 4H), 0.99 (t, 3H, J=7.3 Hz).

e) 7-(Benzo[1,3]dioxol-5-yloxy)-1-chloro-4-hydroxy-isoquinoline-3-carboxylic acid butyl ester Prepared in analogy to example 31f from 7-(benzo[1,3]dioxol-5-yloxy)-4-hydroxy-1-oxo-1,2-dihydro-isoquinoline-3-carboxylic acid butyl ester and POCl$_3$. $^1$H NMR (200 MHz, CDCl$_3$): δ (ppm)=11.89 (s, 1H), 8.35 (d, 1H, J=9.2 Hz), 7.57 (d, 1H, J=1.9 Hz), 7.50 (m, 1 H), 6.83 (d, 1H, J=7.8 Hz), 6.65-6.56 (m, 2H), 6.03 (s, 2H), 4.47 (t, 2H, J=7.1 Hz), 1.9-1.4 (m, 4H), 0.99 (t, 3H, J=7.3 Hz).

f) 7-(Benzo[1,3]dioxol-5-yloxy)-1-cyano-4-hydroxy-isoquinoline-3-carboxylic acid butyl ester A mixture of 7-(benzo[1,3]dioxol-5-yloxy)-1-chloro-4-hydroxy-isoquinoline-3-carboxylic acid butyl ester (118 mg, 0.284 mmol), zinc cyanide (20 mg, 0.17 mmol), zinc (2.2 mg), Pd$_2$(dba)$_3$ (13 mg, 0.0142 mmol), dppf (15.7 mg, 0.0284 mmol), and dimethylacetamide (1 mL) was stirred at 120° C. for 90 min. After cooling to ambient temperature the reaction mixture was diluted with EtOAc, washed with water, and saturated NaCl solution before it was dried over anhydrous sodium sulfate and concentrated in vacuo. The residue was purified by column chromatography to give the title compound (50 mg). ESI MS (m/z): 407 (M+H)$^+$.

g) {[7-(Benzo[1,3]dioxol-5-yloxy)-1-cyano-4-hydroxy-isoquinoline-3-carbonyl]-amino}-acetic acid Prepared in analogy to example 31h from 7-(benzo[1,3]dioxol-5-yloxy)-1-cyano-4-hydroxy-isoquinoline-3-carboxylic acid butyl ester and glycine. ESI MS (m/z): 406 (M−H)$^−$.

Example 33

{[6-(Benzo[1,3]dioxol-5-yloxy)-1-cyano-4-hydroxy-isoquinoline-3-carbonyl]-amino}-acetic acid a) 6-(Benzo[1,3]dioxol-5-yloxy)-1-bromo-4-hydroxy-isoquinoline-3-carboxylic acid butyl ester Prepared in analogy to example 31f from 6-(benzo[1,3]dioxol-5-yloxy)-4-hydroxy-1-oxo-1,2-dihydro-isoquinoline-3-carboxylic acid butyl ester and $POBr_3$. ESI MS (m/z): 460 (M+H)$^+$.

b) 6-(Benzo[1,3]dioxol-5-yloxy)-1-cyano-4-hydroxy-isoquinoline-3-carboxylic acid butyl ester Prepared in analogy to example 31g from 6-(benzo[1,3]dioxol-5-yloxy)-1-bromo-4-hydroxy-isoquinoline-3-carboxylic acid butyl ester and CuCN. ESI MS (m/z): 407 (M+H)$^+$.

c) {[6-(Benzo[1,3]dioxol-5-yloxy)-1-cyano-4-hydroxy-isoquinoline-3-carbonyl]-amino}-acetic acid Prepared in analogy to example 31h from 6-(benzo[1,3]dioxol-5-yloxy)-1-cyano-4-hydroxy-isoquinoline-3-carboxylic acid butyl ester and glycine. ESI MS (m/z): 408 (M+H)$^+$.

Example 34

{[1-Cyano-6-(2,3-dihydro-benzofuran-5-yloxy)-4-hydroxy-isoquinoline-3-carbonyl]-amino}-acetic acid a) 4-(2,3-Dihydro-benzofuran-5-yloxy)-phthalonitrile Prepared in analogy to example 31a from 2,3-dihydro-benzofuran-5-ol. $^1$H NMR (200 MHz, CDCl$_3$): δ (ppm)=7.7-6.7 (m, 6H), 4.65 (t, 2H, J=7.8 Hz), 3.25 (t, 2H, J=7.8 Hz).

b) 4-(2,3-Dihydro-benzofuran-5-yloxy)-phthalic acid

Prepared in analogy to example 31b from 4-(2,3-dihydro-benzofuran-5-yloxy)-phthalonitrile. $^1$H NMR (200 MHz, DMSO-d6): δ (ppm)=14-13 (br, 2H), 7.78-6.77 (m, 6H), 4.55 (m, 2H), 3.19 (m, 2H).

c) [5-(2,3-Dihydro-benzofuran-5-yloxy)-1,3-dioxo-1,3-dihydro-isoindol-2-yl]-acetic acid ethyl ester Prepared in analogy to example 31c from 4-(2,3-dihydro-benzofuran-5-yloxy)-phthalic acid. $^1$H NMR (200 MHz, CDCl$_3$): δ (ppm)=7.8-6.8 (m, 6H), 4.63 (m, 2H), 4.38 (s, 2H), 4.20 (m, 2H), 3.24 (t, 2H, J=4.4 Hz), 1.28 (t, 3H, J=7.1 Hz).

d) 7-(2,3-Dihydro-benzofuran-5-yloxy)-4-hydroxy-1-oxo-1,2-dihydro-isoquinoline-3-carboxylic acid butyl ester and 6-(2,3-Dihydro-benzofuran-5-yloxy)-4-hydroxy-1-oxo-1,2-dihydro-isoquinoline-3-carboxylic acid butyl ester Prepared in analogy to example 31e from [5-(2,3-Dihydro-benzofuran-5-yloxy)-1,3-dioxo-1,3-dihydro-isoindol-2-yl]-acetic acid ethyl ester. 7-(2,3-Dihydro-benzofuran-5-yloxy)-4-hydroxy-1-oxo-1,2-dihydro-isoquinoline-3-carboxylic acid butyl ester: ESI MS (m/z) 396 (M+H)$^+$; 6-(2,3-dihydro-benzofuran-5-yloxy)-4-hydroxy-1-oxo-1,2-dihydro-isoquinoline-3-carboxylic acid butyl ester: ESI MS (m/z): 396 (M+H)$^+$.

e) 1-Bromo-6-(2,3-dihydro-benzofuran-5-yloxy)-4-hydroxy-isoquinoline-3-carboxylic acid butyl ester Prepared in analogy to example 31f from 6-(2,3-dihydro-benzofuran-5-yloxy)-4-hydroxy-1-oxo-1,2-dihydro-isoquinoline-3-carboxylic acid butyl ester and POBr$_3$. ESI MS (m/z): 458 (M+H)$^+$.

f) 1-Cyano-6-(2,3-dihydro-benzofuran-5-yloxy)-4-hydroxy-isoquinoline-3-carboxylic acid butyl ester Prepared in analogy to example 31g from 1-bromo-6-(2,3-dihydro-benzofuran-5-yloxy)-4-hydroxy-isoquinoline-3-carboxylic acid butyl ester and CuCN. ESI MS (m/z): 405 (M+H)$^+$.

g) {[1-Cyano-6-(2,3-dihydro-benzofuran-5-yloxy)-4-hydroxy-isoquinoline-3-carbonyl]-amino}-acetic acid Prepared in analogy to example 31h from 1-cyano-6-(2,3-dihydro-benzofuran-5-yloxy)-4-hydroxy-isoquinoline-3-carboxylic acid butyl ester and glycine. ESI MS (m/z): 404 (M−H)$^−$.

Example 35

[(1-Cyano-4-methoxy-8-phenoxy-isoquinoline-3-carbonyl)-amino]-acetic acid methyl ester a) 1-Bromo-4-methoxy-8-phenoxy-isoquinoline-3-carboxylic acid methyl ester A mixture of 1-bromo-4-hydroxy-8-phenoxy-isoquinoline-3-carboxylic acid methyl ester (1.89 g, 5.07 mmol), iodomethane (632 μL, 10.13 mmol), cesium carbonate (3.3 g, 10.13 mmol) and dimethylformamide (15 mL) was stirred at 45° C. for sixteen hours before it was quenched with water, extracted with ethyl acetate. The organic layer was washed with water, brine, dried over sodium sulfate, concentrated in vacuo and the residue was purified by flash column chromatography on silica gel with a gradient of ethyl acetate and hexanes to give the title compound as a yellow solid (1.03 g): MS: (+) m/z 387.64, 389.75 (M+1, $^{79}$Br/$^{81}$Br).

b) 1-Cyano-4-methoxy-8-phenoxy-isoquinoline-3-carboxylic acid methyl ester

A mixture of 1-bromo-4-methoxy-8-phenoxy-isoquinoline-3-carboxylic acid methyl ester (1.02 g, 2.63 mmol), copper (I) cyanide (470 mg, 5.25 mmol) and anhydrous dimethylformamide (8.8 mL) was refluxed for ten minutes before it was cooled to room temperature quenched with water and ethyl acetate. The slurry was filtered. The organic layer was washed with water, brine, dried over anhydrous sodium sulfate, concentrated in vacuo and the residue was purified by flash column chromatography on silica gel with a gradient of ethyl acetate and hexanes to give the title compound as a yellow solid (727 mg): MS: (+) m/z 334.83 (M+1).

c) 1-Cyano-4-methoxy-8-phenoxy-isoquinoline-3-carboxylic acid

To a mixture of 1-cyano-4-methoxy-8-phenoxy-isoquinoline-3-carboxylic acid methyl ester (727 mg, 2.18 mmol) and methanol/tetrahydrofuran (12.5 mL, 1:1.5) was added 2N sodium hydroxide (5.4 mL, 10.89 mmol) at room temperature. The yellow solution was stirred at that temperature for seventy minutes before it was concentrated. Water (20 mL) was added and the mixture was adjusted to pH=2 with 1N HCl (13 mL). The mixture was then extracted with dichloromethane and ethyl acetate. The combined organic layers were washed with brine, dried over anhydrous sodium sulfate, concentrated in vacuo to give the title compound as a yellow solid (647 mg): MS: (+) m/z 320.80 (M+1).

d) [(1-Cyano-4-methoxy-8-phenoxy-isoquinoline-3-carbonyl)-amino]-acetic acid methyl ester To a mixture of 1-cyano-4-methoxy-8-phenoxy-isoquinoline-3-carboxylic acid (483 mg, 1.51 mmol), triethylamine (466 µL, 3.32 mmol), and dichloromethane (12 mL) was added isobutylchloroformate (211 µL, 1.62 mmol) at 0° C. The mixture was stirred at 0° C. for twenty-five minutes before glycine methyl ester hydrochloride (208 mg, 1.66 mmol) was added. The mixture was stirred at 0° C. for twenty-five minutes and at room temperature for 5.5 hours before it was concentrated. The residue was partitioned between ethyl acetate and 1N HCl. The organic layer was washed with saturated sodium bicarbonate, brine, dried over anhydrous sodium sulfate, concentrated in vacuo and the residue was purified by flash column chromatography on silica gel with a gradient of ethyl acetate and hexanes to give the title compound as a yellow solid (343 mg): MS: (+) m/z 391.95 (M+1).

Example 36

[(1-Cyano-4-methoxy-8-phenoxy-isoquinoline-3-carbonyl)-amino]-acetic acid

To a mixture of [(1-cyano-4-methoxy-8-phenoxy-isoquinoline-3-carbonyl)-amino]-acetic acid methyl ester (21 mg, 0.05 mmol), and methanol/tetrahydrofuran (0.9 mL, 1:3.5) was added 2N sodium hydroxide (29.2 µL, 0.06 mmol) at room temperature. The yellow solution was stirred at that temperature for fifty-five minutes before it was acidified with 1N HCl (69.1 µL) to pH=3 and concentrated in vacuo. The residue was partitioned between ethyl acetate and water. The organic layer was dried over anhydrous sodium sulfate, concentrated in vacuo and the residue was purified by flash column chromatography on silica gel with a gradient of methanol, dichloromethane and acetic acid (0.1%) to give the title compound as a pale brown solid (15 mg): MS: (+) m/z 378.00 (M+1).

Example 37

(S)-2-[(1-Cyano-4-hydroxy-8-phenoxy-isoquinoline-3-carbonyl)-amino]-propionic acid A mixture of 1-cyano-4-methoxy-8-phenoxy-isoquinoline-3-carboxylic acid methyl ester (101 mg, 0.31 mmol) and L-Alanine (561 mg, 6.29 mmol) in 0.5 M sodium methoxide/methanol (12 mL) was refluxed for four days before it was cooled to room temperature and concentrated in vacuo. The residue was dissolved in water (20 mL) and extracted with methyl t-butyl ether (2×30 mL). The remaining aqueous layer was acidified to pH=3 with 1N HCl (8 mL). The resulting white suspension was extracted with ethyl acetate (30 mL), dried and concentrated in vacuo to give the title compound as a white solid (117 mg): $^1$H NMR (DMSO-$d_6$, 200 MHz): δ=13.52 (bs, 1H), 10.11 (br s, 1H), 8.30 (d, 1H), 8.07 (m, 1H), 7.67 (t, J=8 Hz, 1H), 7.42 (m, 2H), 7.17 (m, 3H), 4.83 (q, 1H), 1.68 (d, J=7.4 Hz); MS: (+) m/z 378.29 (M+1).

Example 38

(R)-2-[(1-Cyano-4-hydroxy-8-phenoxy-isoquinoline-3-carbonyl)-amino]-propionic acid A mixture of 1-cyano-4-hydroxy-8-phenoxy-isoquinoline-3-carboxylic acid methyl ester (95 mg, 0.30 mmole), D-Alanine (529 mg, 5.94 mmole) and 0.5 M sodium methoxide/methanol (11.3 mL) was refluxed for three days before it was cooled to room temperature and concentrated in vacuo. The residue was dissolved in water (25 mL) and extracted with dichloromethane (3×30 mL). The remaining aqueous layer was acidified to pH=3 with 1N HCl (8 mL). The white suspension was extracted with ethyl acetate (30 mL) and dichloromethane (30 mL). The combined organic layers were washed with brine, dried over MgSO$_4$ and concentrated in vacuo to give the title compound as a white solid (90 mg): $^1$H NMR (DMSO-$d_6$, 200 MHz): δ=13.52 (bs, 1H), 9.15 (br s, 1H), 8.30 (d, 1H), 8.10 (m, 1H), 7.67 (t, J=8 Hz, 1H), 7.42 (m, 2H), 7.17 (m, 3H), 4.83 (q, 1H), 1.68 (d, J=7.0 Hz, 3H)); MS: (+) m/z 378.29 (M+1).

Example 39

{[1-Cyano-4-hydroxy-6-(2-methyl-benzothiazol-6-yloxy)-isoquinoline-3-carbonyl]-amino}-acetic acid a) 2-Methyl-benzothiazol-6-ol A mixture of 6-methoxy-2-methyl-benzothiazole (19.71 g, 0.11 mol), tetrabutylphosphonium bromide (3.73 g, 0.01 mol), and 48% HBr (120 mL) was stirred at 105° C. for twenty-eight hours before it was cooled to room temperature, neutralized with 10N NaOH (90 mL) and 1N NaOH (45 mL) to pH=4. The resulting precipitate was filtered, washed with water (3×100 mL), dried in vacuo to give the title compound as a pale brown solid (14.81 g): $^1$H NMR (CDCl$_3$, 200 MHz): δ=7.77 (m, 1H), 7.24 (m, 1H), 6.94 (m, 1H), 5.28 (s, 1H), 2.79 (s, 3H).

b) 5-Nitro-(1,3-dioxo-1,3-dihydro-isoindol-2-yl)-acetic acid ethyl ester

A mixture of 4-nitrophthalimide (82.54 g, 0.43 mol), ethyl bromoacetate (78.92 g, 0.47 mol) and potassium carbonate (130.6 g, 0.94 mol), and acetone (1.5l) was refluxed for eighteen hours before it was cooled to room temperature, filtered and concentrated in vacuo. The residue was partitioned between dichloromethane and water. The organic layer was dried over anhydrous sodium sulfate and concentrated in vacuo to give the title compound as a yellow solid (107.39 g): MS: (+) m/z 279.25 (M+1).

c) [5-(2-Methyl-benzothiazol-6-yloxy)-1,3-dioxo-1,3-dihydro-isoindol-2-yl]-acetic acid ethyl ester A mixture of 2-methyl-benzothiazol-6-ol (2.30 g, 13.92 mmol), 5-nitro-(1,3-dioxo-1,3-dihydro-isoindol-2-yl)-acetic acid ethyl ester (4.26 g, 15.31 mmol), potassium carbonate (2.3 g, 16.64 mmol) and dimethylacetamide (30 mL) was stirred at 105° C. for twenty hours before it was cooled to room temperature and partitioned between ethyl acetate and water. The organic layer was dried over anhydrous sodium sulfate, concentrated in vacuo and the residue was purified by flash column chromatography on silica gel with a gradient of ethyl acetate and dichloromethane to give the title compound as a yellow solid (2.35 g): MS: (+) m/z 397.19 (M+1).

d) 1,4-Dihydroxy-6-(2-methyl-benzothiazol-6-yloxy)-isoquinoline-3-carboxylic acid butyl ester and 1,4-Dihydroxy-7-(2-methyl-benzothiazol-6-yloxy)-isoquinoline-3-carboxylic acid butyl ester Sodium (1.56 g, 0.07 mol) was dissolved in anhydrous 1-butanol (70 mL) and stirred at 80° C. for one hour. The resulting solution was added to a solution of [5-(2-methyl-benzothiazol-6-yloxy)-1,3-dioxo-1,3-dihydro-isoindol-2-yl]-acetic acid ethyl ester (12.79 g, 0.03 mol) in anhydrous 1-butanol (90 mL). The mixture was stirred at 105° C. for two hours before it was cooled to room temperature, acidified with 5N HCl (13.5 mL) to pH=5. The precipitate was filtered, washed with water, dried in vacuo to give the 6,7-isomeric mixture of title compound as a yellow solid (9.9 g): MS: (+) m/z 425.33 (M+1).

e) 1-Chloro-4-hydroxy-6-(2-methyl-benzothiazol-6-yloxy)-isoquinoline-3-carboxylic acid butyl ester A solution of the regioisomeric mixture of 1,4-dihydroxy-6-(2-methyl-benzothiazol-6-yloxy)-isoquinoline-3-carboxylic acid butyl ester/1,4-dihydroxy-7-(2-methyl-benzothiazol-6-yloxy)-isoquinoline-3-carboxylic acid butyl ester obtained above (3 g, 7.08 mmol), and phosphorus oxychloride (791 µL, 8.49 mmol) in dichloroethane (35 mL) was stirred at 120° C. in a CEM microwave apparatus for thirty minutes. The procedure was repeated three times. The combined reaction mixtures were filtered, saturated sodium bicarbonate solution was added and the mixture was stirred for one hour. The organic layer was washed with brine, dried over anhydrous sodium sulfate, concentrated in vacuo and the residue was purified by flash column chromatography on silica gel with a gradient of ethyl acetate and dichloromethane to give a yellow solid (7.05 g). It was recrystallized from ethyl acetate (230 mL) to give the title compound as a yellow solid (3.42 g): MS: (+) m/z 443.24 (M+1).

f) 1-Cyano-4-hydroxy-6-(2-methyl-benzothiazol-6-yloxy)-isoquinoline-3-carboxylic acid butyl ester A mixture of 1-chloro-4-hydroxy-6-(2-methyl-benzothiazol-6-yloxy)-isoquinoline-3-carboxylic acid butyl ester (369 mg, 0.84 mmol), tris(dibenzylideneacetone)dipalladium(0) (38 mg, 0.04 mmol), 1,1'-bis(diphenylphosphino)ferrocene (46 mg, 0.08 mmol), zinc cyanide (59 mg, 0.50 mmol), zinc (6 mg, 0.10 mmol) and dimethylacetamide (2 mL) was stirred at 120° C. for two hours and twenty minutes before it was cooled to room temperature, partitioned between ethyl acetate and water, and filtered. The filtrate was washed with water and brine, dried over anhydrous sodium sulfate and concentrated in vacuo. The residue was purified by flash column chromatography on silica gel with a gradient of ethyl acetate and dichloromethane to give the title compound as a white solid (245 mg): MS: (+) m/z 434.30 (M+1).

g) {[1-Cyano-4-hydroxy-6-(2-methyl-benzothiazol-6-yloxy)-isoquinoline-3-carbonyl]-amino}-acetic acid A mixture of 1-cyano-4-hydroxy-6-(2-methyl-benzothiazol-6-yloxy)-isoquinoline-3-carboxylic acid butyl ester (113 mg, 0.26 mmol) and glycine (390 mg, 5.20 mmol) in 0.5 M sodium methoxide/methanol (9.9 mL) was refluxed for forty-five hours before it was cooled to room temperature and concentrated in vacuo. The residue was dissolved in water (35 mL) and extracted with methyl tert-butyl ether (2×25 mL). The remaining aqueous layer was acidified to pH=3 with 1N HCl (7.4 mL). The white precipitate was filtered, washed with water and dried in vacuo to give the title compound as a white solid (92 mg): MS: (+) m/z 434.93 (M+1), (−) m/z 432.87 (M−1).

Example 40

{[1-Cyano-6-(2-dimethylamino-benzooxazol-5-yloxy)-4-hydroxy-isoquinoline-3-carbonyl]-amino}-acetic acid a) 2-Amino-4-methoxy-phenol A mixture of 4-methoxy-2-nitrophenol (30.2 g, 0.18 mol), 10% Pd/C, ethanol (200 mL), and ethyl acetate (200 mL) was hydrogenated at ambient pressure and temperature for three days before it was filtered and concentrated in vacuo to give the title compound as a dark brown solid (20.78 g): $^1$H NMR (CDCl$_3$, 200 MHz): δ=6.64 (m, 1H), 6.32 (m, 1H), 6.21 (m, 1H), 3.71 (s, 3H).

b) 5-Methoxy-benzooxazole-2-thiol

A mixture of 2-amino-4-methoxy-phenol (20.7 g, 0.15 mol), potassium O-ethylxanthate (26.2 g, 0.16 mol) and anhydrous pyridine was refluxed for two hours before it was cooled to room temperature and ice-cold 1N HCl (600 mL) was added. The precipitate was filtered, washed with water and dried in vacuo to give the title compound as a pale red solid (22.36 g): $^1$H NMR (CDCl$_3$, 200 MHz): δ=7.20 (m, 1H), 6.78 (m, 2H), 3.82 (s, 3H).

c) 2-Chloro-5-methoxy-benzooxazole

To a mixture of 5-methoxy-benzooxazole-2-thiol (12.14 g, 0.07 mol) and thionyl chloride were added two drops of DMF. The mixture was stirred at 68° C. for forty minutes and the formation of gas had stopped. The mixture was diluted with dichloromethane, concentrated, and dried in vacuo to give the title compound as a green solid (14.31 g): $^1$H NMR (CDCl$_3$, 200 MHz): δ=7.36 (m, 1H), 7.13 (m, 1H), 6.92 (m, 1H), 3.84 (s, 3H).

d) (5-Methoxy-benzooxazol-2-yl)-dimethyl-amine

A mixture of 2-chloro-5-methoxy-benzooxazole (1.52 g, 8.31 mmol) and a 40% solution of dimethylamine in water (15 mL) was refluxed for two hours before it was cooled to room temperature and partitioned between ethyl acetate and water. The organic layer was dried over anhydrous sodium sulfate and concentrated in vacuo to give the title compound as a black oil (1.14 g): MS: (+) m/z 397.19 (M+1)

e) 2-Dimethylamino-benzooxazol-5-ol

A mixture of (5-methoxy-benzooxazol-2-yl)-dimethyl-amine (6.41 g, 0.03 mol), tetrabutylphosphonium bromide (1.13 g, 3.34 mmol), and 48% HBr (40 mL) was stirred at 105° C. for twenty-five hours before it was cooled to room temperature, neutralized with 10N NaOH (30 mL) to pH=8. The resulting precipitate was filtered, washed with water, and dried in vacuo to give the title compound as a pale brown solid (4.94 g): $^1$H NMR (CDCl$_3$, 200 MHz): δ=7.05 (m, 1H), 6.86 (m, 1H), 6.48 (m, 1H), 3.19 (s, 6H).

f) [5-(2-Dimethylamino-benzooxazol-5-yloxy)-1,3-dioxo-1,3-dihydro-isoindol-2-yl]-acetic acid ethyl ester A mixture of 2-dimethylamino-benzooxazol-5-ol (4.82 g, 0.03 mmol), 5-nitro-1,3-dioxo-1,3-dihydro-isoindol-2-yl)-acetic acid ethyl ester (8.66 g, 0.03 mmol), potassium carbonate (4.49 g, 0.03 mmol) and dimethylacetamide (30 mL) was stirred at 105° C. for twenty-two hours before it was cooled to room temperature and partitioned between chloroform and water. The organic layer was dried over anhydrous sodium sulfate, concentrated in vacuo and purified by flash column chromatography on silica gel with a gradient of ethyl acetate and dichloromethane to give the title compound as a orange solid (4.24 g): MS: (+) m/z 410.2 (M+1).

g) 6-(2-Dimethylamino-benzooxazol-5-yloxy)-1,4-dihydroxy-isoquinoline-3-carboxylic acid butyl ester and 7-(2-Dimethylamino-benzooxazol-5-yloxy)-1,4-dihydroxy-isoquinoline-3-carboxylic acid butyl ester Sodium (475 mg, 20.65 mmol) was dissolved in anhydrous 1-butanol (24 mL) at 85° C. The resulting freshly prepared solution was added to a solution of [5-(2-dimethylamino-benzooxazol-5-yloxy)-1,3-dioxo-1,3-dihydro-isoindol-2-yl]-acetic acid ethyl ester (4.23 g, 0.01 mol) in anhydrous 1-butanol (30 mL). The mixture was stirred at 105° C. for one hour and forty-five minutes before it was cooled to room temperature, acidified with 2N HCl (10 mL) to pH=5. The precipitate was filtered, washed with water, dried in vacuo to give a regioisomeric mixture of title compounds as a yellow solid (1.2 g): MS: (+) m/z 438.2 (M+1). The filtrate was extracted with ethyl acetate. The organic layer was dried over anhydrous sodium sulfate, concentrated in vacuo and the residue was purified by flash column chromatography on silica gel with a gradient of ethyl acetate and dichloromethane. Fractions corresponding to pure 7-regioisomer were collected and concentrated to give a yellow solid (452 mg): MS: (+) m/z 438.2 (M+1).

h) 1-Chloro-6-(2-dimethylamino-benzooxazol-5-yloxy)-4-hydroxy-isoquinoline-3-carboxylic acid butyl ester A solution of the regioisomeric mixture of 6-(2-dimethylamino-benzooxazol-5-yloxy)-1,4-dihydroxy-isoquinoline-3-carboxylic acid butyl ester and 7-(2-dimethylamino-benzooxazol-5-yloxy)-1,4-dihydroxy-isoquinoline-3-carboxylic acid butyl ester obtained as described above (1.05 g, 2.41 mmol), and phosphorus oxychloride (286 μL, 3.13 mmol) in dichloroethane (18 mL) was stirred at 120° C. in a CEM microwave apparatus for thirty minutes. The mixture was stirred with saturated sodium bicarbonate solution for twenty minutes. The organic layer was washed with brine, dried over anhydrous sodium sulfate, concentrated in vacuo. Purification by flash column chromatography on silica gel with a gradient of ethyl acetate and dichloromethane gave a solid (463 mg). Recrystallization from ethyl acetate (190 mL) furnished the title compound as a yellow solid (219 mg): MS: (+) m/z 456.31 (M+1).

i) 1-Cyano-6-(2-dimethylamino-benzooxazol-5-yloxy)-4-hydroxy-isoquinoline-3-carboxylic acid butyl ester A mixture of 1-chloro-6-(2-dimethylamino-benzooxazol-5-yloxy)-4-hydroxy-isoquinoline-3-carboxylic acid butyl ester (115 mg, 0.25 mmol), tris(dibenzylideneacetone)dipalladium(0) (12 mg, 0.01 mmol), 1,1'-bis(diphenylphosphino)ferrocene (14 mg, 0.02 mmol), zinc cyanide (18 mg, 0.15 mmol), zinc (2 mg, 0.03 mmol) and dimethylacetamide (0.6 mL) was stirred at 120° C. for two hours before it was cooled to room temperature, partitioned between ethyl acetate and water, filtered. The filtrate was washed with water and brine, dried over anhydrous sodium sulfate and concentrated in vacuo. The residue was purified by flash column chromatography on silica gel with a gradient of ethyl acetate and dichloromethane to give the title compound as a white solid (53 mg): MS: (+) m/z 447.00 (M+1); (−) m/z 445.20 (M−1).

j) {[1-Cyano-6-(2-dimethylamino-benzooxazol-5-yloxy)-4-hydroxy-isoquinoline-3-carbonyl]-amino}-acetic acid A mixture of 1-cyano-6-(2-dimethylamino-benzooxazol-5-yloxy)-4-hydroxy-isoquinoline-3-carboxylic acid butyl ester (55 mg, 0.12 mmol), glycine (186 mg, 2.47 mmol) and 0.5 M sodium methoxide/methanol (4.7 mL) was refluxed for twenty-five hours before it was cooled to room temperature and concentrated in vacuo. The residue was dissolved in water (35 mL) and washed with dichloromethane (2×25 mL). The remaining aqueous layer was acidified to pH=3 with 1N HCl (3.5 mL). The white precipitate was filtered, washed with water and dried in vacuo to give the title compound as a white solid (44 mg): MS: (+) m/z 448.27 (M+1).

Example 41

{[1-Cyano-7-(2-dimethylamino-benzooxazol-5-yloxy)-4-hydroxy-isoquinoline-3-carbonyl]-amino}-acetic acid a) 1-Chloro-7-(2-dimethylamino-benzooxazol-5-yloxy)-4-hydroxy-isoquinoline-3-carboxylic acid butyl ester A mixture of 7-(2-dimethylamino-benzooxazol-5-yloxy)-1,4-dihydroxy-isoquinoline-3-carboxylic acid butyl ester (364 mg, 0.83 mmol), phosphorus oxychloride (92 μL, 1.00 mmol) and dichloroethane (4.5 mL) was stirred at 120° C. in a CEM microwave apparatus for thirty minutes. The mixture was then stirred with saturated sodium bicarbonate for fifteen minutes at ambient temperature. The organic layer was washed with brine, dried over anhydrous sodium sulfate, concentrated in vacuo and the residue was purified by flash column chromatography on silica gel with a gradient of ethyl acetate and dichloromethane to give the title compound as a white solid (220 mg): MS: (+) m/z 456.32 (M+1).

b) 1-Cyano-7-(2-dimethylamino-benzooxazol-5-yloxy)-4-hydroxy-isoquinoline-3-carboxylic acid butyl ester A mixture of 1-chloro-7-(2-dimethylamino-benzooxazol-5-yloxy)-4-hydroxy-isoquinoline-3-carboxylic acid butyl ester (92 mg, 0.20 mmol), tris(dibenzylideneacetone)dipalladium(0) (9 mg, 0.01 mmol), 1,1'-bis(diphenylphosphino)ferrocene (11 mg, 0.02 mmol), zinc cyanide (14 mg, 0.12 mmol), zinc (2 mg, 0.02 mmol) and dimethylacetamide (0.5 mL) was stirred at 120° C. for two hours before it was cooled to room temperature, partitioned between ethyl acetate and water, and filtered. The filtrate was washed with water and brine, dried over anhydrous sodium sulfate and concentrated in vacuo. The residue was purified by flash column chromatography on silica gel with a gradient of ethyl acetate and dichloromethane to give the title compound as a white solid (32 mg): MS: (+) m/z 447.00 (M+1); (−) m/z 445.20 (M−1).

c) {[1-Cyano-7-(2-dimethylamino-benzooxazol-5-yloxy)-4-hydroxy-isoquinoline-3-carbonyl]-amino}-acetic acid A mixture of 1-cyano-7-(2-dimethylamino-benzooxazol-5-yloxy)-4-hydroxy-isoquinoline-3-carboxylic acid butyl ester (37 mg, 0.08 mmol), glycine (126 mg, 1.68 mmol) and 0.5 M sodium methoxide/methanol (3.2 mL) was refluxed for twenty-five hours before it was cooled to room temperature and concentrated in vacuo. The residue was dissolved in water (20 mL) and extracted with dichloromethane (2×25 mL). The remaining aqueous layer was acidified to pH=3 with 1N HCl (2.4 mL). The white precipitate was filtered, washed with water and dried in vacuo to give the title compound as a white solid (24 mg): MS: (+) m/z 448.27 (M+1).

Example 42

{[1-Cyano-4-hydroxy-6-(2-morpholin-4-yl-benzothiazol-6-yloxy)-isoquinoline-3-carbonyl]-amino}-acetic acid a) 2-Chloro-6-methoxy-benzothiazole

To a mixture of isoamyl nitrite (17.55 g, 0.15 mol), copper (II) chloride (16.1 g, 0.12 mol) and anhydrous acetonitrile (400 mL) was added 2-amino-6-methoxybenzothiazole (18 g, 0.10 mol) over a period of forty minutes at room temperature. The mixture was stirred at 65° C. for three hours, quenched with 4N HCl (400 mL) and extracted with diethyl ether (2×300 mL). The organic layer was dried over anhydrous sodium sulfate, concentrated in vacuo and the residue was purified by flash column chromatography on silica gel with a gradient of ethyl acetate and hexanes to give the title compound as a yellow solid (9.97 g): $^1$H NMR (CDCl$_3$, 200 MHz): δ=7.80 (m, 1H), 7.19 (m, 1H), 7.06 (m, 1H), 3.86 (s, 3H).

b) 6-Methoxy-2-morpholin-4-yl-benzothiazole

A mixture of 2-chloro-6-methoxy-benzothiazole (9.96 g, 0.05 mol), morpholine (10.86 mL, 0.12 mol) and triethylamine (13.9 mL, 0.10 mol) in ethanol (75 mL) was refluxed for twenty-one hours before it was cooled to room temperature and concentrated in vacuo. The residue was partitioned between dichloromethane and water. The organic layer was dried over anhydrous sodium sulfate and concentrated in vacuo to give the title compound as a light yellow solid (12.23 g): MS: (+) m/z 251 (M+1)

c) 2-Morpholin-4-yl-benzothiazol-6-ol

A mixture of 6-methoxy-2-morpholin-4-yl-benzothiazole (12.20 g, 48.7 mmol), tetrabutylphosphonium bromide (1.65 g, 4.87 mmol) and 48% HBr (80 mL) was stirred at 100° C. for twenty hours before it was cooled to room temperature, neutralized with 10N NaOH (60 mL) to pH=5-6. The mixture was extracted with dichloromethane. The organic layer was dried over anhydrous sodium sulfate, concentrated in vacuo to give the title compound as a white solid (10.69 g): $^1$H NMR (CDCl$_3$, 200 MHz): δ=7.28 (m, 1H), 7.15 (m, 1H), 6.75 (m, 1H), 3.70 (m, 4H), 3.43 (m, 4H).

d) [5-(2-Morpholin-4-yl-benzothiazol-6-yloxy)-1,3-dioxo-1,3-dihydro-isoindol-2-yl]-acetic acid ethyl ester A mixture of 2-morpholin-4-yl-benzothiazol-6-ol (238 mg, 1.01 mmol), 5-nitro-1,3-dioxo-1,3-dihydro-isoindol-2-yl)-acetic acid ethyl ester (294 mg, 1.06 mmol), potassium carbonate (167 mg, 1.21 mmol) and dimethylacetamide (6 mL) was stirred at 105° C. for twenty-two hours before it was cooled to room temperature and partitioned between chloroform and water. The organic layer was dried over anhydrous sodium sulfate, concentrated in vacuo and the residue was purified by flash column chromatography on silica gel with a gradient of ethyl acetate and dichloromethane to give the title compound as a yellow solid (259 mg): MS: (+) m/z 468.21 (M+1).

e) 1,4-Dihydroxy-6-(2-morpholin-4-yl-benzothiazol-6-yloxy)-isoquinoline-3-carboxylic acid butyl ester and 1,4-Dihydroxy-7-(2-morpholin-4-yl-benzothiazol-6-yloxy)-isoquinoline-3-carboxylic acid butyl ester Sodium (703 mg, 30.6 mmol) was dissolved in anhydrous 1-butanol (35 mL) at 85° C. The resulting freshly prepared solution was added to a solution of [5-(2-morpholin-4-yl-benzothiazol-6-yloxy)-1,3-dioxo-1,3-dihydro-isoindol-2-yl]-acetic acid ethyl ester (7.14 g, 15.3 mmol) in anhydrous 1-butanol (55 mL). The mixture was stirred at 110° C. for 90 minutes before it was cooled to room temperature, acidified with 4N HCl (8 mL) to pH=5. The resulting precipitate was filtered, washed with water, dried in vacuo to give the regioisomeric mixture of title compound as a yellow solid (6.13 g): MS: (+) m/z 496.19 (M+1).

f) 1-Chloro-4-hydroxy-6-(2-morpholin-4-yl-benzothiazol-6-yloxy)-isoquinoline-3-carboxylic acid butyl ester A solution of the regioisomeric mixture of 1,4-dihydroxy-6-(2-morpholin-4-yl-benzothiazol-6-yloxy)-isoquinoline-3-carboxylic acid butyl ester and 1,4-dihydroxy-7-(2-morpholin-4-yl-benzothiazol-6-yloxy)-isoquinoline-3-carboxylic acid butyl ester synthesized as described above (1.51 g, 3.04 mmol), and phosphorus oxychloride (417 μL, 4.56 mmol) in dichloroethane (23 mL) was stirred at 120° C. in a CEM microwave apparatus for thirty minutes. The mixture was then stirred at ambient temperature with saturated sodium bicarbonate solution for one hour. The organic layer was washed with brine, dried over anhydrous sodium sulfate, concentrated in vacuo and the residue was purified by flash column chromatography on silica gel with a gradient of ethyl acetate and dichloromethane to give a solid (1.05 g). It was recrystallized from ethyl acetate to give the title compound as a white solid (484 mg): MS: (+) m/z 514.17 (M+1).

g) 1-Cyano-4-hydroxy-6-(2-morpholin-4-yl-benzothiazol-6-yloxy)-isoquinoline-3-carboxylic acid butyl ester A mixture of 1-Chloro-4-hydroxy-6-(2-morpholin-4-yl-benzothiazol-6-yloxy)-isoquinoline-3-carboxylic acid butyl ester (200 mg, 0.39 mmol), tris(dibenzylideneacetone)-dipalladium(0) (18 mg, 0.02 mmol), 1,1'-bis(diphenylphosphino) ferrocene (22 mg, 0.04 mmol), zinc cyanide (27 mg, 0.23 mmol), zinc (3 mg, 0.05 mmol) and dimethylacetamide (0.93 mL) was stirred at 120° C. for two hours before it was cooled to room temperature, partitioned between ethyl acetate and water, filtered. The filtrate was washed with water and brine, dried over anhydrous sodium sulfate and concentrated in vacuo. The residue was purified by flash column chromatography on silica gel with a gradient of ethyl acetate and dichloromethane to give the title compound as a white solid (137 mg): MS: (+) m/z 505.31 (M+1); (−) m/z 503.31 (M−1).

h) {[1-Cyano-4-hydroxy-6-(2-morpholin-4-yl-benzothiazol-6-yloxy)-isoquinoline-3-carbonyl]-amino}-acetic acid A mixture of 1-cyano-4-hydroxy-6-(2-morpholin-4-yl-benzothiazol-6-yloxy)-isoquinoline-3-carboxylic acid butyl ester (137 mg, 0.27 mmol), glycine (408 mg, 5.43 mmol) and 0.5 M sodium methoxide/methanol (10.3 mL) was refluxed for twenty-six hours before it was cooled to room temperature and concentrated in vacuo. The residue was dissolved in water (40 mL) and extracted with dichloromethane (2×35 mL). The remaining aqueous layer was acidified to pH=3 with 1N HCl (7.5 mL). The white precipitate was filtered, washed with water and dried in vacuo to give the title compound as a white solid (119 mg): MS: (+) m/z 506.26 (M+1); (−) m/z 504.24 (M−1).

Example 43

{[1-Cyano-4-hydroxy-6-(2-methyl-benzooxazol-6-yloxy)-isoquinoline-3-carbonyl]-amino}-acetic acid a) 1-(2,4-Dihydroxy-phenyl)-ethanone oxime

A mixture of 2,4-dihydroxyacetophenone (25 g, 0.16 mol), hydroxylamine hydrochloride (14.8 g, 0.21 mol), sodium acetate (20 g, 0.24 mol) and water/dioxane (300 mL, 1:1) was stirred at room temperature for three days before the mixture was partitioned between chloroform and water. The organic layer was dried over anhydrous sodium sulfate, concentrated in vacuo and the residue was purified by flash column chromatography on silica gel with a gradient of ethyl acetate and dichloromethane to give the title compound as a white solid (11.67 g): $^1$H NMR (CD$_3$OD, 200 MHz): δ=7.26 (m, 1H), 6.28 (m, 2H), 4.88 (s, 2H), 3.29 (m, 1H), 2.24 (s, 3H).

b) 2-Methyl-benzooxazol-6-ol

To a mixture of 1-(2,4-dihydroxy-phenyl)-ethanone oxime (4.2 g, 25 mmol) and acetonitrile/dimethylacetamide (20 mL, 3:1) cooled by a water bath (20-25° C.) was added dropwide phosphorus chloride (2.4 mL, 26.2 mmol) over a period of fifteen minutes. The mixture was stirred for an additional thirty minutes before it was poured into ice water containing sodium acetate (6 g). The mixture was stirred for ten minutes, filtered, and the filter cake was washed with water and dried in vacuo to give the title compound as a yellow solid (3.15 g): $^1$H NMR (CDCl$_3$, 200 MHz): δ=7.45 (m, 1H), 6.96 (m, 1H), 6.80 (m, 1H), 2.60 (s, 3H).

c) [5-(2-Methyl-benzooxazol-6-yloxy)-1,3-dioxo-1,3-dihydro-isoindol-2-yl]-acetic acid ethyl ester A mixture of 2-methyl-benzooxazol-6-ol (8.41 g, 56 mmol), 5-nitro-1,3-dioxo-1,3-dihydro-isoindol-2-yl)-acetic acid ethyl ester (17.23 g, 62 mmol), potassium carbonate (9.36 g, 67.7 mmol) and dimethylacetamide (120 mL) was stirred at 105° C. for twenty hours before it was cooled to room temperature and partitioned between chloroform and water. The organic layer was dried over anhydrous sodium sulfate, concentrated in vacuo and the residue was purified by flash column chromatography on silica gel with a gradient of ethyl acetate and dichloromethane to give the title compound as a yellow solid (9.18 g): MS: (+) m/z 381.27 (M+1).

d) 1,4-Dihydroxy-6-(2-methyl-benzooxazol-6-yloxy)-isoquinoline-3-carboxylic acid butyl ester and 1,4-Dihydroxy-7-(2-methyl-benzooxazol-6-yloxy)-isoquinoline-3-carboxylic acid butyl ester Sodium (1.11 g, 48.2 mmol) was dissolved in anhydrous 1-butanol (60 mL) at 90° C. The resulting freshly prepared solution was added to a solution of [5-(2-methyl-benzooxazol-6-yloxy)-1,3-dioxo-1,3-dihydro-isoindol-2-yl]-acetic acid ethyl ester (9.16 g, 24.1 mmol) in anhydrous 1-butanol (70 mL). The mixture was stirred at 110° C. for two hours before it was cooled to room temperature, acidified with 2N HCl (24 mL) to pH=4. The precipitate was filtered, washed with water, dried in vacuo to give the 6,7-isomeric mixture of title compound as a yellow solid (6.63 g): MS: (+) m/z 409.34 (M+1).

e) 1-Chloro-4-hydroxy-6-(2-methyl-benzooxazol-6-yloxy)-isoquinoline-3-carboxylic acid butyl ester A solution of the regiosomeric mixture of 1,4-dihydroxy-6-(2-methyl-benzooxazol-6-yloxy)-isoquinoline-3-carboxylic acid butyl ester and 1,4-dihydroxy-7-(2-methyl-benzooxazol-6-yloxy)-isoquinoline-3-carboxylic acid butyl ester synthesized as described above (2.5 g, 6.12 mmol), and phosphorus oxychloride (685 μL, 7.35 mmol) in dichloroethane (30 mL) was stirred at 120° C. in a CEM microwave apparatus for thirty minutes. The mixture was stirred at ambient temperature with a saturated sodium bicarbonate solution for thirty minutes. The organic layer was washed with brine, dried over anhydrous sodium sulfate, concentrated in vacuo and the residue was purified by flash column chromatography on silica gel with a gradient of ethyl acetate and dichloromethane to give a solid (1.72 g). It was recrystallized from ethyl acetate (130 mL) to give the title compound as a white solid (844 mg): MS: (+) m/z 427.16 (M+1).

f) 1-Cyano-4-hydroxy-6-(2-methyl-benzooxazol-6-yloxy)-isoquinoline-3-carboxylic acid butyl ester A mixture of 1-chloro-4-hydroxy-6-(2-methyl-benzooxazol-6-yloxy)-isoquinoline-3-carboxylic acid butyl ester (199 mg, 0.47 mmol), tris(dibenzylideneacetone)dipalladium(0) (21 mg, 0.02 mmol), 1,1'-bis(diphenylphosphino)ferrocene (26 mg, 0.04 mmol), zinc cyanide (33 mg, 0.28 mmol), zinc (4 mg, 0.06 mmol) and dimethylacetamide (1.1 mL) was stirred at 120° C. for two hours before it was cooled to room temperature, partitioned between ethyl acetate and water, filtered. The filtrate was washed with water and brine, dried over anhydrous sodium sulfate and concentrated in vacuo. The residue was purified by flash column chromatography on silica gel with a gradient of ethyl acetate and dichloromethane to give the title compound as a white solid (80 mg): MS: (+) m/z 418.38 (M+1).

g) {[1-Cyano-4-hydroxy-6-(2-methyl-benzooxazol-6-yloxy)-isoquinoline-3-carbonyl]-amino}-acetic acid A mixture of 1-cyano-4-hydroxy-6-(2-methyl-benzooxazol-6-yloxy)-isoquinoline-3-carboxylic acid butyl ester (81 mg, 0.19 mmol), glycine (292 mg, 3.89 mmol), and 0.5 M sodium methoxide/methanol (7.4 mL) was refluxed for twenty-six hours before it was cooled to room temperature and concentrated in vacuo. The residue was dissolved in water (25 mL) and extracted with dichloromethane (2×35 mL). The remaining aqueous layer was acidified to pH=3 with 1N HCl (5.5 mL). The precipitate was filtered, washed with water and dried in vacuo to give the title compound as a brown solid (72 mg): MS: (+) m/z 419.30 (M+1); (−) m/z 417.28 (M−1).

Example 44

[(6-Chloro-1-cyano-4-hydroxy-isoquinoline-3-carbonyl)-amino]-acetic acid a) 6-Chloro-1-cyano-4-hydroxy-isoquinoline-3-carboxylic acid butyl ester A mixture of 1-bromo-6-chloro-4-hydroxy-isoquinoline-3-carboxylic acid butyl ester (509 mg, 1.43 mmol; prepared according to US 2004/0254215 A1), copper (I) cyanide (255 mg, 2.85 mmol) and anhydrous dimethylformamide (6 mL) was refluxed for twenty-five minutes before it was cooled to room temperature and quenched with water. Chloroform/2-propanol (75 mL, 3:1) was added and the mixture was stirred for ten minutes before it was filtered. The organic layer was washed with water, brine, dried over anhydrous sodium sulfate, concentrated in vacuo and the residue was purified by flash column chromatography on silica gel with a gradient of ethyl acetate and dichloromethane to give the title compound as a yellow solid (280 mg): MS: (−) m/z 303.20 (M−1).

b) [(6-Chloro-1-cyano-4-hydroxy-isoquinoline-3-carbonyl)-amino]-acetic acid

A mixture of 6-chloro-1-cyano-4-hydroxy-isoquinoline-3-carboxylic acid butyl ester (99 mg, 0.33 mmol) and glycine (1.84 g, 24.49 mmol) in 0.5 M sodium methoxide/methanol (32.6 mL) was refluxed for twenty-one hours before it was cooled to room temperature and concentrated in vacuo. The residue was dissolved in water (40 mL) and the solution washed with dichloromethane (3×50 mL). The remaining aqueous layer was acidified to pH=3 with 1N HCl. The suspension was extracted with ethyl acetate (50 mL). The organic layer was dried over anhydrous sodium sulfate and concentrated in vacuo to give the title compound as a white solid (84 mg): MS: (+) m/z 306.27 (M+1); (−) m/z 304.26 (M−1).

Example 45

[(7-Butoxy-1-cyano-4-hydroxy-isoquinoline-3-carbonyl)-amino]-acetic acid

[(7-Butoxy-1-cyano-4-hydroxy-isoquinoline-3-carbonyl)-amino]-acetic acid was prepared by adding 135 mg (0.383 mmol) of [(7-butoxy-1-chloro-4-hydroxy-isoquinoline-3-carbonyl)-amino]-acetic (prepared according to U.S. Pat. No. 6,093,730), 18 mg (0.02 mmol) tris(dibenzylideneacetone)dipalladium(0), 22.2 mg (0.04 mmol) 1,1'-bis(diphenylphosphino) ferrocene, 3 mg (0.04 mmol) zinc dust, and 27 mg (0.23 mmol) zinc cyanide to 0.80 mL of N,N-dimethylacetamide. The resultant mixture was heated at 115° C. for 3 hours under a nitrogen atmosphere, and then cooled to room temperature. The mixture was diluted with ethyl acetate and extracted three times with aqueous sodium bicarbonate solution. The aqueous extracts were acidified with concentrated HCl, and the resultant white precipitate was collected: 28 mg of the title compound; MS (ESI−): m/z 342.0 (M−1)

Example 46

[(1-Cyano-4-hydroxy-6,7-diphenoxy-isoquinoline-3-carbonyl)-amino]-acetic acid

[(1-Cyano-4-hydroxy-6,7-diphenoxy-isoquinoline-3-carbonyl)-amino]-acetic acid was prepared by adding 76 mg (0.164 mmol) of [(1-chloro-4-hydroxy-6,7-diphenoxy-isoquinoline-3-carbonyl)-amino]-acetic acid (prepared according to US 2006/0217416), 7.3 mg (0.008 mmol) tris(dibenzylideneacetone)dipalladium(0), 9.0 mg (0.016 mmol) 1,1'-bis(diphenylphosphino) ferrocene, 1.3 mg (0.020 mmol) zinc dust, and 12 mg (0.10 mmol) zinc cyanide to 0.35 mL of N,N-dimethylacetamide. The resultant mixture was heated at 115° C. for 3 hours under a nitrogen atmosphere, and then cooled to room temperature. The mixture was diluted with ethyl acetate and extracted three times with aqueous sodium bicarbonate and twice with 1 N NaOH solutions. The basic aqueous extracts were acidified with concentrated HCl, and extracted three times with ethyl acetate. The organic extracts were dried over sodium sulfate and concentrated to give 29 mg of the title compound as a white solid; MS (ESI−): m/z 454.0 (M−1)

Example 47

[(1-Cyano-4-hydroxy-7-methoxy-isoquinoline-3-carbonyl)-amino]-acetic acid

[(1-Cyano-4-hydroxy-7-methoxy-isoquinoline-3-carbonyl)-amino]-acetic acid was prepared by adding 159 mg (0.511 mmol) of [(1-chloro-4-hydroxy-7-methoxy-isoquinoline-3-carbonyl)-amino]-acetic acid (prepared according to U.S. Pat. No. 6,093,730), 24 mg (0.025 mmol) tris(dibenzylideneacetone)dipalladium(0), 28 mg (0.051 mmol) 1,1'-bis(diphenylphosphino) ferrocene, 4 mg (0.06 mmol) zinc dust, and 36 mg (0.306 mmol) zinc cyanide to 1.0 mL of N,N-dimethylacetamide. The resultant mixture was heated at 115° C. for 3 hours under a nitrogen atmosphere, and then cooled to room temperature. The mixture was diluted with ethyl acetate and half-saturated aqueous sodium bicarbonate solution and filtered through a celite pad. The biphasic mixture was separated, and the basic aqueous extract was acidified with concentrated HCl and extracted three times with ethyl acetate. The organic extracts were dried over sodium sulfate and concentrated to give 107 mg of the title compound as a white solid; MS (ESI+): m/z 302.3 (M+1)

Example 48

[(1-Cyano-4-hydroxy-7-isopropoxy-isoquinoline-3-carbonyl)-amino]-acetic acid

[(1-Cyano-4-hydroxy-7-isopropoxy-isoquinoline-3-carbonyl)-amino]-acetic acid was prepared from [(1-chloro-4-hydroxy-7-isopropoxy-isoquinoline-3-carbonyl)-amino]-acetic acid (prepared according to U.S. Pat. No. 6,093,730) under conditions analogous to example 47a; MS (ESI+): m/z 330.3 (M+1)

Example 49

[(1-Cyano-4-hydroxy-6-isopropoxy-isoquinoline-3-carbonyl)-amino]-acetic acid

[(1-Cyano-4-hydroxy-6-isopropoxy-isoquinoline-3-carbonyl)-amino]-acetic acid was prepared from [(1-chloro-4-hydroxy-6-isopropoxy-isoquinoline-3-carbonyl)-amino]-acetic acid (prepared according to US2006/217416) under conditions analogous to example 47a; MS (ESI+): m/z 330.3 (M+1)

Example 50

[(1-Cyano-4-hydroxy-5-phenyl-isoquinoline-3-carbonyl)-amino]-acetic acid

[(1-Cyano-4-hydroxy-5-phenyl-isoquinoline-3-carbonyl)-amino]-acetic acid was prepared from [(1-chloro-4-hydroxy-5-phenyl-isoquinoline-3-carbonyl)-amino]-acetic acid (prepared according to US2006/217416) under conditions analogous to example 47a; MS (ESI+): m/z 348.3 (M+1)

Example 51

[(1-Cyano-4-hydroxy-8-phenyl-isoquinoline-3-carbonyl)-amino]-acetic acid

[(1-Cyano-4-hydroxy-8-phenyl-isoquinoline-3-carbonyl)-amino]-acetic acid was prepared from [(1-Chloro-4-hydroxy-8-phenyl-isoquinoline-3-carbonyl)-amino]-acetic acid (prepared according to US2006/217416) under conditions analogous to example 47a; MS (ESI+): m/z 348.3 (M+1)

Example 52

[(7-Benzyloxy-1-cyano-4-hydroxy-isoquinoline-3-carbonyl)-amino]-acetic acid a) (2,4-Dimethoxy-benzylamino)-acetic acid ethyl ester A mixture of 2,4-dimethoxy-benzaldehyde (50 g, 0.30 mole), glycine ethyl ester hydrochloride (44 g, 0.32 mole) and triethylamine (43.9 mL, 0.32 mole) in dichloroethane was stirred for one hour before sodium triacetoxyborohydride (100 g, 0.47 mole) was added in four portions. The mixture was stirred for three days before it was quenched with saturated sodium bicarbonate. The organic layer was extracted with 3N HCl (2×400 mL, 2.4 mole). The aqueous layers were combined, adjusted with solid sodium hydroxide (97.68 g, 2.4 mole) to pH=8 and extracted with ethyl acetate (500 mL). The ethyl acetate extract was washed with brine, dried over sodium sulfate, and concentrated. The residue was purified by flash column chromatography with a gradient of methanol and dichloromethane on silica gel (120 g) to give the title compound as a yellow oil (42.77 g) $^1$H NMR (CDCl$_3$, 200 MHz): δ=7.11 (m, 1H), 6.41 (m, 2H), 4.15 (q, J=7.2 Hz, 2H), 3.81 (s, 3H), 3.80 (s, 3H), 3.74 (s, 2H), 3.37 (s, 2H), 1.27 (t, J=7.2 Hz, 3H).

b) 4-(tert-Butyl-dimethyl-silanyloxy)-2-methyl-benzoic acid ethyl ester

A mixture of 18 g (100 mmol) of 4-hydroxy-2-methyl-benzoic acid ethyl ester (prepared according to Sen, et. al. (1987), Indian J. Chem. Sec B, 26: 679-682), 10.2 g (150 mmol) of imidazole, and 17.2 g (115 mmol) of tert-butyldimethylsilyl chloride in 110 mL of anhydrous DMF was stirred for 24 hours at room temperature. The reaction was diluted with water and extracted with ethyl acetate. The organic fraction was washed with water, 0.1 N HCl, and brine, then dried over anhydrous magnesium sulfate and concentrated to 28.8 g of the title compound; MS (ESI+): m/z 295.5 (M+1)

c) N-(2,4-dimethoxy-benzyl),N-(2-ethoxycarbonyl-5-hydroxy-benzyl)glycine ethyl ester A mixture of 20 g (68 mmol) of 4-(tert-butyl-dimethyl-silanyloxy)-2-methyl-benzoic acid ethyl ester, 12.1 g (68 mmol) of N-bromosuccinimide, 1.5 g (6.8 mmol) of benzoyl peroxide in 230 mL of carbon tetrachloride was heated at reflux temperature for 5 hours. The resultant mixture was cooled, filtered through a plug of silica gel, and concentrated under reduced pressure. To the residue (12.2 g) was added 8.0 g (28.7 mmol) of N-(2,4-dimethoxy-benzyl)glycine ethyl ester, 3.96 g (28.7 mmol) of potassium carbonate, and 65 mL of anhydrous DMF and the mixture was stirred for 6.5 hours. The mixture was then partitioned into a biphasic water-ethyl acetate mixture and the isolated organic layer was washed with brine, dried over anhydrous magnesium sulfate, and concentrated. The residue was purified by flash chromatography: eluting the desired product from silica gel with a gradient of 10-90% ethyl acetate in hexanes. 5.33 g of the title compound (yellow oil) was isolated; MS (ESI+): 432.2 (M+1)

d) N-(2,4-dimethoxy-benzyl),N-(5-benzyloxy-2-ethoxycarbonyl-benzyl)glycine ethyl ester A solution of 5.3 g (12.3 mmol) of N-(2,4-dimethoxy-benzyl),N-(2-ethoxycarbonyl-5-hydroxy-benzyl)glycine ethyl ester, 1.8 mL (15.4 mmol) benzylbromide, and 4.4 g (13.5 mmol) cesium carbonate in 35 mL of anhydrous DMF was stirred for 18 hours. The reaction mixture was partitioned between diethyl ether and water, and the organic fraction washed with saturated aqueous sodium bicarbonate, brine, dried over anhydrous sodium sulfate, filtered through a pad of silica gel, and concentrated under reduced pressure to 6.4 g of the title compound. MS (ESI+) 522.5 e/z (M+1)

e) 7-Benzyloxy-2-(2,4-dimethoxy-benzyl)-4-hydroxy-1,2-dihydro-isoquinoline-3-carboxylic acid ethyl ester A solution of 6.4 g (12.3 mmol) of N-(2,4-dimethoxy-benzyl),N-(5-benzyloxy-2-ethoxycarbonyl-benzyl)glycine ethyl ester in 140 mL of anhydrous THF was cooled in an ice bath. 24.6 mL of 1 N potassium tert-butoxide in THF was added slowly to the stirring cold solution. The reaction mixture was stirred at 0° C. for 1 hour and then allowed to warm to room temperature and stirred for 4 hours. The mixture was poured into a biphasic mixture of ethyl acetate and saturated aqueous ammonium chloride. The organic fraction was washed twice with brine, dried over anhydrous sodium sulfate, and concentrated under reduced pressure to give 5.7 g of the title compound; MS (ESI+): 476.3 e/z (M+1)

f) 7-Benzyloxy-4-hydroxy-isoquinoline-3-carboxylic acid ethyl ester

Dichloromethane (100 mL) was cooled to 0° C. and 5.7 g (12 mmol) of 7-benzyloxy-2-(2,4-dimethoxy-benzyl)-4-hydroxy-1,2-dihydro-isoquinoline-3-carboxylic acid ethyl ester and 1.31 mL (18 mmol) of thionyl chloride were added. The reaction was stirred for one hour and then allowed to warm to room temperature and stirred for an additional 3 hours. 60 mL of hexanes was added to the resultant slurry and the white solid was collected by filtration through a medium glass fritted filter. The solid was partitioned between ethyl acetate and saturated sodium bicarbonate solution and the organic phase was washed with brine, dried over anhydrous sodium sulfate, and concentrated to give the title compound (2.7 g, white solid); MS (ESI+): 324.3 e/z (M+1)

g) 7-Benzyloxy-1-bromo-4-hydroxy-isoquinoline-3-carboxylic acid ethyl ester

A suspension of 2.48 g (7.67 mmol) of 7-benzyloxy-4-hydroxy-isoquinoline-3-carboxylic acid ethyl ester and 1.43 g (8.0 mmol) of N-bromosuccinimide in 25 mL of acetonitrile was heated to 70° C. for ten minutes. The reaction was cooled and a white solid precipitated out of solution. The solid was collected by filtration through a medium glass fritted filter and washed with cold acetonitrile to give 2.3 g of the title compound; MS (ESI+): 402.2, 404.2 e/z (M+1, $^{79}$Br/$^{81}$Br)

h) 7-Benzyloxy-1-cyano-4-hydroxy-isoquinoline-3-carboxylic acid ethyl ester

7-Benzyloxy-1-cyano-4-hydroxy-isoquinoline-3-carboxylic acid ethyl ester was prepared by heating a mixture of 1.76 g (4.4 mmol) of 7-benzyloxy-1-bromo-4-hydroxy-isoquinoline-3-carboxylic acid ethyl ester, 201 mg (0.2.0 mmol) tris(dibenzylideneacetone)dipalladium(0), 243 mg (0.44 mmol) 1,1'-bis(diphenylphosphino) ferrocene, 34 mg (0.53 mmol) zinc dust, 309 mg (2.64 mmol) zinc cyanide, and 9.0 mL of N,N-dimethylacetamide at 115 deg C. for 3 hours. The resultant mixture was diluted with ethyl acetate and saturated aqueous ammonium chloride and filtered through a celite pad. The organic fraction was washed with saturated ammonium chloride, water, brine, dried over anhydrous sodium sulfate, and concentrated in vacuo. The residue was purified by flash chromatography, eluting from silica gel with a 10 to 90 percent gradient of ethyl acetate in hexanes to give 1.18 g of the title compound; MS (ESI+): 349.3 e/z (M+1)

i) [(7-Benzyloxy-1-cyano-4-hydroxy-isoquinoline-3-carbonyl)-amino]-acetic acid

[(7-Benzyloxy-1-cyano-4-hydroxy-isoquinoline-3-carbonyl)-amino]-acetic acid was prepared by heating a solution of 110 mg (0.316 mmol) of 7-benzyloxy-1-cyano-4-hydroxy-isoquinoline-3-carboxylic acid ethyl ester and 210 mg (2.8 mmol) of glycine in 5 mL of 0.5 N NaOMe in methanol at reflux temperature for 28 hours. The reaction mixture was cooled and acidified with 3 mL of 1 N HCl. A white solid was collected on a medium glass fritted filter to provide 115 mg of the title compound; MS (ESI+): 378.2 e/z (M+1)

Example 53

[(1-Cyano-4,7-dihydroxy-isoquinoline-3-carbonyl)-amino]-acetic acid a) 1-Cyano-4,7-dihydroxy-isoquinoline-3-carboxylic acid ethyl ester 1-Cyano-4,7-dihydroxy-isoquinoline-3-carboxylic acid ethyl ester was prepared by heating a mixture of 175 mg (0.50 mmol) of 7-Benzyloxy-1-cyano-4-hydroxy-isoquinoline-3-carboxylic acid ethyl ester (example 52h), 630 mg (10 mmol) of ammonium formate, and 40 mg of 10% Pd/C in 3 mL of 1:1 EtOAc and EtOH at reflux temperature for 40 min. The resultant mixture was cooled, filtered through a celite pad to remove solids, and concentrated to a crude solid. The solid was triturated with hot ethanol to give 56 mg of off-white solid upon drying; MS (ESI+): 259.3 e/z (M+1)

b) [(1-Cyano-4,7-dihydroxy-isoquinoline-3-carbonyl)-amino]-acetic acid

[(1-Cyano-4,7-dihydroxy-isoquinoline-3-carbonyl)-amino]-acetic acid was prepared by heating a mixture of 42 mg (0.162 mmol) of 1-Cyano-4,7 dihydroxy-isoquinoline-3-carboxylic acid ethyl ester and 97 mg (1.29 mmol) of glycine in 2.25 mL of 0.5 N NaOMe in methanol at reflux temperature for 26 hours. The reaction mixture was cooled and acidified with 3 mL of 1 N HCl and water. A white solid was collected on a medium glass fritted filter to provide 40 mg of the title compound; MS (ESI+): 288.2 e/z (M+1)

Example 54

Comparative Assay of Compounds with Chloro, Bromo, Hydrogen, or Methyl in Place of Cyano at C-1 Position Compounds were tested for activity using the following assay. Compounds were dissolved in aqueous solution containing twice as much sodium hydroxide, mole-for-mole, as compound and dextrose as tonicity agent. Male Swiss Webster mice were dosed by tail vein injection with the compound, and blood samples were collected into EDTA and heparin 4 hours post IV dosing. The samples were analyzed using a mouse erythropoietin QUANTIKINE ELISA kit (R&D Systems Inc., Minneapolis Minn.) according to the manufacturer's instructions. Compounds of the present invention showed measurable increase in plasma erythropoietin levels. Further, compounds containing the cyano substitution at C-1, as presently claimed, surprisingly produce higher, e.g., at least two times higher, plasma erythropoietin levels than a comparable compound containing a hydrogen, chloro, bromo, or methyl at C-1 position at a given dose. Table 1 below illustrates the fold difference (i.e., the level of improvement) between erythropoietin levels achieved by compounds of the invention compared to erythropoietin levels achieved by compounds having the same structure except the cyano group at the C-1 position is replaced as shown below, tested under the same conditions and at the same concentration.

TABLE 1

| Example | Comparative Substituent | Fold Difference |
|---|---|---|
| 1 | —Cl | 4.7× |
| 3 | —CH$_3$ | 2.5× |
| 6 | —Cl | 31× |
| 9 | —CH$_3$ | 2.4× |
| 12 | —Cl | 449× |
| 12 | —Br | 362× |
| 39 | —CH$_3$ | 178× |
| 40 | —H | 81× |
| 20 | —H | 23× |
| 22 | —H | 26× |
| 23 | —H | 277× |

What is claimed is:

1. A compound represented by formula I:

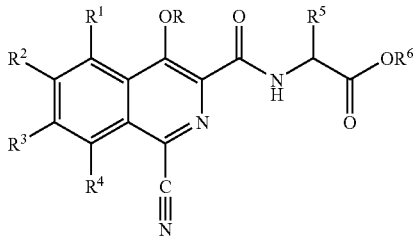

wherein:
R is selected from the group consisting of hydrogen, alkyl, and substituted alkyl;
$R^1$, $R^2$, $R^3$ and $R^4$ are independently selected from the group consisting of hydrogen, halo, cyano, hydroxyl, alkyl, substituted alkyl, aryl, substituted aryl, heteroaryl, substituted heteroaryl, amino, substituted amino, —$OR^7$, —$SR^7$, —$SOR^7$, and —$SO_2R^7$ wherein $R^7$ is selected from the group consisting of alkyl, substituted alkyl, cycloalkyl, substituted cycloalkyl, aryl, substituted aryl, heteroaryl, and substituted heteroaryl;
$R^5$ and $R^6$ are independently selected from the group consisting of hydrogen or $C_{1-3}$ alkyl;
or a pharmaceutically acceptable salt, tautomer, or stereoisomer thereof; or an ester or amide of the carboxylic acid moiety on the glycine or alanine-based substituent of the cyanoisoquinoline ring.

2. The compound of claim 1, wherein at least two of $R^1$, $R^2$, $R^3$ and $R^4$ are hydrogen.

3. The compound of claim 1, wherein $R^1$, $R^2$, $R^3$, and $R^4$ are independently selected from the group consisting of hydrogen, hydroxyl, halo, substituted alkyl, aryl, —$OR^7$, —$SR^7$, and —$SO_2R^7$ wherein $R^7$ is selected from the group consisting of alkyl, substituted alkyl, cycloalkyl, aryl, substituted aryl, heteroaryl, and substituted heteroaryl.

4. The compound of claim 1, wherein $R^1$, $R^2$, $R^3$, and $R^4$ are selected from the group consisting of hydrogen, halo, haloalkyl, alkyl, alkoxy, aryloxy and substituted aryloxy.

5. The compound of claim 3, wherein $R^1$, $R^2$, $R^3$, and $R^4$ are independently selected from the group consisting of hydrogen, hydroxyl, phenyl, chloro, trifluoromethyl, benzyl, benzyloxy, methoxy, butoxy, isopropoxy, phenoxy, 4-fluorophenoxy, 2-methoxyphenoxy, 3-methoxyphenoxy, 4-methoxyphenoxy, 2,6-dimethylphenoxy, 2-ethyl-6-methylphenoxy, 2,4,6-trimethylphenoxy, 4-chloro-2,6-dimethylphenoxy, 4-propoxyphenoxy, 2,3-dihydro-benzofuran-5-yloxy, 2-methyl-benzothiazol-6-yloxy, 2-dimethylamino-benzooxazol-5-yloxy, 2-morpholin-4-yl-benzothiazol-6-yloxy, 2-methyl-benzooxazol-6-yloxy, benzo[1,3]dioxo-5-yloxy, phenylsulfanyl, phenylsulfonyl, and cyclohexyloxy.

6. The compound of claim 5, wherein $R^1$, $R^2$, $R^3$, and $R^4$ are selected from the group consisting of hydrogen, chloro, methoxy, trifluoromethyl, phenoxy, and 4-fluorophenoxy.

7. The compound of claim 5, wherein $R^1$ and $R^4$ are hydrogen.

8. The compound of claim 5, wherein $R^1$, $R^3$ and $R^4$ are hydrogen.

9. The compound of claim 5, wherein $R^1$, $R^2$ and $R^3$ are hydrogen.

10. The compound of claim 5, wherein $R^1$, $R^2$, and $R^4$ are hydrogen.

11. The compound of claim 5, wherein $R^2$, $R^3$, and $R^4$ are hydrogen.

12. The compound of claim 5, wherein $R^1$, $R^2$, $R^3$, and $R^4$ are hydrogen.

13. The compound of claim 11, where $R^1$ is selected from the group consisting of phenyl, phenoxy and 4-fluorophenoxy.

14. The compound of claim 1, wherein $R^2$ is selected from the group consisting of halo, cyano, hydroxyl, alkyl, substituted alkyl, aryl, substituted aryl, heteroaryl, substituted heteroaryl, amino, substituted amino, —$OR^7$, —$SR^7$, —$SOR^7$, and —$SO_2R^7$ wherein $R^7$ is selected from the group consisting of alkyl, substituted alkyl, cycloalkyl, substituted cycloalkyl, aryl, substituted aryl, heteroaryl, and substituted heteroaryl.

15. The compound of claim 14, wherein $R^2$ is selected from the group consisting of halo, —$OR^7$, —$SR^7$, —$SOR^7$, and —$SO_2R^7$ wherein $R^7$ is selected from the group consisting of alkyl, substituted alkyl, cycloalkyl, aryl, substituted aryl, heteroaryl, and substituted heteroaryl.

16. The compound of claim 14, wherein $R^2$ is selected from the group consisting of chloro, methoxy, isopropoxy, phenoxy, 4-fluorophenoxy, 4-methoxyphenoxy, 2,6-dimethylphenoxy, 2-ethyl-6-methylphenoxy, 2,4,6-trimethylphenoxy, 4-chloro-2,6-dimethylphenoxy, 4-propoxyphenoxy, 2,3-dihydro-benzofuran-5-yloxy, 2-methyl-benzothiazol-6-yloxy, 2-dimethylamino-benzooxazol-5-yloxy, 2-morpholin-4-yl-benzothiazol-6-yloxy, 2-methyl-benzooxazol-6-yloxy, benzo[1,3]dioxo-5-yloxy, phenylsulfonyl, phenylsulfanyl, and cyclohexyloxy.

17. The compound of claim 14, wherein $R^2$ is methoxy, phenoxy, or 4-fluorophenoxy.

18. The compound of claim 1, wherein $R^3$ is selected from the group consisting of hydroxyl, halo, haloalkyl, substituted alkyl, —$OR^7$, —$SR^7$, —$SOR^7$, and —$SO_2R^7$ wherein $R^7$ is selected from the group consisting of alkyl, substituted alkyl, aryl, substituted aryl, heteroaryl, and substituted heteroaryl.

19. The compound of claim 18, wherein $R^3$ is selected from the group consisting of trifluoromethyl, chloro, hydroxyl, benzyl, methoxy, isopropoxy, butoxy, benzyloxy, phenoxy, 4-fluorophenoxy, 2,6-dimethylphenoxy, 4-methoxyphenoxy, 2-dimethylamino-benzooxazol-5-yloxy, benzo[1,3]dioxo-5-yloxy, and phenylsulfanyl.

20. The compound of claim 18, wherein $R^3$ is phenoxy, 4-fluorophenoxy, trifluoromethyl, or chloro.

21. The compound of claim 1, wherein $R^4$ is selected from the group consisting of phenyl, phenoxy, 2-methoxyphenoxy, 3-methoxyphenoxy, 4-methoxyphenoxy, and 4-fluorophenoxy.

22. The compound of claim 21, wherein $R^4$ is phenoxy or 4-fluorophenoxy.

23. The compound of claim 1, wherein $R^5$ is hydrogen.

24. The compound of claim 1, wherein $R^5$ is methyl.

25. The compound of claim 1, wherein $R^6$ is hydrogen.

26. The compound of claim 1, wherein $R^6$ is methyl.

27. The compound of claim 1, wherein R is hydrogen.

28. The compound of claim 1, wherein R is methyl.

29. The compound of claim 1, wherein the compound is of formula II:

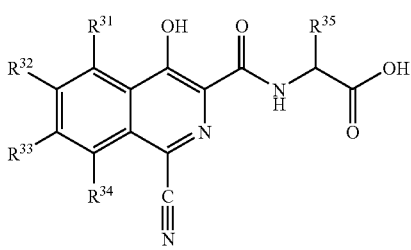

wherein:
R³¹, R³², R³³ and R³⁴ are independently selected from the group consisting of hydrogen, cyano, hydroxyl, halo, alkyl, substituted alkyl, aryl, substituted aryl, heteroaryl, substituted heteroaryl, amino, substituted amino, —OR³⁷, —SR³⁷, —SOR³⁷, and —SO₂R³⁷ wherein R³⁷ is selected from the group consisting of alkyl, substituted alkyl, cycloalkyl, substituted cycloalkyl, aryl, substituted aryl, heteroaryl, and substituted heteroaryl;
R³⁵ is hydrogen or methyl;
or a pharmaceutically acceptable salt, tautomer, or stereoisomer thereof; or an ester or amide of the carboxylic acid moiety on the glycine- or alanine-based substituent of the cyanoisoquinoline ring.

30. The compound of claim 29, wherein at least three of R³¹, R³², R³³, and R³⁴ are hydrogen.

31. The compound of claim 29, wherein R³¹, R³², R³³ and R³⁴ are independently selected from the group consisting of hydrogen, halo, hydroxy, alkyl, substituted alkyl, haloalkyl, alkoxy, substituted alkoxy, aryl, substituted aryl, aryloxy, substituted aryloxy, heteroaryloxy, substituted heteroaryloxy, cycloalkoxy, substituted cycloalkoxy, amino, and substituted amino; and
R³⁵ is hydrogen or methyl.

32. The compound of claim 29, wherein R³¹, R³², R³³ and R³⁴ are independently selected from the group consisting of hydrogen, substituted alkyl, aryl, aryloxy, and substituted aryloxy; and
R³⁵ is hydrogen or methyl.

33. A compound selected from the group consisting of:
{[1-cyano-4-hydroxy-isoquinoline-3-carbonyl]-amino}-acetic acid,
2-(S)-[(1-cyano-4-hydroxy-isoquinoline-3-carbonyl)-amino]-propionic acid,
{[1-cyano-4-hydroxy-7-phenoxy-isoquinoline-3-carbonyl]-amino}-acetic acid,
2-(S)-[(1-cyano-4-hydroxy-7-phenoxy-isoquinoline-3-carbonyl)-amino]-propionic acid,
2-(R)-[(1-cyano-4-hydroxy-7-phenoxy-isoquinoline-3-carbonyl)-amino]-propionic acid,
{[1-cyano-7-(4-fluorophenoxy)-4-hydroxy-isoquinoline-3-carbonyl]-amino}-acetic acid,
{[1-cyano-4-hydroxy-7-(trifluoromethyl)-isoquinoline-3-carbonyl]-amino}-acetic acid,
{[1-cyano-4-hydroxy-7-chloro-isoquinoline-3-carbonyl]-amino}-acetic acid,
{[1-cyano-4-hydroxy-8-phenoxy-isoquinoline-3-carbonyl]amino}-acetic acid,
{[1-cyano-8-(4-fluoro-phenoxy)-4-hydroxy-isoquinoline-3-carbonyl]-amino}-acetic acid,
[(1-cyano-4-hydroxy-6-methoxy-isoquinoline-3-carbonyl)-amino]-acetic acid,
[(1-cyano-4-hydroxy-6-phenoxy-isoquinoline-3-carbonyl)-amino]-acetic acid,
{[1-cyano-6-(4-fluoro-phenoxy)-4-hydroxy-isoquinoline-3-carbonyl]-amino}-acetic acid,
{[1-cyano-4-hydroxy-6-(4-methoxy-phenoxy)-isoquinoline-3-carbonyl]-amino}-acetic acid,
[(1-cyano-4-hydroxy-6-phenylsulfanyl-isoquinoline-3-carbonyl)-amino]-acetic acid,
[(1-cyano-4-hydroxy-7-phenylsulfanyl-isoquinoline-3-carbonyl)-amino]-acetic acid,
{[1-cyano-6-(2,6-dimethyl-phenoxy)-4-hydroxy-isoquinoline-3-carbonyl]-amino}-acetic acid,
[(1-cyano-4-hydroxy-5-phenoxy-isoquinoline-3-carbonyl)-amino]-acetic acid,
{[1-cyano-4-hydroxy-8-(4-methoxy-phenoxy)-isoquinoline-3-carbonyl]-amino}-acetic acid,
{[1-cyano-4-hydroxy-8-(3-methoxy-phenoxy)-isoquinoline-3-carbonyl]-amino}-acetic acid,
{[1-cyano-4-hydroxy-8-(2-methoxy-phenoxy)-isoquinoline-3-carbonyl]-amino}-acetic acid,
[(7-benzyl-1-cyano-4-hydroxy-isoquinoline-3-carbonyl)-amino]-acetic acid,
{[1-cyano-5-(4-fluoro-phenoxy)-4-hydroxy-isoquinoline-3-carbonyl]-amino}-acetic acid,
{[1-cyano-7-(2,6-dimethyl-phenoxy)-4-hydroxy-isoquinoline-3-carbonyl]-amino}-acetic acid,
{[1-cyano-6-(2-ethyl-6-methyl-phenoxy)-4-hydroxy-isoquinoline-3-carbonyl]-amino}-acetic acid,
{[1-cyano-4-hydroxy-6-(2,4,6-trimethyl-phenoxy)-isoquinoline-3-carbonyl]-amino}-acetic acid,
{[6-(4-chloro-2,6-dimethyl-phenoxy)-1-cyano-4-hydroxy-isoquinoline-3-carbonyl]-amino}-acetic acid,
{[1-cyano-4-hydroxy-7-(4-methoxy-phenoxy)-isoquinoline-3-carbonyl]-amino}-acetic acid,
[(1-cyano-6-cyclohexyloxy-4-hydroxy-isoquinoline-3-carbonyl)-amino]-acetic acid,
[(6-benzenesulfonyl-1-cyano-4-hydroxy-isoquinoline-3-carbonyl)-amino]-acetic acid,
{[1-cyano-4-hydroxy-6-(4-propoxy-phenoxy)-isoquinoline-3-carbonyl]-amino}-acetic acid,
{[7-(benzo[1,3]dioxol-5-yloxy)-1-cyano-4-hydroxy-isoquinoline-3-carbonyl]-amino}-acetic acid,
{[6-(benzo[1,3]dioxol-5-yloxy)-1-cyano-4-hydroxy-isoquinoline-3-carbonyl]-amino}-acetic acid,
{[1-cyano-6-(2,3-dihydro-benzofuran-5-yloxy)-4-hydroxy-isoquinoline-3-carbonyl]-amino}-acetic acid,
[(1-cyano-4-methoxy-8-phenoxy-isoquinoline-3-carbonyl)-amino]-acetic acid methyl ester,
[(1-cyano-4-methoxy-8-phenoxy-isoquinoline-3-carbonyl)-amino]-acetic acid,
(S)-2-[(1-cyano-4-hydroxy-8-phenoxy-isoquinoline-3-carbonyl)-amino]-propionic acid,
(R)-2-[(1-cyano-4-hydroxy-8-phenoxy-isoquinoline-3-carbonyl)-amino]-propionic acid,
{[1-cyano-4-hydroxy-6-(2-methyl-benzothiazol-6-yloxy)-isoquinoline-3-carbonyl]-amino}-acetic acid,
{[1-cyano-6-(2-dimethylamino-benzooxazol-5-yloxy)-4-hydroxy-isoquinoline-3-carbonyl]-amino}-acetic acid,
{[1-cyano-7-(2-dimethylamino-benzooxazol-5-yloxy)-4-hydroxy-isoquinoline-3-carbonyl]-amino}-acetic acid,
{[1-cyano-4-hydroxy-6-(2-morpholin-4-yl-benzothiazol-6-yloxy)-isoquinoline-3-carbonyl]-amino}-acetic acid,
{[1-cyano-4-hydroxy-6-(2-methyl-benzooxazol-6-yloxy)-isoquinoline-3-carbonyl]-amino}-acetic acid,
[(6-chloro-1-cyano-4-hydroxy-isoquinoline-3-carbonyl)-amino]-acetic acid,

[(7-butoxy-1-cyano-4-hydroxy-isoquinoline-3-carbonyl)-amino]-acetic acid,
[(1-cyano-4-hydroxy-6,7-diphenoxy-isoquinoline-3-carbonyl)-amino]-acetic acid,
[(1-cyano-4-hydroxy-7-methoxy-isoquinoline-3-carbonyl)-amino]-acetic acid,
[(1-cyano-4-hydroxy-7-isopropoxy-isoquinoline-3-carbonyl)-amino]-acetic acid,
[(1-cyano-4-hydroxy-6-isopropoxy-isoquinoline-3-carbonyl)-amino]-acetic acid,
[(1-cyano-4-hydroxy-5-phenyl-isoquinoline-3-carbonyl)-amino]-acetic acid,
[(1-cyano-4-hydroxy-8-phenyl-isoquinoline-3-carbonyl)-amino]-acetic acid,
[(7-benzyloxy-1-cyano-4-hydroxy-isoquinoline-3-carbonyl)-amino]-acetic acid,
and [(1-cyano-4,7-dihydroxy-isoquinoline-3-carbonyl)-amino]-acetic acid,
or a pharmaceutically acceptable salt, tautomer, or stereoisomer thereof; or an ester or amide of the carboxylic acid moiety on the glycine- or alanine-based substituent of the cyanoisoquinoline ring.

34. A pharmaceutical composition comprising one or more compounds of claim 1 and a pharmaceutically acceptable excipient.

35. The composition of claim 34, further comprising at least one additional therapeutic agent.

36. The composition of claim 35, wherein the agent is selected from the group consisting of vitamin B12, folic acid, ferrous sulfate, human erythropoietin and an erythropoiesis stimulating protein (ESP).

\* \* \* \* \*